US010369196B2

(12) United States Patent
Cohen et al.

(10) Patent No.: US 10,369,196 B2
(45) **Date of Patent: *Aug. 6, 2019**

(54) COMPOSITIONS AND METHODS FOR TREATING GLIOBLASTOMA GBM

(71) Applicant: Vascular Biogenics Ltd., Or Yehuda (IL)

(72) Inventors: Yael Cohen, Kiryat-Ono (IL); Livnat Bangio, Petach-Tikva (IL); Andrew J. Brenner, Boerne, TX (US); Eyal Breitbart, Hashmonaim (IL)

(73) Assignee: Vascular Biogenics Ltd., Or Yehuda (IL)

( * ) Notice: Subject to any disclaimer, the term of this patent is extended or adjusted under 35 U.S.C. 154(b) by 536 days.

This patent is subject to a terminal disclaimer.

(21) Appl. No.: 13/826,303

(22) Filed: Mar. 14, 2013

(65) Prior Publication Data

US 2013/0303595 A1 Nov. 14, 2013

Related U.S. Application Data

(62) Division of application No. 13/520,452, filed as application No. PCT/IL2011/000009 on Jan. 5, 2011.

(60) Provisional application No. 61/282,248, filed on Jan. 7, 2010, provisional application No. 61/282,228, filed on Jan. 5, 2010.

(51) Int. Cl.

| | |
|---|---|
| ***C12N 15/86*** | (2006.01) |
| ***A61K 38/17*** | (2006.01) |
| ***A61K 38/16*** | (2006.01) |
| ***C07K 14/705*** | (2006.01) |
| ***A61K 39/395*** | (2006.01) |
| ***A61K 48/00*** | (2006.01) |
| ***A61N 5/10*** | (2006.01) |
| *A61K 39/00* | (2006.01) |

(52) U.S. Cl.

CPC .......... *A61K 38/177* (2013.01); *A61K 38/162* (2013.01); *A61K 39/39558* (2013.01); *A61K 48/005* (2013.01); *A61N 5/1001* (2013.01); *A61N 5/1077* (2013.01); *C07K 14/70578* (2013.01); *A61K 2039/5258* (2013.01); *A61N 2005/1087* (2013.01); *C12N 2799/022* (2013.01); *Y02E 60/36* (2013.01)

(58) Field of Classification Search

CPC .......... A61K 2039/5258; A61K 38/162; A61K 38/177; C07K 14/70578

See application file for complete search history.

(56) References Cited

U.S. PATENT DOCUMENTS

| | | | |
|---|---|---|---|
| 6,194,191 | B1 | 2/2001 | Zhang et al. |
| 6,204,055 | B1 | 3/2001 | Dean et al. |
| 6,867,022 | B1 | 3/2005 | Imperiale |
| 7,067,649 | B2 | 6/2006 | Harats |
| 7,579,327 | B2 | 8/2009 | Harats et al. |
| 7,585,666 | B2 | 9/2009 | Harats et al. |
| 7,989,427 | B2 | 8/2011 | Harats et al. |
| 8,039,261 | B2 | 10/2011 | Harats et al. |
| 8,071,740 | B2 | 12/2011 | Harats et al. |
| 8,206,743 | B2 | 6/2012 | Harats et al. |
| 8,415,318 | B2 | 8/2013 | Harats et al. |
| 8,916,378 | B2 | 12/2014 | Harats et al. |
| 9,567,605 | B2 | 2/2017 | Cohen et al. |
| 2003/0195338 | A1 | 10/2003 | Chung et al. |
| 2004/0048280 | A1 | 3/2004 | Harats |
| 2004/0170975 | A1 | 9/2004 | Savitzky et al. |
| 2007/0082900 | A1 | 4/2007 | Guzi et al. |
| 2007/0286845 | A1 | 12/2007 | Harats et al. |
| 2008/0063656 | A1 | 3/2008 | Emini et al. |
| 2009/0326052 | A1 | 12/2009 | Harats et al. |
| 2010/0081193 | A1 | 4/2010 | Breitbart et al. |
| 2010/0282634 | A1 | 11/2010 | Harats et al. |
| 2011/0201677 | A1 | 8/2011 | Harats et al. |
| 2011/0207985 | A1 | 8/2011 | Harats et al. |
| 2011/0319479 | A1 | 12/2011 | Breitbart et al. |
| 2012/0201790 | A1 | 8/2012 | Harats et al. |
| 2013/0011367 | A1 | 1/2013 | Harats et al. |
| 2013/0052165 | A1 | 2/2013 | Bangio et al. |
| 2013/0209450 | A1 | 8/2013 | Cohen et al. |
| 2013/0280216 | A1 | 10/2013 | Cohen et al. |
| 2013/0280217 | A1 | 10/2013 | Cohen et al. |
| 2013/0295053 | A1 | 11/2013 | Bangio et al. |

(Continued)

FOREIGN PATENT DOCUMENTS

| | | | |
|---|---|---|---|
| JP | 2004521655 | A | 7/2004 |
| WO | WO-0061150 | A1 | 10/2000 |
| WO | WO 02/40629 | A2 | 5/2002 |

(Continued)

OTHER PUBLICATIONS

Brenner, A.J., et al., "Antivascular activity of VB111 in glioblastoma xenografts," *J. Clin. Oncol.* 28(15):1 page, American Society of Clinical Oncology, United States (2010).

(Continued)

*Primary Examiner* — Anoop K Singh

*Assistant Examiner* — Magdalene K Sgagias

(74) *Attorney, Agent, or Firm* — Sterne, Kessler, Goldstein & Fox P.L.L.C.

(57) ABSTRACT

Methods of treating a malignant glioma in a subject are disclosed. The methods comprise administering to the subject a therapeutically effective amount of a viral vector comprising: (i) a first polynucleotide sequence encoding a Fas-chimera (Fas-c), said first polynucleotide sequence comprising SEQ ID NOs: 2 and 3; and (ii) a second polynucleotide sequence encoding an endothelial cell-specific promoter or a periendothelial cell-specific promoter.

17 Claims, 5 Drawing Sheets

Specification includes a Sequence Listing.

(56) References Cited

U.S. PATENT DOCUMENTS

| | | | |
|---|---|---|---|
| 2013/0296404 | A1 | 11/2013 | Harats et al. |
| 2014/0155467 | A1 | 6/2014 | Harats et al. |

FOREIGN PATENT DOCUMENTS

| | | | |
|---|---|---|---|
| WO | WO 03/033514 | A1 | 4/2003 |
| WO | WO 03/093409 | A2 | 11/2003 |
| WO | WO 2006/051545 | A2 | 5/2006 |
| WO | WO-2006079176 | A1 | 8/2006 |
| WO | WO 2007/096882 | A2 | 8/2007 |
| WO | WO-2008015675 | A2 | 2/2008 |
| WO | WO 2008/132729 | A2 | 11/2008 |
| WO | WO 2011/083464 | A2 | 7/2011 |
| WO | WO 2011/083466 | A1 | 7/2011 |
| WO | WO 2011/086509 | A1 | 7/2011 |
| WO | WO-2014060848 | A2 | 4/2014 |

OTHER PUBLICATIONS

Chi, A.S., et al., "Angiogenesis as a Therapeutic Target in Malignant Gliomas," *Oncologist* 14:621-636, AlphaMed Press, United States (2009).

U.S. Appl. No. 13/785,863 inventors Harats, D., et al., filed Mar. 5, 2013.

U.S. Appl. No. 13/797,160 inventors Cohen, Y., et al., filed Mar. 12, 2013.

U.S. Appl. No. 13/800,478 inventors Harats, D., et al., filed Mar. 13, 2013.

U.S. Appl. No. 13/796,991 inventors Cohen, Y., et al., filed Mar. 12, 2013.

U.S. Appl. No. 13/826,396 inventors Bangio, L., et al., filed Mar. 14, 2013.

U.S. Appl. No. 13/521,691, inventors Bangio, L., et al., filed Mar. 14, 2013.

U.S. Appl. No. 13/520,457 inventors Harats, D., et al., filed Jul. 3, 2012.

Berdichevsky, M., et al., "Establishment of Higher Passage PER.C6 cells for Adenovirus Manufacture," Biotechnology Progress 24(1):158-165, Wiley-Blackwell, United States (2008).

Boldin, M.P., et al., "A novel protein that interacts with the death domain of Fas/APO1 contains a sequence motif related to the death domain," Journal of Biological Chemistry 270(14):7795-7798, American Society for Biochemistry and Molecular Biology, United States (1995).

Brenner, A J., et al., "Phase I/II dose escalation study of VB-111, an antiangiogenic gene therapy, in patients with recurrent glioblastoma multiforme," Journal of Clinical Oncology 31(Suppl 15S, Part I): 1-2, ASCO Annual Meeting, Chicago (2013) (Abstract TPS2102).

Brenner, J., et al., "Phase I Dose-Escalation Study of VB-111, an Antiangiogenic Virotherapy, in Patients with Advanced Solid Tumors," Clinical Cancer Research 19:3996-4007, American Association for Cancer Research, United States (2013).

Greenberger, S., et al., "Transcription-controlled gene therapy against tumor angiogenesis," The Journal of Clinical Investigation 113(7):1017-1024, American Society for Clinical Investigation, United States (2004).

Office Action dated Dec. 8, 2014, in U.S. Appl. No. 13/796,991, Cohen, et al., filed Mar. 12, 2013.

Office Action dated Feb. 25, 2015 in U.S. Appl. No. 13/520,457, Cohen, Y. et al, filed Jul. 3, 2012.

Office Action dated Jul. 1, 2015, in U.S. Appl. No. 13/796,991, Cohen, Y., filed Mar. 12, 2013.

Office Action dated Jul. 7, 2015, in U.S. Appl. No. 13/826,396, Bangio, L., filed Mar. 14, 2013.

Office Action dated Jul. 8, 2014 in U.S. Appl. No. 13/520,457, Cohen, Y. et al, filed Jul. 3, 2012.

Office Action dated Nov. 5, 2013 in U.S. Appl. No. 13/521,691, Bangio, L., et al., filed Jul. 11, 2012.

Office Action dated Oct. 20, 2014, in U.S. Appl. No. 13/521,691, Bangio, L., filed Jul. 11, 2012.

Peled, M., et al., "Antiangiogenic systemic gene therapy combined with doxorubicin administration induced caspase 8 and 9-mediated apoptosis in endothelial cells and an anti-metastasis effect," Cancer Gene Therapy 15(8):535-542, Nature Publishing Group, England (2008).

Peled, M., et al., "Systemic Administration of a Conditionally Replicating Adenovirus, Targeted to Angiogenesis, Reduced Lung Metastases Burden in Cotton Rats," Clinical Cancer Research 15(5):1664-1673, The American Association for Cancer Research, United States (2009).

Roberts, D. M., et al., "Hexon-chimaeric adenovirus serotype 5 vectors circumvent pre-existing anti-vector immunity," Nature 441(7090):239-243, Nature Publishing Group, England (2006).

Roskoski, R. Jr., "Sunitinib: A VEGF and PDGF receptor protein kinase and angiogenesis inhibitor," Biochemical and Biophysical Research Communications 356(2):323-328, Elsevier Inc., United States (2007).

Supplementary European Search Report for EP Application No. 11731735, Munich, Germany, dated Feb. 28, 2014.

Tal, R., et al., "Activation of C-transactivation domain is essential for optimal HIF-1α-mediated transcriptional and angiogenic effects," Microvascular Research 76(1):1-6, Elsevier Inc., United States (2008).

Tal, R., et al., "Endothelial-targeted Gene Transfer of Hypoxia-Inducible Factor-1α Augments Ischemic Neovascularization Following Systemic Administration," Molecular Therapy 16(12):1927-1936, Academic Press, United States (2008).

Tal, R., et al., "Systemic Gene Transfer of Stabilized Constitutively Activated Hypoxia-Inducible Factor-1 Targeted to Endothelium Augments Ischemic Neovascularization," Atherosclerosis Supplements 8(1):3, 76th Congress of the European Atherosclerosis Society, Finland (2007) (Abstract WO3-OR-3).

Thomas, C.E., et al., "Progress and problems with the use of viral vectors for gene therapy," Nature Reviews Genetics 4(5):346-358, (2003).

Tomasoni, S. and Benigni, A., "Gene therapy: how to target the kidney. Promises and pitfalls," Current Gene Therapy 4(1):115-122, Bentham Science Publishers Ltd (2004).

Varda-Bloom, N., et al., "Specific Induction of Tumor Neovasculature Death by Modified Murine PPE-1 Promoter Armed with HSV-TK," Pathobiology 75(6):346-355, S. Karger AG, Basel, Switzerland (2008).

VBL Therapeutics, "VBL Therapeutics Receives FDA Fast Track Designation for Lead Compound VB-111," reuters.com, accessed at http://www.reuters.com/article/2013/11/27/vbl-therapeutics-idUSnBw275428a+100+BSW20131127, accessed on Sep. 12, 2014, 4 pages.

Office Action dated Oct. 20, 2014, in U.S. Appl. No. 13/520,452, Cohen, Y., filed Dec. 19, 2012.

Office Action dated Mar. 29, 2016 in U.S. Appl. No. 13/796,991, Cohen Y. et al., filed Mar. 12, 2013.

Office Action dated Feb. 12, 2016 in U.S. Appl. No. 13/520,457, Cohen, Y. et al., filed Jul. 3, 2012.

Notice of Allowance dated Mar. 10, 2016 in U.S. Appl. No. 13/520,457, Cohen, Y. et al., filed Jul. 3, 2012.

Office Action dated Nov. 4, 2015, in U.S. Appl. No. 13/826,396, Bangio, L. et al., filed Mar. 14, 2013.

Office Action dated Feb. 26, 2016, in U.S. Appl. No. 13/826,396, Bangio, L. et al., filed Mar. 14, 2013.

Office Action dated Nov. 18, 2016, in U.S. Appl. No. 13/826,396, Bangio, L. et al., filed Mar. 14, 2013.

Office Action dated Nov. 13, 2015 in U.S. Appl. No. 13/521,691, Bangio, L., et al., filed Jul. 11, 2012.

Office Action dated Jun. 2, 2016 in U.S. Appl. No. 13/521,691, Bangio, L., et al., filed Jul. 11, 2012.

Office Action dated Jul. 28, 2015, in U.S. Appl. No. 13/520,452, Cohen, Y. et al., filed Dec. 19, 2012.

Office Action dated Feb. 23, 2016, in U.S. Appl. No. 13/520,452, Cohen, Y. et al., filed Dec. 19, 2012.

(56) References Cited

OTHER PUBLICATIONS

GenBank, "tumor necrosis factor receptor superfamily, member 6, [synthetic construct]," Accession No. AAV38887.1, Oct. 28, 2004, accessed at www.ncbi.nlm.nih.gov/protein/54697030?sat=4&satkey=35659413, 1 page.
GenPept, "tumor necrosis factor receptor 1 precursor [*Homo sapiens*]," NCBI Reference Sequence NP_001056.1, Jul. 12, 2009, accessed at www.ncbi.nlm.nih.gov/protein/4507575?sat=13&satkey=3633413/ , 3 pages.
Office Action dated Jun. 9, in U.S. Appl. No. 13/521,691, Bangio, L., filed Jul. 11, 2012 , 23 pages.
Final Office Action dated Jan. 25, 2018, in U.S. Appl. No. 13/521,691, Bangio et al., filed Jul. 11, 2012, 30 pages.
"VBL Therapeutics Announces Top-Line Results from Pivotal Phase 3 GLOBE Study in Patients with Recurrent Glioblastoma," Global Newswire, Mar. 8, 2018, accessed at https://globenewswire.com/news-release/2018/03/08/1418195/0/en/VBL-Therapeutics-Announces-Top-Line-Results-from-Pivotal-Phase-3-GLOBE-Study-in-Patients-with-Recurrent-Glioblastoma.html.
VBL Therapeutics, "Forward-Looking Statements," Company presentation Sep. 2018, 29 pages, accessed at http://ir.vblrx.com/static-files/9f2a9e60-0963-4090-9319-51db7d725871.
Office Action dated Nov. 26, 2018 in U.S. Appl. No. 13/520,452 Cohen, Y., et al., § 371(c) Date Dec. 19, 2012, 18 pages.
Vredenburgh, J.J., et al., "Bevacizumab Plus Irinotecan in Recurrent Glioblastoma Multiforme," Journal of Clinical Oncology 25(30):4722-4729, American Society of Clinical Oncology, United States (2007).

SEQUENCE LISTING

<160> NUMBER OF SEQ ID NOS: 13

<210> SEQ ID NO 1
<211> LENGTH: 34350

<212> TYPE: DNA
<213> ORGANISM: Artificial sequence
<220> FEATURE:
<223> OTHER INFORMATION: Empty Ad5 vector sequence without repeats

<400> SEQUENCE: 1

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagtacgtc tcgagcatgc atctaggcgg    480

ccgcatggca gaaattcgcg aattcgctag cgttaacgga tcctctagac gagatccgaa    540

cttgtttatt gcagcttata atggttacaa ataaagcaat agcatcacaa atttcacaaa    600

taaagcattt ttttcactgc attctagttg tggtttgtcc aaactcatca atgtatctta    660

tcatgtctag atctgtactg aaatgtgtgg gcgtggctta agggtgggaa agaatatata    720

aggtgggggt cttatgtagt tttgtatctg ttttgcagca gccgccgccg ccatgagcac    780

caactcgttt gatggaagca ttgtgagctc atatttgaca acgcgcatgc ccccatgggc    840

cggggtgcgt cagaatgtga tgggctccag cattgatggt cgccccgtcc tgcccgcaaa    900

ctctactacc ttgacctacg agaccgtgtc tggaacgccg ttggagactg cagcctccgc    960

cgccgcttca gccgctgcag ccaccgcccg cgggattgtg actgactttg ctttcctgag   1020

cccgcttgca agcagtgcag cttcccgttc atccgcccgc gatgacaagt tgacggctct   1080

tttggcacaa ttggattctt tgacccggga acttaatgtc gtttctcagc agctgttgga   1140

tctgcgccag caggtttctg ccctgaaggc ttcctcccct cccaatgcgg tttaaaacat   1200

aaataaaaaa ccagactctg tttggatttg gatcaagcaa gtgtcttgct gtctttattt   1260

aggggttttg cgcgcgcggt aggcccggga ccagcggtct cggtcgttga gggtcctgtg   1320

tatttttcc aggacgtggt aaaggtgact ctggatgttc agatacatgg gcataagccc   1380

gtctctgggg tggaggtagc accactgcag agcttcatgc tgcggggtgg tgttgtagat   1440

gatccagtcg tagcaggagc gctgggcgtg gtgcctaaaa atgtctttca gtagcaagct   1500

gattgccagg ggcaggccct tggtgtaagt gtttacaaag cggttaagct gggatgggtg   1560

catacgtggg gatatgagat gcatcttgga ctgtattttt aggttggcta tgttcccagc   1620

catatccctc cggggattca tgttgtgcag aaccaccagc acagtgtatc cggtgcactt   1680

gggaaatttg tcatgtagct tagaaggaaa tgcgtggaag aacttggaga cgcccttgtg   1740

acctccaaga ttttccatgc attcgtccat aatgatggca atgggcccac gggcggcggc   1800

ctgggcgaag atatttctgg gatcactaac gtcatagttg tgttccagga tgagatcgtc   1860

ataggccatt tttacaaagc gcgggcggag ggtgccagac tgcggtataa tggttccatc   1920

cggcccaggg gcgtagttac cctcacagat ttaagggtgg gaaagaatat ataaggtggg   1980

ggtcttatgt agttttgtat ctgttttgca gcagccgccg ccgccatgag caccaactcg   2040

tttgatggaa gcattgtgag ctcatatttg acaacgcgca tgcccccatg ggccggggtg   2100

cgtcagaatg tgatgggctc cagcattgat ggtcgccccg tcctgcccgc aaactctact   2160
```

```
accttgacct acgagaccgt gtctggaacg ccgttggaga ctgcagcctc cgccgccgct   2220
tcagccgctg cagccaccgc ccgcgggatt gtgactgact ttgctttcct gagcccgctt   2280
gcaagcagtg cagcttcccg ttcatccgcc cgcgatgaca agttgacggc tcttttggca   2340
caattggatt ctttgacccg ggaacttaat gtcgtttctc agcagctgtt ggatctgcgc   2400
cagcaggttt ctgccctgaa ggcttcctcc cctcccaatg cggtttaaaa cataaataaa   2460
aaaccagact ctgtttggat ttggatcaag caagtgtctt gctgtcttta tttaggggtt   2520
ttgcgcgcgc ggtaggcccg ggaccagcgg tctcggtcgt tgagggtcct gtgtattttt   2580
tccaggacgt ggtaaaggtg actctggatg ttcagataca tgggcataag cccgtctctg   2640
gggtggaggt agcaccactg cagagcttca tgctgcgggg tggtgttgta gatgatccag   2700
tcgtagcagg agcgctgggc gtggtgccta aaaatgtctt tcagtagcaa gctgattgcc   2760
aggggcaggc ccttggtgta agtgtttaca aagcggttaa gctgggatgg gtgcatacgt   2820
ggggatatga gatgcatctt ggactgtatt tttaggttgg ctatgttccc agccatatcc   2880
ctccggggat tcatgttgtg cagaaccacc agcacagtgt atccggtgca cttgggaaat   2940
ttgtcatgta gcttagaagg aaatgcgtgg aagaacttgg agacgccctt gtgacctcca   3000
agattttcca tgcattcgtc cataatgatg gcaatgggcc cacgggcggc ggcctgggcg   3060
aagatatttc tgggatcact aacgtcatag ttgtgttcca ggatgagatc gtcataggcc   3120
atttttacaa agcgcgggcg gagggtgcca gactgcggta taatggttcc atccggccca   3180
ggggcgtagt taccctcaca gatttgcatt tcccacgctt tgagttcaga tggggggatc   3240
atgtctacct gcggggcgat gaagaaaacg gtttccgggg taggggagat cagctgggaa   3300
gaaagcaggt tcctgagcag ctgcgactta ccgcagccgg tgggcccgta aatcacacct   3360
attaccggct gcaactggta gttaagagag ctgcagctgc cgtcatccct gagcaggggg   3420
gccacttcgt taagcatgtc cctgactcgc atgttttccc tgaccaaatc cgccagaagg   3480
cgctcgccgc ccagcgatag cagttcttgc aaggaagcaa agtttttcaa cggtttgaga   3540
ccgtccgccg taggcatgct tttgagcgtt tgaccaagca gttccaggcg gtcccacagc   3600
tcggtcacct gctctacggc atctcgatcc agcatatctc ctcgtttcgc gggttggggc   3660
ggctttcgct gtacggcagt agtcggtgct cgtccagacg ggccagggtc atgtctttcc   3720
acgggcgcag ggtcctcgtc agcgtagtct gggtcacggt gaaggggtgc gctccgggct   3780
gcgcgctggc cagggtgcgc ttgaggctgg tcctgctggt gctgaagcgc tgccggtctt   3840
cgccctgcgc gtcggccagg tagcatttga ccatggtgtc atagtccagc ccctccgcgg   3900
cgtggccctt ggcgcgcagc ttgcccttgg aggaggcgcc gcacgagggg cagtgcagac   3960
ttttgagggc gtagagcttg ggcgcgagaa ataccgattc cggggagtag gcatccgcgc   4020
cgcaggcccc gcagacggtc tcgcattcca cgagccaggt gagctctggc cgttcggggt   4080
caaaaaccag gtttccccca tgctttttga tgcgtttctt acctctggtt tccatgagcc   4140
ggtgtccacg ctcggtgacg aaaaggctgt ccgtgtcccc gtatacagac ttgagaggcc   4200
tgtcctcgag cggtgttccg cggtcctcct cgtatagaaa ctcggaccac tctgagacaa   4260
aggctcgcgt ccaggccagc acgaaggagg ctaagtggga ggggtagcgg tcgttgtcca   4320
ctagggggtc cactcgctcc agggtgtgaa gacacatgtc gccctcttcg gcatcaagga   4380
aggtgattgg tttgtaggtg taggccacgt gaccgggtgt tcctgaaggg gggctataaa   4440
agggggtggg ggcgcgttcg tcctcactct cttccgcatc gctgtctgcg agggccagct   4500
gttggggtga gtactccctc tgaaaagcgg gcatgacttc tgcgctaaga ttgtcagttt   4560
```

```
ccaaaaacga ggaggatttg atattcacct ggcccgcggt gatgcctttg agggtggccg   4620
catccatctg gtcagaaaag acaatctttt tgttgtcaag cttggtggca aacgacccgt   4680
agagggcgtt ggacagcaac ttggcgatgg agcgcagggt ttggtttttg tcgcgatcgg   4740
cgcgctcctt ggccgcgatg tttagctgca cgtattcgcg cgcaacgcac cgccattcgg   4800
gaaagacggt ggtgcgctcg tcgggcacca ggtgcacgcg ccaaccgcgg ttgtgcaggg   4860
tgacaaggtc aacgctggtg gctacctctc cgcgtaggcg ctcgttggtc cagcagaggc   4920
ggccgccctt gcgcgagcag aatggcggta gggggtctag ctgcgtctcg tccgggggt   4980
ctgcgtccac ggtaaagacc ccgggcagca ggcgcgcgtc gaagtagtct atcttgcatc   5040
cttgcaagtc tagcgcctgc tgccatgcgc gggcggcaag cgcgcgctcg tatgggttga   5100
gtgggggacc ccatggcatg gggtgggtga gcgcggaggc gtacatgccg caaatgtcgt   5160
aaacgtagag gggctctctg agtattccaa gatatgtagg gtagcatctt ccaccgcgga   5220
tgctggcgcg cacgtaatcg tatagttcgt gcgagggagc gaggaggtcg ggaccgaggt   5280
tgctacgggc gggctgctct gctcggaaga ctatctgcct gaagatggca tgtgagttgg   5340
atgatatggt tggacgctgg aagacgttga agctggcgtc tgtgagacct accgcgtcac   5400
gcacgaagga ggcgtaggag tcgcgcagct tgttgaccag ctcggcggtg acctgcacgt   5460
ctagggcgca gtagtccagg gtttccttga tgatgtcata cttatcctgt cccttttttt   5520
tccacagctc gcggttgagg acaaactctt cgcggtcttt ccagtactct tggatcggaa   5580
acccgtcggc ctccgaacgg taagagccta gcatgtagaa ctggttgacg gcctggtagg   5640
cgcagcatcc cttttctacg ggtagcgcgt atgcctgcgc ggccttccgg agcgaggtgt   5700
gggtgagcgc aaaggtgtcc ctgaccatga ctttgaggta ctggtatttg aagtcagtgt   5760
cgtcgcatcc gccctgctcc cagagcaaaa agtccgtgcg ctttttggaa cgcggatttg   5820
gcagggcgaa ggtgacatcg ttgaagagta tctttcccgc gcgaggcata aagttgcgtg   5880
tgatgcggaa gggtcccggc acctcggaac ggttgttaat tacctgggcg gcgagcacga   5940
tctcgtcaaa gccgttgatg ttgtggccca caatgtaaag ttccaagaag cgcgggatgc   6000
ccttgatgga aggcaatttt ttaagttcct cgtaggtgag ctcttcaggg gagctgagcc   6060
cgtgctctga aagggcccag tctgcaagat gagggttgga agcgacgaat gagctccaca   6120
ggtcacgggc cattagcatt tgcaggtggt cgcgaaaggt cctaaactgg cgacctatgg   6180
ccattttttc tggggtgatg cagtagaagg taagcgggtc ttgttcccag cggtcccatc   6240
caaggttcgc ggctaggtct cgcgcggcag tcactagagg ctcatctccg ccgaacttca   6300
tgaccagcat gaagggcacg agctgcttcc caaaggcccc catccaagta taggtctcta   6360
catcgtaggt gacaaagaga cgctcggtgc gaggatgcga gccgatcggg aagaactgga   6420
tctcccgcca ccaattggag gagtggctat tgatgtggtg aaagtagaag tccctgcgac   6480
gggccgaaca ctcgtgctgg cttttgtaaa aacgtgcgca gtactggcag cggtgcacgg   6540
gctgtacatc ctgcacgagg ttgacctgac gaccgcgcac aaggaagcag agtgggaatt   6600
tgagcccctc gcctggcggg tttggctggt ggtcttctac ttcggctgct tgtccttgac   6660
cgtctggctg ctcgagggga gttacggtgg atcggaccac cacgccgcgc gagcccaaag   6720
tccagatgtc cgcgcgcggc ggtcggagct tgatgacaac atcgcgcaga tgggagctgt   6780
ccatggtctg gagctcccgc ggcgtcaggt caggcgggag ctcctgcagg tttacctcgc   6840
atagacgggt cagggcgcgg gctagatcca ggtgatacct aatttccagg ggctggttgg   6900
```

```
tggcggcgtc gatggcttgc aagaggccgc atccccgcgg cgcgactacg gtaccgcgcg   6960
gcgggcggtg ggccgcgggg gtgtccttgg atgatgcatc taaaagcggt gacgcgggcg   7020
agcccccgga ggtagggggg gctccggacc cgccgggaga gggggcaggg gcacgtcggc   7080
gccgcgcgcg ggcaggagct ggtgctgcgc gcgtaggttg ctggcgaacg cgacgacgcg   7140
gcggttgatc tcctgaatct ggcgcctctg cgtgaagacg acgggcccgg tgagcttgaa   7200
cctgaaagag agttcgacag aatcaatttc ggtgtcgttg acggcggcct ggcgcaaaat   7260
ctcctgcacg tctcctgagt tgtcttgata ggcgatctcg gccatgaact gctcgatctc   7320
ttcctcctgg agatctccgc gtccggctcg ctccacggtg gcggcgaggt cgttggaaat   7380
gcgggccatg agctgcgaga aggcgttgag gcctccctcg ttccagacgc ggctgtagac   7440
cacgccccct tcggcatcgc gggcgcgcat gaccacctgc gcgagattga gctccacgtg   7500
ccgggcgaag acggcgtagt ttcgcaggcg ctgaaagagg tagttgaggg tggtggcggt   7560
gtgttctgcc acgaagaagt acataaccca gcgtcgcaac gtggattcgt tgatatcccc   7620
caaggcctca aggcgctcca tggcctcgta gaagtccacg gcgaagttga aaaactggga   7680
gttgcgcgcc gacacggtta actcctcctc cagaagacgg atgagctcgg cgacagtgtc   7740
gcgcacctcg cgctcaaagg ctacaggggc ctcttcttct tcttcaatct cctcttccat   7800
aagggcctcc ccttcttctt cttctggcgg cggtggggga gggggggacac ggcggcgacg   7860
acggcgcacc gggaggcggt cgacaaagcg ctcgatcatc tccccgcggc gacggcgcat   7920
ggtctcggtg acggcgcggc cgttctcgcg gggcgcagt tggaagacgc cgcccgtcat   7980
gtcccggtta tgggttggcg gggggctgcc atgcggcagg gatacggcgc taacgatgca   8040
tctcaacaat tgttgtgtag gtactccgcc gccgagggac ctgagcgagt ccgcatcgac   8100
cggatcggaa aacctctcga gaaaggcgtc taaccagtca cagtcgcaag gtaggctgag   8160
caccgtggcg ggcggcagcg ggcggcggtc ggggttgttt ctggcggagg tgctgctgat   8220
gatgtaatta aagtaggcgg tcttgagacg gcggatggtc gacagaagca ccatgtcctt   8280
gggtccggcc tgctgaatgc gcaggcggtc ggccatgccc caggcttcgt tttgacatcg   8340
gcgcaggtct ttgtagtagt cttgcatgag cctttctacc ggcacttctt cttctccttc   8400
ctcttgtcct gcatctcttg catctatcgc tgcggcggcg gcggagtttg gccgtaggtg   8460
gcgccctctt cctcccatgc gtgtgacccc gaagcccctc atcggctgaa gcagggctag   8520
gtcggcgaca acgcgctcgg ctaatatggc ctgctgcacc tgcgtgaggg tagactggaa   8580
gtcatccatg tccacaaagc ggtggtatgc gcccgtgttg atggtgtaag tgcagttggc   8640
cataacggac cagttaacgg tctggtgacc cggctgcgag agctcggtgt acctgagacg   8700
cgagtaagcc ctcgagtcaa atacgtagtc gttgcaagtc cgcaccaggt actggtatcc   8760
caccaaaaag tgcggcggcg gctggcggta gaggggccag cgtagggtgg ccggggctcc   8820
gggggcgaga tcttccaaca taaggcgatg atatccgtag atgtacctgg acatccaggt   8880
gatgccggcg gcggtggtgg aggcgcgcgg aaagtcgcgg acgcggttcc agatgttgcg   8940
cagcggcaaa aagtgctcca tggtcgggac gctctggccg gtcaggcgcg cgcaatcgtt   9000
gacgctctag accgtgcaaa aggagagcct gtaagcgggc actcttccgt ggtctggtgg   9060
ataaattcgc aagggtatca tggcggacga ccggggttcg agccccgtat ccggccgtcc   9120
gccgtgatcc atgcggttac cgcccgcgtg tcgaacccag gtgtgcgacg tcagacaacg   9180
ggggagtgct ccttttggct tccttccagg cgcggcggct gctgcgctag ctttttttggc   9240
cactggccgc gcgcagcgta agcggttagg ctggaaagcg aaagcattaa gtggctcgct   9300
```

```
ccctgtagcc ggagggttat tttccaaggg ttgagtcgcg ggacccccgg ttcgagtctc   9360
ggaccggccg gactgcggcg aacgggggtt tgcctccccg tcatgcaaga ccccgcttgc   9420
aaattcctcc ggaaacaggg acgagcccct tttttgcttt tcccagatgc atccggtgct   9480
gcggcagatg cgccccccctc ctcagcagcg gcaagagcaa gagcagcggc agacatgcag   9540
ggcaccctcc cctcctccta ccgcgtcagg aggggcgaca tccgcggttg acgcggcagc   9600
agatggtgat tacgaacccc cgcggcgccg ggcccggcac tacctggact tggaggaggg   9660
cgagggcctg gcgcggctag gagcgccctc tcctgagcgg cacccaaggg tgcagctgaa   9720
gcgtgatacg cgtgaggcgt acgtgccgcg gcagaacctg tttcgcgacc gcgagggaga   9780
ggagcccgag gagatgcggg atcgaaagtt ccacgcaggg cgcgagctgc ggcatggcct   9840
gaatcgcgag cggttgctgc gcgaggagga ctttgagccc gacgcgcgaa ccgggattag   9900
tcccgcgcgc gcacacgtgg cggccgccga cctggtaacc gcatacgagc agacggtgaa   9960
ccaggagatt aactttcaaa aaagctttaa caaccacgtg cgtacgcttg tggcgcgcga  10020
ggaggtggct ataggactga tgcatctgtg ggactttgta agcgcgctgg agcaaaaccc  10080
aaatagcaag ccgctcatgg cgcagctgtt ccttatagtg cagcacagca gggacaacga  10140
ggcattcagg gatgcgctgc taaacatagt agagcccgag ggccgctggc tgctcgattt  10200
gataaacatc ctgcagagca tagtggtgca ggagcgcagc ttgagcctgg ctgacaaggt  10260
ggccgccatc aactattcca tgcttagcct gggcaagttt tacgcccgca agatatacca  10320
taccccttac gttcccatag acaaggaggt aaagatcgag gggttctaca tgcgcatggc  10380
gctgaaggtg cttaccttga gcgacgacct gggcgtttat cgcaacgagc gcatccacaa  10440
ggccgtgagc gtgagccggc ggcgcgagct cagcgaccgc gagctgatgc acagcctgca  10500
aagggccctg gctggcacgg gcagcggcga tagagaggcc gagtcctact ttgacgcggg  10560
cgctgacctg cgctgggccc caagccgacg cgccctggag gcagctgggg ccggacctgg  10620
gctggcggtg gcacccgcgc gcgctggcaa cgtcggcggc gtggaggaat atgacgagga  10680
cgatgagtac gagccagagg acggcgagta ctaagcggtg atgtttctga tcagatgatg  10740
caagacgcaa cggacccggc ggtgcgggcg gcgctgcaga gccagccgtc cggccttaac  10800
tccacggacg actggcgcca ggtcatggac cgcatcatgt cgctgactgc gcgcaatcct  10860
gacgcgttcc ggcagcagcc gcaggccaac cggctctccg caattctgga agcggtggtc  10920
ccggcgcgcg caaaccccac gcacgagaag gtgctggcga tcgtaaacgc gctggccgaa  10980
aacagggcca tccggcccga cgaggccggc ctggtctacg acgcgctgct tcagcgcgtg  11040
gctcgttaca acagcggcaa cgtgcagacc aacctggacc ggctggtggg ggatgtgcgc  11100
gaggccgtgg cgcagcgtga gcgcgcgcag cagcagggca acctgggctc catggttgca  11160
ctaaacgcct tcctgagtac acagcccgcc aacgtgccgc ggggacagga ggactacacc  11220
aactttgtga gcgcactgcg gctaatggtg actgagacac cgcaaagtga ggtgtaccag  11280
tctgggccag actatttttt ccagaccagt agacaaggcc tgcagaccgt aaacctgagc  11340
caggctttca aaaacttgca ggggctgtgg ggggtgcggg ctcccacagg cgaccgcgcg  11400
accgtgtcta gcttgctgac gcccaactcg cgcctgttgc tgctgctaat agcgcccttc  11460
acggacagtg gcagcgtgtc ccgggacaca tacctaggtc acttgctgac actgtaccgc  11520
gaggccatag gtcaggcgca tgtggacgag catactttcc aggagattac aagtgtcagc  11580
cgcgcgctgg ggcaggagga cacgggcagc ctggaggcaa ccctaaacta cctgctgacc  11640
```

```
aaccggcggc agaagatccc ctcgttgcac agtttaaaca gcgaggagga gcgcattttg  11700
cgctacgtgc agcagagcgt gagccttaac ctgatgcgcg acggggtaac gcccagcgtg  11760
gcgctggaca tgaccgcgcg caacatggaa ccgggcatgt atgcctcaaa ccggccgttt  11820
atcaaccgcc taatggacta cttgcatcgc gcggccgccg tgaaccccga gtatttcacc  11880
aatgccatct tgaacccgca ctggctaccg ccccctggtt tctacaccgg gggattcgag  11940
gtgcccgagg gtaacgatgg attcctctgg gacgacatag acgacagcgt gttttccccg  12000
caaccgcaga ccctgctaga gttgcaacag cgcgagcagg cagaggcggc gctgcgaaag  12060
gaaagcttcc gcaggccaag cagcttgtcc gatctaggcg ctgcggcccc gcggtcagat  12120
gctagtagcc catttccaag cttgataggg tctcttacca gcactcgcac cacccgcccg  12180
cgcctgctgg gcgaggagga gtacctaaac aactcgctgc tgcagccgca gcgcgaaaaa  12240
aacctgcctc cggcatttcc caacaacggg atagagagcc tagtggacaa gatgagtaga  12300
tggaagacgt acgcgcagga gcacagggac gtgccaggcc cgcgcccgcc cacccgtcgt  12360
caaaggcacg accgtcagcg gggtctggtg tgggaggacg atgactcggc agacgacagc  12420
agcgtcctgg atttgggagg gagtggcaac ccgtttgcgc accttcgccc caggctgggg  12480
agaatgtttt aaaaaaaaaa aaagcatgat gcaaaataaa aaactcacca aggccatggc  12540
accgagcgtt ggttttcttg tattcccctt agtatgcggc gcgcggcgat gtatgaggaa  12600
ggtcctcctc cctcctacga gagtgtggtg agcgcggcgc cagtggcggc ggcgctgggt  12660
tctcccttcg atgctcccct ggacccgccg tttgtgcctc cgcggtacct gcggcctacc  12720
ggggggagaa acagcatccg ttactctgag ttggcacccc tattcgacac cacccgtgtg  12780
tacctggtgg acaacaagtc aacggatgtg gcatccctga actaccagaa cgaccacagc  12840
aactttctga ccacggtcat tcaaaacaat gactacagcc cgggggaggc aagcacacag  12900
accatcaatc ttgacgaccg gtcgcactgg ggcggcgacc tgaaaaccat cctgcatacc  12960
aacatgccaa atgtgaacga gttcatgttt accaataagt ttaaggcgcg ggtgatggtg  13020
tcgcgcttgc ctactaagga caatcaggtg gagctgaaat acgagtgggt ggagttcacg  13080
ctgcccgagg gcaactactc cgagaccatg accatagacc ttatgaacaa cgcgatcgtg  13140
gagcactact tgaaagtggg cagacagaac ggggttctgg aaagcgacat cggggtaaag  13200
tttgacaccc gcaacttcag actggggttt gaccccgtca ctggtcttgt catgcctggg  13260
gtatatacaa acgaagcctt ccatccagac atcattttgc tgccaggatg cggggtggac  13320
ttcacccaca gccgcctgag caacttgttg ggcatccgca agcggcaacc cttccaggag  13380
ggctttagga tcacctacga tgatctggag ggtggtaaca ttcccgcact gttggatgtg  13440
gacgcctacc aggcgagctt gaaagatgac accgaacagg gcgggggtgg cgcaggcggc  13500
agcaacagca gtggcagcgg cgcggaagag aactccaacg cggcagccgc ggcaatgcag  13560
ccggtggagg acatgaacga tcatgccatt cgcggcgaca cctttgccac acgggctgag  13620
gagaagcgcg ctgaggccga agcagcggcc gaagctgccg cccccgctgc gcaacccgag  13680
gtcgagaagc ctcagaagaa accggtgatc aaacccctga cagaggacag caagaaacgc  13740
agttacaacc taataagcaa tgacagcacc ttcacccagt accgcagctg gtaccttgca  13800
tacaactacg gcgaccctca gaccggaatc cgctcatgga ccctgctttg cactcctgac  13860
gtaacctgcg gctcggagca ggtctactgg tcgttgccag acatgatgca agaccccgtg  13920
accttccgct ccacgcgcca gatcagcaac tttccggtgg tgggcgccga gctgttgccc  13980
gtgcactcca agagcttcta caacgaccag gccgtctact cccaactcat ccgccagttt  14040
```

```
acctctctga cccacgtgtt caatcgcttt cccgagaacc agattttggc gcgcccgcca  14100
gcccccacca tcaccaccgt cagtgaaaac gttcctgctc tcacagatca cgggacgcta  14160
ccgctgcgca acagcatcgg aggagtccag cgagtgacca ttactgacgc cagacgccgc  14220
acctgcccct acgtttacaa ggccctgggc atagtctcgc cgcgcgtcct atcgagccgc  14280
actttttgag caagcatgtc catccttata tcgcccagca ataacacagg ctggggcctg  14340
cgcttcccaa gcaagatgtt tggcggggcc aagaagcgct ccgaccaaca cccagtgcgc  14400
gtgcgcgggc actaccgcgc gccctggggc gcgcacaaac gcggccgcac tgggcgcacc  14460
accgtcgatg acgccatcga cgcggtggtg gaggaggcgc gcaactacac gcccacgccg  14520
ccaccagtgt ccacagtgga cgcggccatt cagaccgtgg tgcgcggagc ccggcgctat  14580
gctaaaatga agagacggcg gaggcgcgta gcacgtcgcc accgccgccg acccggcact  14640
gccgcccaac gcgcggcggc ggccctgctt aaccgcgcac gtcgcaccgg ccgacgggcg  14700
gccatgcggg ccgctcgaag gctggccgcg ggtattgtca ctgtgccccc caggtccagg  14760
cgacgagcgg ccgccgcagc agccgcggcc attagtgcta tgactcaggg tcgcaggggc  14820
aacgtgtatt gggtgcgcga ctcggttagc ggcctgcgcg tgcccgtgcg cacccgcccc  14880
ccgcgcaact agattgcaag aaaaaactac ttagactcgt actgttgtat gtatccagcg  14940
gcggcggcgc gcaacgaagc tatgtccaag cgcaaaatca aagaagagat gctccaggtc  15000
atcgcgccgg agatctatgg ccccccgaag aaggaagagc aggattacaa gccccgaaag  15060
ctaaagcggg tcaaaaagaa aaagaaagat gatgatgatg aacttgacga cgaggtggaa  15120
ctgctgcacg ctaccgcgcc caggcgacgg gtacagtgga aaggtcgacg cgtaaaacgt  15180
gttttgcgac ccggcaccac cgtagtcttt acgcccggtg agcgctccac ccgcacctac  15240
aagcgcgtgt atgatgaggt gtacggcgac gaggacctgc ttgagcaggc caacgagcgc  15300
ctcggggagt ttgcctacgg aaagcggcat aaggacatgc tggcgttgcc gctggacgag  15360
ggcaacccaa cacctagcct aaagcccgta acactgcagc aggtgctgcc cgcgcttgca  15420
ccgtccgaag aaaagcgcgg cctaaagcgc gagtctggtg acttggcacc caccgtgcag  15480
ctgatggtac ccaagcgcca gcgactggaa gatgtcttgg aaaaaatgac cgtggaacct  15540
gggctggagc ccgaggtccg cgtgcggcca atcaagcagg tggcgccggg actgggcgtg  15600
cagaccgtgg acgttcagat acccactacc agtagcacca gtattgccac cgccacagag  15660
ggcatggaga cacaaacgtc cccggttgcc tcagcggtgg cggatgccgc ggtgcaggcg  15720
gtcgctgcgg ccgcgtccaa gacctctacg gaggtgcaaa cggacccgtg gatgtttcgc  15780
gtttcagccc cccggcgccc gcgccgttcg aggaagtacg gcgccgccag cgcgctactg  15840
cccgaatatg ccctacatcc ttccattgcg cctacccccg gctatcgtgg ctacacctac  15900
cgccccagaa gacgagcaac tacccgacgc cgaaccacca ctggaacccg ccgccgccgt  15960
cgccgtcgcc agcccgtgct ggccccgatt tccgtgcgca gggtggctcg cgaaggaggc  16020
aggaccctgg tgctgccaac agcgcgctac caccccagca tcgtttaaaa gccggtcttt  16080
gtggttcttg cagatatggc cctcacctgc cgcctccgtt tcccggtgcc gggattccga  16140
ggaagaatgc accgtaggag gggcatggcc ggccacggcc tgacgggcgg catgcgtcgt  16200
gcgcaccacc ggcggcggcg cgcgtcgcac cgtcgcatgc gcggcggtat cctgcccctc  16260
cttattccac tgatcgccgc ggcgattggc gccgtgcccg gaattgcatc cgtggccttg  16320
caggcgcaga gacactgatt aaaaacaagt tgcatgtgga aaatcaaaa taaaaagtct  16380
```

```
ggactctcac gctcgcttgg tcctgtaact attttgtaga atggaagaca tcaactttgc  16440
gtctctggcc ccgcgacacg gctcgcgccc gttcatggga aactggcaag atatcggcac  16500
cagcaatatg agcggtggcg ccttcagctg gggctcgctg tggagcggca ttaaaaattt  16560
cggttccacc gttaagaact atggcagcaa ggcctggaac agcagcacag gccagatgct  16620
gagggataag ttgaaagagc aaaatttcca acaaaaggtg gtagatggcc tggcctctgg  16680
cattagcggg gtggtggacc tggccaacca ggcagtgcaa aataagatta acagtaagct  16740
tgatccccgc cctcccgtag aggagcctcc accggccgtg gagacagtgt ctccagaggg  16800
gcgtggcgaa aagcgtccgc gccccgacag ggaagaaact ctggtgacgc aaatagacga  16860
gcctccctcg tacgaggagg cactaaagca aggcctgccc accacccgtc ccatcgcgcc  16920
catggctacc ggagtgctgg gccagcacac acccgtaacg ctggacctgc ctccccccgc  16980
cgacacccag cagaaacctg tgctgccagg cccgaccgcc gttgttgtaa cccgtcctag  17040
ccgcgcgtcc ctgcgccgcg ccgccagcgg tccgcgatcg ttgcggcccg tagccagtgg  17100
caactggcaa agcacactga acagcatcgt gggtctgggg gtgcaatccc tgaagcgccg  17160
acgatgcttc tgatagctaa cgtgtcgtat gtgtgtcatg tatgcgtcca tgtcgccgcc  17220
agaggagctg ctgagccgcc gcgcgcccgc tttccaagat ggctacccct tcgatgatgc  17280
cgcagtggtc ttacatgcac atctcgggcc aggacgcctc ggagtacctg agccccgggc  17340
tggtgcagtt tgcccgcgcc accgagacgt acttcagcct gaataacaag tttagaaacc  17400
ccacggtggc gcctacgcac gacgtgacca cagaccggtc ccagcgtttg acgctgcggt  17460
tcatccctgt ggaccgtgag gatactgcgt actcgtacaa ggcgcggttc accctagctg  17520
tgggtgataa ccgtgtgctg gacatggctt ccacgtactt tgacatccgc ggcgtgctgg  17580
acaggggccc tacttttaag ccctactctg gcactgccta caacgccctg gctcccaagg  17640
gtgccccaaa tccttgcgaa tgggatgaag ctgctactgc tcttgaaata aacctagaag  17700
aagaggacga tgacaacgaa gacgaagtag acgagcaagc tgagcagcaa aaaactcacg  17760
tatttgggca ggcgccttat tctggtataa atattacaaa ggagggtatt caaataggtg  17820
tcgaaggtca aacacctaaa tatgccgata aaacatttca acctgaacct caaataggag  17880
aatctcagtg gtacgaaaca gaaattaatc atgcagctgg gagagtccta aaaaagacta  17940
ccccaatgaa accatgttac ggttcatatg caaaacccac aaatgaaaat ggagggcaag  18000
gcattcttgt aaagcaacaa aatggaaagc tagaaagtca agtggaaatg caatttttct  18060
caactactga ggcagccgca ggcaatggtg ataacttgac tcctaaagtg gtattgtaca  18120
gtgaagatgt agatatagaa accccagaca ctcatatttc ttacatgccc actattaagg  18180
aaggtaactc acgagaacta atgggccaac aatctatgcc caacaggcct aattacattg  18240
cttttaggga caattttatt ggtctaatgt attacaacag cacgggtaat atgggtgttc  18300
tggcgggcca agcatcgcag ttgaatgctg ttgtagattt gcaagacaga aacacagagc  18360
tttcatacca gcttttgctt gattccattg gtgatagaac caggtacttt tctatgtgga  18420
atcaggctgt tgacagctat gatccagatg ttagaattat tgaaaatcat ggaactgaag  18480
atgaacttcc aaattactgc tttccactgg gaggtgtgat taatacagag actcttacca  18540
aggtaaaacc taaaacaggt caggaaaatg gatgggaaaa agatgctaca gaattttcag  18600
ataaaaatga aataagagtt ggaaataatt ttgccatgga aatcaatcta aatgccaacc  18660
tgtggagaaa tttcctgtac tccaacatag cgctgtattt gcccgacaag ctaaagtaca  18720
gtccttccaa cgtaaaaatt tctgataacc caaacaccta cgactacatg aacaagcgag  18780
```

```
tggtggctcc cgggctagtg gactgctaca ttaaccttgg agcacgctgg tcccttgact  18840
atatggacaa cgtcaaccca tttaaccacc accgcaatgc tggcctgcgc taccgctcaa  18900
tgttgctggg caatggtcgc tatgtgccct tccacatcca ggtgcctcag aagttctttg  18960
ccattaaaaa cctccttctc ctgccgggct catacaccta cgagtggaac ttcaggaagg  19020
atgttaacat ggttctgcag agctccctag gaaatgacct aagggttgac ggagccagca  19080
ttaagtttga tagcatttgc ctttacgcca ccttcttccc catggcccac aacaccgcct  19140
ccacgcttga ggccatgctt agaaacgaca ccaacgacca gtcctttaac gactatctct  19200
ccgccgccaa catgctctac cctatacccg ccaacgctac caacgtgccc atatccatcc  19260
cctcccgcaa ctgggcggct ttccgcggct gggccttcac gcgccttaag actaaggaaa  19320
ccccatcact gggctcgggc tacgaccctt attacaccta ctctggctct ataccctacc  19380
tagatggaac cttttacctc aaccacacct ttaagaaggt ggccattacc tttgactctt  19440
ctgtcagctg gcctggcaat gaccgcctgc ttacccccaa cgagtttgaa attaagcgct  19500
cagttgacgg ggagggttac aacgttgccc agtgtaacat gaccaaagac tggttcctgg  19560
tacaaatgct agctaactat aacattggct accagggctt ctatatccca gagagctaca  19620
aggaccgcat gtactccttc tttagaaact tccagcccat gagccgtcag gtggtggatg  19680
atactaaata caaggactac caacaggtgg gcatcctaca ccaacacaac aactctggat  19740
ttgttggcta ccttgccccc accatgcgcg aaggacaggc ctaccctgct aacttcccct  19800
atccgcttat aggcaagacc gcagttgaca gcattaccca gaaaaagttt ctttgcgatc  19860
gcaccctttg gcgcatccca ttctccagta actttatgtc catgggcgca ctcacagacc  19920
tgggccaaaa ccttctctac gccaactccg cccacgcgct agacatgact tttgaggtgg  19980
atcccatgga cgagcccacc cttctttatg ttttgtttga agtctttgac gtggtccgtg  20040
tgcaccagcc gcaccgcggc gtcatcgaaa ccgtgtacct gcgcacgccc ttctcggccg  20100
gcaacgccac aacataaaga agcaagcaac atcaacaaca gctgccgcca tgggctccag  20160
tgagcaggaa ctgaaagcca ttgtcaaaga tcttggttgt gggccatatt ttttgggcac  20220
ctatgacaag cgctttccag gctttgtttc tccacacaag ctcgcctgcg ccatagtcaa  20280
tacggccggt cgcgagactg gggggcgtaca ctggatggcc tttgcctgga acccgcactc  20340
aaaaacatgc tacctctttg agccctttgg cttttctgac cagcgactca agcaggttta  20400
ccagtttgag tacgagtcac tcctgcgccg tagcgccatt gcttcttccc ccgaccgctg  20460
tataacgctg gaaaagtcca cccaaagcgt acaggggccc aactcggccg cctgtggact  20520
attctgctgc atgtttctcc acgcctttgc caactggccc caaactccca tggatcacaa  20580
ccccaccatg aaccttatta ccggggtacc caactccatg ctcaacagtc cccaggtaca  20640
gcccaccctg cgtcgcaacc aggaacagct ctacagcttc ctggagcgcc actcgcccta  20700
cttccgcagc cacagtgcgc agattaggag cgccacttct ttttgtcact tgaaaaacat  20760
gtaaaaataa tgtactagag acactttcaa taaaggcaaa tgcttttatt tgtacactct  20820
cgggtgatta tttacccccca cccttgccgt ctgcgccgtt taaaaatcaa aggggttctg  20880
ccgcgcatcg ctatgcgcca ctggcaggga cacgttgcga tactggtgtt tagtgctcca  20940
cttaaactca ggcacaacca tccgcggcag ctcggtgaag ttttcactcc acaggctgcg  21000
caccatcacc aacgcgttta gcaggtcggg cgccgatatc ttgaagtcgc agttggggcc  21060
tccgccctgc gcgcgcgagt tgcgatacac agggttgcag cactggaaca ctatcagcgc  21120
```

```
cgggtggtgc acgctggcca gcacgctctt gtcggagatc agatccgcgt ccaggtcctc  21180
cgcgttgctc agggcgaacg gagtcaactt tggtagctgc cttcccaaaa agggcgcgtg  21240
cccaggcttt gagttgcact cgcaccgtag tggcatcaaa aggtgaccgt gcccggtctg  21300
ggcgttagga tacagcgcct gcataaaagc cttgatctgc ttaaaagcca cctgagcctt  21360
tgcgccttca gagaagaaca tgccgcaaga cttgccggaa aactgattgg ccggacaggc  21420
cgcgtcgtgc acgcagcacc ttgcgtcggt gttggagatc tgcaccacat ttcggcccca  21480
ccggttcttc acgatcttgg ccttgctaga ctgctccttc agcgcgcgct gcccgttttc  21540
gctcgtcaca tccatttcaa tcacgtgctc cttatttatc ataatgcttc cgtgtagaca  21600
cttaagctcg ccttcgatct cagcgcagcg gtgcagccac aacgcgcagc ccgtgggctc  21660
gtgatgcttg taggtcacct ctgcaaacga ctgcaggtac gcctgcagga atcgccccat  21720
catcgtcaca aaggtcttgt tgctggtgaa ggtcagctgc aacccgcggt gctcctcgtt  21780
cagccaggtc ttgcatacgg ccgccagagc ttccacttgg tcaggcagta gtttgaagtt  21840
cgcctttaga tcgttatcca cgtggtactt gtccatcagc gcgcgcgcag cctccatgcc  21900
cttctcccac gcagacacga tcggcacact cagcgggttc atcaccgtaa tttcactttc  21960
cgcttcgctg ggctcttcct cttcctcttg cgtccgcata ccacgcgcca ctgggtcgtc  22020
ttcattcagc cgccgcactg tgcgcttacc tcctttgcca tgcttgatta gcaccggtgg  22080
gttgctgaaa cccaccattt gtagcgccac atcttctctt tcttcctcgc tgtccacgat  22140
tacctctggt gatggcgggc gctcgggctt gggagaaggg cgcttctttt tcttcttggg  22200
cgcaatggcc aaatccgccg ccgaggtcga tggccgcggg ctgggtgtgc gcggcaccag  22260
cgcgtcttgt gatgagtctt cctcgtcctc ggactcgata cgccgcctca tccgcttttt  22320
tgggggcgcc cggggaggcg gcggcgacgg ggacggggac gacacgtcct ccatggttgg  22380
gggacgtcgc gccgcaccgc gtccgcgctc gggggtggtt tcgcgctgct cctcttcccg  22440
actggccatt tccttctcct ataggcagaa aaagatcatg gagtcagtcg agaagaagga  22500
cagcctaacc gccccctctg agttcgccac caccgcctcc accgatgccg ccaacgcgcc  22560
taccaccttc cccgtcgagg cacccccgct tgaggaggag gaagtgatta tcgagcagga  22620
cccaggtttt gtaagcgaag acgacgagga ccgctcagta ccaacagagg ataaaaagca  22680
agaccaggac aacgcagagg caaacgagga acaagtcggg cggggggacg aaaggcatgg  22740
cgactaccta gatgtgggag acgacgtgct gttgaagcat ctgcagcgcc agtgcgccat  22800
tatctgcgac gcgttgcaag agcgcagcga tgtgcccctc gccatagcgg atgtcagcct  22860
tgcctacgaa cgccacctat tctcaccgcg cgtacccccc aaacgccaag aaaacggcac  22920
atgcgagccc aacccgcgcc tcaacttcta ccccgtattt gccgtgccag aggtgcttgc  22980
cacctatcac atctttttcc aaaactgcaa gataccccta tcctgccgtg ccaaccgcag  23040
ccgagcggac aagcagctgg ccttgcggca gggcgctgtc atacctgata tcgcctcgct  23100
caacgaagtg ccaaaaatct ttgagggtct tggacgcgac gagaagcgcg cggcaaacgc  23160
tctgcaacag gaaaacagcg aaaatgaaag tcactctgga gtgttggtgg aactcgaggg  23220
tgacaacgcg cgcctagccg tactaaaacg cagcatcgag gtcacccact ttgcctaccc  23280
ggcacttaac ctacccccca aggtcatgag cacagtcatg agtgagctga tcgtgcgccg  23340
tgcgcagccc ctggagaggg atgcaaattt gcaagaacaa acagaggagg gcctacccgc  23400
agttggcgac gagcagctag cgcgctggct tcaaacgcgc gagcctgccg acttggagga  23460
gcgacgcaaa ctaatgatgg ccgcagtgct cgttaccgtg gagcttgagt gcatgcagcg  23520
```

```
gttctttgct gacccggaga tgcagcgcaa gctagaggaa acattgcact acacctttcg  23580

acagggctac gtacgccagg cctgcaagat ctccaacgtg gagctctgca acctggtctc  23640

ctaccttgga attttgcacg aaaaccgcct tgggcaaaac gtgcttcatt ccacgctcaa  23700

gggcgaggcg cgccgcgact acgtccgcga ctgcgtttac ttatttctat gctacacctg  23760

gcagacggcc atgggcgttt ggcagcagtg cttggaggag tgcaacctca aggagctgca  23820

gaaactgcta aagcaaaact tgaaggacct atggacggcc ttcaacgagc gctccgtggc  23880

cgcgcacctg gcggacatca ttttccccga acgcctgctt aaaaccctgc aacagggtct  23940

gccagacttc accagtcaaa gcatgttgca gaactttagg aactttatcc tagagcgctc  24000

aggaatcttg cccgccacct gctgtgcact tcctagcgac tttgtgccca ttaagtaccg  24060

cgaatgccct ccgccgcttt ggggccactg ctaccttctg cagctagcca actaccttgc  24120

ctaccactct gacataatgg aagacgtgag cggtgacggt ctactggagt gtcactgtcg  24180

ctgcaaccta tgcaccccgc accgctccct ggtttgcaat tcgcagctgc ttaacgaaag  24240

tcaaattatc ggtacctttg agctgcaggg tccctcgcct gacgaaaagt ccgcggctcc  24300

ggggttgaaa ctcactccgg ggctgtggac gtcggcttac cttcgcaaat ttgtacctga  24360

ggactaccac gcccacgaga ttaggttcta cgaagaccaa tcccgcccgc ctaatgcgga  24420

gcttaccgcc tgcgtcatta cccagggcca cattcttggc caattgcaag ccatcaacaa  24480

agcccgccaa gagtttctgc tacgaaaggg acggggggtt tacttggacc cccagtccgg  24540

cgaggagctc aacccaatcc ccccgccgcc gcagccctat cagcagcagc cgcgggccct  24600

tgcttcccag gatggcaccc aaaaagaagc tgcagctgcc gccgccaccc acggacgagg  24660

aggaatactg ggacagtcag gcagaggagg ttttggacga ggaggaggag gacatgatgg  24720

aagactggga gagcctagac gaggaagctt ccgaggtcga agaggtgtca gacgaaacac  24780

cgtcaccctc ggtcgcattc ccctcgccgg cgccccagaa atcggcaacc ggttccagca  24840

tggctacaac ctccgctcct caggcgccgc cggcactgcc cgttcgccga cccaaccgta  24900

gatgggacac cactggaacc agggccggta agtccaagca gccgccgccg ttagcccaag  24960

agcaacaaca gcgccaaggc taccgctcat ggcgcgggca caagaacgcc atagttgctt  25020

gcttgcaaga ctgtgggggc aacatctcct tcgcccgccg ctttcttctc taccatcacg  25080

gcgtggcctt cccccgtaac atcctgcatt actaccgtca tctctacagc ccatactgca  25140

ccggcggcag cggcagcaac agcagcggcc acacagaagc aaaggcgacc ggatagcaag  25200

actctgacaa agcccaagaa atccacagcg gcggcagcag caggaggagg agcgctgcgt  25260

ctggcgccca acgaacccgt atcgacccgc gagcttagaa acaggatttt tcccactctg  25320

tatgctatat ttcaacagag caggggccaa gaacaagagc tgaaaataaa aaacaggtct  25380

ctgcgatccc tcacccgcag ctgcctgtat cacaaaagcg aagatcagct tcggcgcacg  25440

ctggaagacg cggaggctct cttcagtaaa tactgcgcgc tgactcttaa ggactagttt  25500

cgcgcccttt ctcaaattta agcgcgaaaa ctacgtcatc tccagcggcc acacccggcg  25560

ccagcacctg ttgtcagcgc cattatgagc aaggaaattc ccacgcccta catgtggagt  25620

taccagccac aaatgggact tgcggctgga gctgcccaag actactcaac ccgaataaac  25680

tacatgagcg cgggacccca catgatatcc cgggtcaacg gaatacgcgc ccaccgaaac  25740

cgaattctcc tggaacaggc ggctattacc accacacctc gtaataacct taatccccgt  25800

agttggcccg ctgccctggt gtaccaggaa agtcccgctc ccaccactgt ggtacttccc  25860
```

```
agagacgccc aggccgaagt tcagatgact aactcagggg cgcagcttgc gggcggcttt  25920
cgtcacaggg tgcggtcgcc cgggcagggt ataactcacc tgacaatcag agggcgaggt  25980
attcagctca acgacgagtc ggtgagctcc tcgcttggtc tccgtccgga cgggacattt  26040
cagatcggcg gcgccggccg ctcttcattc acgcctcgtc aggcaatcct aactctgcag  26100
acctcgtcct ctgagccgcg ctctggaggc attggaactc tgcaatttat tgaggagttt  26160
gtgccatcgg tctactttaa ccccttctcg ggacctcccg gccactatcc ggatcaattt  26220
attcctaact ttgacgcggt aaaggactcg gcggacggct acgactgaat gttaagtgga  26280
gaggcagagc aactgcgcct gaaacacctg gtccactgtc gccgccacaa gtgctttgcc  26340
cgcgactccg gtgagttttg ctactttgaa ttgcccgagg atcatatcga gggcccggcg  26400
cacggcgtcc ggcttaccgc ccagggagag cttgcccgta gcctgattcg ggagtttacc  26460
cagcgccccc tgctagttga gcgggacagg ggaccctgtg ttctcactgt gatttgcaac  26520
tgtcctaacc ctggattaca tcaagatctt tgttgccatc tctgtgctga gtataataaa  26580
tacagaaatt aaaatatact ggggctccta tcgccatcct gtaaacgcca ccgtcttcac  26640
ccgcccaagc aaaccaaggc gaaccttacc tggtactttt aacatctctc cctctgtgat  26700
ttacaacagt ttcaacccag acggagtgag tctacgagag aacctctccg agctcagcta  26760
ctccatcaga aaaaacacca ccctccttac ctgccgggaa cgtacgagtg cgtcaccggc  26820
cgctgcacca cacctaccgc ctgaccgtaa accagacttt ttccggacag acctcaataa  26880
ctctgtttac cagaacagga ggtgagctta gaaaaccctt agggtattag gccaaaggcg  26940
cagctactgt ggggtttatg aacaattcaa gcaactctac gggctattct aattcaggtt  27000
tctctagaat cggggttggg gttattctct gtcttgtgat tctctttatt cttatactaa  27060
cgcttctctg cctaaggctc gccgcctgct gtgtgcacat ttgcatttat tgtcagcttt  27120
ttaaacgctg ggtcgccac ccaagatgat taggtacata atcctaggtt tactcaccct  27180
tgcgtcagcc cacggtacca cccaaaaggt ggattttaag gagccagcct gtaatgttac  27240
attcgcagct gaagctaatg agtgcaccac tcttataaaa tgcaccacag aacatgaaaa  27300
gctgcttatt cgccacaaaa acaaaattgg caagtatgct gtttatgcta tttggcagcc  27360
aggtgacact acagagtata atgttacagt tttccagggt aaaagtcata aaacttttat  27420
gtatactttt ccattttatg aaatgtgcga cattaccatg tacatgagca aacagtataa  27480
gttgtggccc ccacaaaatt gtgtggaaaa cactggcact ttctgctgca ctgctatgct  27540
aattacagtg ctcgctttgg tctgtaccct actctatatt aaatacaaaa gcagacgcag  27600
ctttattgag gaaaagaaaa tgccttaatt tactaagtta caaagctaat gtcaccacta  27660
actgctttac tcgctgcttg caaaacaaat tcaaaaagtt agcattataa ttagaatagg  27720
atttaaaccc cccggtcatt tcctgctcaa taccattccc ctgaacaatt gactctatgt  27780
gggatatgct ccagcgctac aaccttgaag tcaggcttcc tggatgtcag catctgactt  27840
tggccagcac ctgtcccgcg gatttgttcc agtccaacta cagcgaccca ccctaacaga  27900
gatgaccaac acaaccaacg cggccgccgc taccggactt acatctacca caaatacacc  27960
ccaagtttct gcctttgtca ataactggga taacttgggc atgtggtggt tctccatagc  28020
gcttatgttt gtatgcctta ttattatgtg gctcatctgc tgcctaaagc gcaaacgcgc  28080
ccgaccaccc atctatagtc ccatcattgt gctacaccca aacaatgatg gaatccatag  28140
attggacgga ctgaaacaca tgttcttttc tcttacagta tgattaaatg agacatgatt  28200
cctcgagttt ttatattact gacccttgtt gcgctttttt tgtgcgtgct ccacattggc  28260
```

```
tgcggtttct cacatcgaag tagactgcat tccagccttc acagtctatt tgctttacgg  28320
atttgtcacc ctcacgctca tctgcagcct catcactgtg gtcatcgcct ttatccagtg  28380
cattgactgg gtctgtgtgc gctttgcata tctcagacac catccccagt acagggacag  28440
gactatagct gagcttctta gaattcttta attatgaaat ttactgtgac ttttctgctg  28500
attatttgca ccctatctgc gttttgttcc ccgacctcca agcctcaaag acatatatca  28560
tgcagattca ctcgtatatg gaatattcca agttgctaca atgaaaaaag cgatctttcc  28620
gaagcctggt tatatgcaat catctctgtt atggtgttct gcagtaccat cttagcccta  28680
gctatatatc cctaccttga cattggctgg aacgcaatag atgccatgaa ccacccaact  28740
ttccccgcgc ccgctatgct tccactgcaa caagttgttg ccggcggctt tgtcccagcc  28800
aatcagcctc gcccaccttc tcccaccccc actgaaatca gctactttaa tctaacagga  28860
ggagatgact gacaccctag atctagaaat ggacggaatt attacagagc agcgcctgct  28920
agaaagacgc agggcagcgg ccgagcaaca gcgcatgaat caagagctcc aagacatggt  28980
taacttgcac cagtgcaaaa ggggtatctt ttgtctggta aagcaggcca aagtcaccta  29040
cgacagtaat accaccggac accgccttag ctacaagttg ccaaccaagc gtcagaaatt  29100
ggtggtcatg gtgggagaaa agcccattac cataactcag cactcggtag aaaccgaagg  29160
ctgcattcac tcaccttgtc aaggacctga ggatctctgc acccttatta agaccctgtg  29220
cggtctcaaa gatcttattc cctttaacta ataaaaaaaa ataataaagc atcacttact  29280
taaaatcagt tagcaaattt ctgtccagtt tattcagcag cacctccttg ccctcctccc  29340
agctctggta ttgcagcttc ctcctggctg caaactttct ccacaatcta aatggaatgt  29400
cagtttcctc ctgttcctgt ccatccgcac ccactatctt catgttgttg cagatgaagc  29460
gcgcaagacc gtctgaagat accttcaacc ccgtgtatcc atatgacacg gaaaccggtc  29520
ctccaactgt gccttttctt actcctccct ttgtatcccc caatgggttt caagagagtc  29580
cccctggggt actctctttg cgcctatccg aacctctagt tacctccaat ggcatgcttg  29640
cgctcaaaat gggcaacggc ctctctctgg acgaggccgg caaccttacc tcccaaaatg  29700
taaccactgt gagcccacct ctcaaaaaaa ccaagtcaaa cataaacctg gaaatatctg  29760
cacccctcac agttacctca gaagccctaa ctgtggctgc cgccgcacct ctaatggtcg  29820
cgggcaacac actcaccatg caatcacagg ccccgctaac cgtgcacgac tccaaactta  29880
gcattgccac ccaaggaccc ctcacagtgt cagaaggaaa gctagccctg caaacatcag  29940
gcccccctcac caccaccgat agcagtaccc ttactatcac tgcctcaccc cctctaacta  30000
ctgccactgg tagcttgggc attgacttga aagagcccat ttatacacaa aatggaaaac  30060
taggactaaa gtacggggct cctttgcatg taacagacga cctaaacact ttgaccgtag  30120
caactggtcc aggtgtgact attaataata cttccttgca aactaaagtt actggagcct  30180
tgggttttga ttcacaaggc aatatgcaac ttaatgtagc aggaggacta aggattgatt  30240
ctcaaaacag acgccttata cttgatgtta gttatccgtt tgatgctcaa aaccaactaa  30300
atctaagact aggacagggc cctcttttta taaactcagc ccacaacttg gatattaact  30360
acaacaaagg cctttacttg tttacagctt caaacaattc caaaaagctt gaggttaacc  30420
taagcactgc caaggggttg atgtttgacg ctacagccat agccattaat gcaggagatg  30480
ggcttgaatt tggttcacct aatgcaccaa acacaaatcc cctcaaaaca aaaattggcc  30540
atggcctaga atttgattca aacaaggcta tggttcctaa actaggaact ggccttagtt  30600
```

```
ttgacagcac aggtgccatt acagtaggaa acaaaaataa tgataagcta actttgtgga  30660
ccacaccagc tccatctcct aactgtagac taaatgcaga gaaagatgct aaactcactt  30720
tggtcttaac aaaatgtggc agtcaaatac ttgctacagt ttcagttttg gctgttaaag  30780
gcagtttggc tccaatatct ggaacagttc aaagtgctca tcttattata agatttgacg  30840
aaaatggagt gctactaaac aattccttcc tggacccaga atattggaac tttagaaatg  30900
gagatcttac tgaaggcaca gcctatacaa acgctgttgg atttatgcct aacctatcag  30960
cttatccaaa atctcacggt aaaactgcca aaagtaacat tgtcagtcaa gtttacttaa  31020
acggagacaa aactaaacct gtaacactaa ccattacact aaacggtaca caggaaacag  31080
gagacacaac tccaagtgca tactctatgt cattttcatg ggactggtct ggccacaact  31140
acattaatga aatatttgcc acatcctctt acactttttc atacattgcc caagaataaa  31200
gaatcgtttg tgttatgttt caacgtgttt atttttcaat tgcagaaaat ttcaagtcat  31260
ttttcattca gtagtatagc cccaccacca catagcttat acagatcacc gtaccttaat  31320
caaactcaca gaaccctagt attcaacctg ccacctccct cccaacacac agagtacaca  31380
gtcctttctc cccggctggc cttaaaaagc atcatatcat gggtaacaga catattctta  31440
ggtgttatat tccacacggt ttcctgtcga gccaaacgct catcagtgat attaataaac  31500
tccccgggca gctcacttaa gttcatgtcg ctgtccagct gctgagccac aggctgctgt  31560
ccaacttgcg gttgcttaac gggcggcgaa ggagaagtcc acgcctacat gggggtagag  31620
tcataatcgt gcatcaggat agggcggtgg tgctgcagca gcgcgcgaat aaactgctgc  31680
cgccgccgct ccgtcctgca ggaatacaac atggcagtgg tctcctcagc gatgattcgc  31740
accgcccgca gcataaggcg ccttgtcctc cgggcacagc agcgcaccct gatctcactt  31800
aaatcagcac agtaactgca gcacagcacc acaatattgt tcaaaatccc acagtgcaag  31860
gcgctgtatc caaagctcat ggcggggacc acagaaccca cgtggccatc ataccacaag  31920
cgcaggtaga ttaagtggcg acccctcata aacacgctgg acataaacat tacctctttt  31980
ggcatgttgt aattcaccac ctcccggtac catataaacc tctgattaaa catggcgcca  32040
tccaccacca tcctaaacca gctggccaaa acctgcccgc cggctataca ctgcagggaa  32100
ccgggactgg aacaatgaca gtggagagcc caggactcgt aaccatggat catcatgctc  32160
gtcatgatat caatgttggc acaacacagg cacacgtgca tacacttcct caggattaca  32220
agctcctccc gcgttagaac catatcccag ggaacaaccc attcctgaat cagcgtaaat  32280
cccacactgc agggaagacc tcgcacgtaa ctcacgttgt gcattgtcaa agtgttacat  32340
tcgggcagca gcggatgatc ctccagtatg gtagcgcggg tttctgtctc aaaaggaggt  32400
agacgatccc tactgtacgg agtgcgccga gacaaccgag atcgtgttgg tcgtagtgtc  32460
atgccaaatg gaacgccgga cgtagtcata tttcctgaag caaaaccagg tgcgggcgtg  32520
acaaacagat ctgcgtctcc ggtctcgccg cttagatcgc tctgtgtagt agttgtagta  32580
tatccactct ctcaaagcat ccaggcgccc cctggcttcg ggttctatgt aaactccttc  32640
atgcgccgct gccctgataa catccaccac cgcagaataa gccacaccca gccaacctac  32700
acattcgttc tgcgagtcac acacgggagg agcgggaaga gctggaagaa ccatgttttt  32760
ttttttattc caaaagatta tccaaaacct caaaatgaag atctattaag tgaacgcgct  32820
cccctccggt ggcgtggtca aactctacag ccaaagaaca gataatggca tttgtaagat  32880
gttgcacaat ggcttccaaa aggcaaacgg ccctcacgtc caagtggacg taaaggctaa  32940
acccttcagg gtgaatctcc tctataaaca ttccagcacc ttcaaccatg cccaaataat  33000
```

```
tctcatctcg ccaccttctc aatatatctc taagcaaatc ccgaatatta agtccggcca  33060

ttgtaaaaat ctgctccaga gcgccctcca ccttcagcct caagcagcga atcatgattg  33120

caaaaattca ggttcctcac agacctgtat aagattcaaa agcggaacat taacaaaaat  33180

accgcgatcc cgtaggtccc ttcgcagggc cagctgaaca taatcgtgca ggtctgcacg  33240

gaccagcgcg gccacttccc cgccaggaac catgacaaaa gaacccacac tgattatgac  33300

acgcatactc ggagctatgc taaccagcgt agccccgatg taagcttgtt gcatgggcgg  33360

cgatataaaa tgcaaggtgc tgctcaaaaa atcaggcaaa gcctcgcgca aaaaagaaag  33420

cacatcgtag tcatgctcat gcagataaag gcaggtaagc tccggaacca ccacagaaaa  33480

agacaccatt tttctctcaa acatgtctgc gggtttctgc ataaacacaa aataaaataa  33540

caaaaaaaca tttaaacatt agaagcctgt cttacaacag gaaaaacaac ccttataagc  33600

ataagacgga ctacggccat gccggcgtga ccgtaaaaaa actggtcacc gtgattaaaa  33660

agcaccaccg acagctcctc ggtcatgtcc ggagtcataa tgtaagactc ggtaaacaca  33720

tcaggttgat tcacatcggt cagtgctaaa aagcgaccga aatagcccgg gggaatacat  33780

acccgcaggc gtagagacaa cattacagcc cccataggag gtataacaaa attaatagga  33840

gagaaaaaca cataaacacc tgaaaaaccc tcctgcctag gcaaaatagc accctcccgc  33900

tccagaacaa catacagcgc ttccacagcg gcagccataa cagtcagcct taccagtaaa  33960

aaagaaaacc tattaaaaaa acaccactcg acacggcacc agctcaatca gtcacagtgt  34020

aaaaaagggc caagtgcaga gcgagtatat ataggactaa aaaatgacgt aacggttaaa  34080

gtccacaaaa aacacccaga aaaccgcacg cgaacctacg cccagaaacg aaagccaaaa  34140

aacccacaac ttcctcaaat cgtcacttcc gttttcccac gttacgtcac ttcccatttt  34200

aagaaaacta caattcccaa cacatacaag ttactccgcc ctaaaaccta cgtcacccgc  34260

cccgttccca cgccccgcgc cacgtcacaa actccacccc ctcattatca tattggcttc  34320

aatccaaaat aaggtatatt attgatgatg                                   34350
```

```
<210> SEQ ID NO 2
<211> LENGTH: 590
<212> TYPE: DNA
<213> ORGANISM: Artificial sequence
<220> FEATURE:
<223> OTHER INFORMATION: TNFR portion of the TNFR-Fas chimera (Fas-c)

<400> SEQUENCE: 2

atgggcctct ccaccgtgcc tgacctgctg ctgccgctgg tgctcctgga gctgttggtg     60

ggaatatacc cctcaggggt tattggactg gtccctcacc taggggacag ggagaagaga    120

gatagtgtgt gtccccaagg aaaatatatc caccctcaaa ataattcgat ttgctgtacc    180

aagtgccaca aaggaaccta cttgtacaat gactgtccag gcccggggca ggatacggac    240

tgcagggagt gtgagagcgg ctccttcacc gcttcagaaa accacctcag acactgcctc    300

agctgctcca aatgccgaaa ggaaatgggt caggtggaga tctcttcttg cacagtggac    360

cgggacaccg tgtgtggctg caggaagaac cagtaccggc attattggag tgaaaacctt    420

ttccagtgct tcaattgcag cctctgcctc aatgggaccg tgcacctctc ctgccaggag    480

aaacagaaca ccgtgtgcac ctgccatgca ggtttctttc taagagaaaa cgagtgtgtc    540

tcctgtagta actgtaagaa aagcctggag tgcacgaagt tgtgcctacc               590

<210> SEQ ID NO 3
```

<211> LENGTH: 511
<212> TYPE: DNA
<213> ORGANISM: Artificial sequence
<220> FEATURE:
<223> OTHER INFORMATION: Fas portion of the TNFR-Fas chimera (Fas-c)

<400> SEQUENCE: 3

```
aagcttagga tccagatcta acttggggtg gctttgtctt cttcttttgc caattccact     60

aattgtttgg gtgaagagaa aggaagtaca gaaaacatgc agaaagcaca gaaaggaaaa    120

ccaaggttct catgaatctc caaccttaaa tcctgaaaca gtggcaataa atttatctga    180

tgttgacttg agtaaatata tcaccactat tgctggagtc atgacactaa gtcaagttaa    240

aggctttgtt cgaaagaatg gtgtcaatga agccaaaata gatgagatca agaatgacaa    300

tgtccaagac acagcagaac agaaagttca actgcttcgt aattggcatc aacttcatgg    360

aaagaaagaa gcgtatgaca cattgattaa agatctcaaa aaagccaatc tttgtactct    420

tgcagagaaa attcagacta tcatcctcaa ggacattact agtgactcag aaaattcaaa    480

cttcagaaat gaaatccaaa gcttggtcta g                                   511
```

<210> SEQ ID NO 4
<211> LENGTH: 1101
<212> TYPE: DNA
<213> ORGANISM: Artificial sequence
<220> FEATURE:
<223> OTHER INFORMATION: TNFR1-Fas chimera (Fas-c) coding sequence

<400> SEQUENCE: 4

```
atgggcctct ccaccgtgcc tgacctgctg ctgccgctgg tgctcctgga gctgttggtg     60

ggaatatacc cctcaggggt tattggactg gtccctcacc taggggacag ggagaagaga    120

gatagtgtgt gtccccaagg aaaatatatc caccctcaaa ataattcgat ttgctgtacc    180

aagtgccaca aaggaaccta cttgtacaat gactgtccag gcccggggca ggatacggac    240

tgcagggagt gtgagagcgg ctccttcacc gcttcagaaa accacctcag acactgcctc    300

agctgctcca aatgccgaaa ggaaatgggt caggtggaga tctcttcttg cacagtggac    360

cgggacaccg tgtgtggctg caggaagaac cagtaccggc attattggag tgaaaacctt    420

ttccagtgct tcaattgcag cctctgcctc aatgggaccg tgcacctctc ctgccaggag    480

aaacagaaca ccgtgtgcac ctgccatgca ggtttctttc taagagaaaa cgagtgtgtc    540

tcctgtagta actgtaagaa aagcctggag tgcacgaagt tgtgcctacc aagcttagga    600

tccagatcta acttggggtg gctttgtctt cttcttttgc caattccact aattgtttgg    660

gtgaagagaa aggaagtaca gaaaacatgc agaaagcaca gaaaggaaaa ccaaggttct    720

catgaatctc caaccttaaa tcctgaaaca gtggcaataa atttatctga tgttgacttg    780

agtaaatata tcaccactat tgctggagtc atgacactaa gtcaagttaa aggctttgtt    840

cgaaagaatg gtgtcaatga agccaaaata gatgagatca agaatgacaa tgtccaagac    900

acagcagaac agaaagttca actgcttcgt aattggcatc aacttcatgg aaagaaagaa    960

gcgtatgaca cattgattaa agatctcaaa aaagccaatc tttgtactct tgcagagaaa   1020

attcagacta tcatcctcaa ggacattact agtgactcag aaaattcaaa cttcagaaat   1080

gaaatccaaa gcttggtcta g                                             1101
```

<210> SEQ ID NO 5
<211> LENGTH: 6
<212> TYPE: DNA
<213> ORGANISM: Artificial sequence

```
<220> FEATURE:
<223> OTHER INFORMATION: Hypoxia responsive element - E-box

<400> SEQUENCE: 5

gcacgt                                                                  6


<210> SEQ ID NO 6
<211> LENGTH: 44
<212> TYPE: DNA
<213> ORGANISM: Artificial sequence
<220> FEATURE:
<223> OTHER INFORMATION: Murine endothelial specific enhancer elemet

<400> SEQUENCE: 6

gtacttcata cttttcattc caatggggtg actttgcttc tgga                       44


<210> SEQ ID NO 7
<211> LENGTH: 143
<212> TYPE: DNA
<213> ORGANISM: Artificial sequence
<220> FEATURE:
<223> OTHER INFORMATION: A triplicate copy of a murine enhancer sequence
      originated from the PPE-1 promoter

<400> SEQUENCE: 7

gtacttcata cttttcattc caatggggtg actttgcttc tggagggtga ctttgcttct      60

ggagccagta cttcatactt ttcattgtac ttcatacttt tcattccaat ggggtgactt     120

tgcttctgga ggctagctgc cag                                             143


<210> SEQ ID NO 8
<211> LENGTH: 47
<212> TYPE: DNA
<213> ORGANISM: Artificial sequence
<220> FEATURE:
<223> OTHER INFORMATION: EDC fragment

<400> SEQUENCE: 8

ctggagggtg actttgcttc tggagccagt acttcatact tttcatt                    47


<210> SEQ ID NO 9
<211> LENGTH: 36460
<212> TYPE: DNA
<213> ORGANISM: Artificial sequence
<220> FEATURE:
<223> OTHER INFORMATION: PPE-1-3X-FasC virl construct including repeat
      sequences
<220> FEATURE:
<221> NAME/KEY: misc_feature
<222> LOCATION: (460)..(1437)
<223> OTHER INFORMATION: A modified murine pre-proendothelin-1 promoter
      (PPE-1-3X)
<220> FEATURE:
<221> NAME/KEY: misc_feature
<222> LOCATION: (1438)..(1468)
<223> OTHER INFORMATION: Linker containing Restriction sites (NotI,
      PstI, BamHI)
<220> FEATURE:
<221> NAME/KEY: misc_feature
<222> LOCATION: (1469)..(2058)
<223> OTHER INFORMATION: TNFR portion of the Fas-TNFR-1 chimera (Fas-c)
<220> FEATURE:
<221> NAME/KEY: misc_feature
<222> LOCATION: (2059)..(2569)
<223> OTHER INFORMATION: FAS portion of the Fas-TNFR-1 chimera (Fas-c)
<220> FEATURE:
<221> NAME/KEY: misc_feature
<222> LOCATION: (2801)..(4062)
<223> OTHER INFORMATION: Duplication - copy 1
<220> FEATURE:
```

<221> NAME/KEY: misc_feature
<222> LOCATION: (4063)..(5315)
<223> OTHER INFORMATION: Duplication - copy 2

<400> SEQUENCE: 9

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtacgta cgtgtacttc tgatcggcga    480
tactagggag ataaggatgt acctgacaaa accacattgt tgttgttatc attattattt    540
agttttcctt ccttgctaac tcctgacgga atctttctca cctcaaatgc gaagtacttt    600
agtttagaaa agacttggtg gaaggggtgg tggtggaaaa gtagggtgat cttccaaact    660
aatctggttc cccgcccgcc ccagtagctg ggattcaaga gcgaagagtg ggatcgtcc     720
ccttgtttga tcagaaagac ataaaaggaa aatcaagtga acaatgatca gccccacctc    780
caccccaccc ccctgcgcgc gcacaataca atctatttaa ttgtacttca tacttttcat    840
tccaatgggg tgactttgct tctggagaaa ctcttgattc ttgaactctg gggctggcag    900
ctagcctcca gaagcaaagt caccccattg gaatgaaaag tatgaagtac aatgaaaagt    960
atgaagtact ggctccagaa gcaaagtcac cctccagaag caaagtcacc ccattggaat   1020
gaaaagtatg aagtacgcta gcaaaagggg aagcgggctg ctgctctctg caggttctgc   1080
agcggtctct gtctagtggg tgttttcttt ttcttagccc tgcccctgga ttgtcagacg   1140
gcgggcgtct gcctctgaag ttagccgtga tttcctctag agccgggtct tatctctggc   1200
tgcacgttgc ctgtgggtga ctaatcacac aataacattg tttagggctg gaataaagtc   1260
agagctgttt acccccactc tataggggtt caatataaaa aggcggcgga gaactgtccg   1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatataccccc tcaggggtta ttggactggt   1560
ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaacctttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
```

-continued ggcaataaat ttatctgatg ttgacttgag taaatatatc accactattg ctggagtcat 2280
gacactaagt caagttaaag gctttgttcg aaagaatggt gtcaatgaag ccaaaataga 2340
tgagatcaag aatgacaatg tccaagacac agcagaacag aaagttcaac tgcttcgtaa 2400
ttggcatcaa cttcatggaa agaaagaagc gtatgacaca ttgattaaag atctcaaaaa 2460
agccaatctt tgtactcttg cagagaaaat tcagactatc atcctcaagg acattactag 2520
tgactcagaa aattcaaact tcagaaatga aatccaaagc ttggtctagc tcgagcatgc 2580
atctaggcgg ccgcatggca gaaattcgcg aattcgctag cgttaacgga tcctctagac 2640
gagatccgaa cttgtttatt gcagcttata atggttacaa ataaagcaat agcatcacaa 2700
atttcacaaa taaagcattt ttttcactgc attctagttg tggtttgtcc aaactcatca 2760
atgtatctta tcatgtctag atctgtactg aaatgtgtgg gcgtggctta agggtgggaa 2820
agaatatata aggtgggggt cttatgtagt tttgtatctg ttttgcagca gccgccgccg 2880
ccatgagcac caactcgttt gatggaagca ttgtgagctc atatttgaca acgcgcatgc 2940
ccccatgggc cggggtgcgt cagaatgtga tgggctccag cattgatggt cgccccgtcc 3000
tgcccgcaaa ctctactacc ttgacctacg agaccgtgtc tggaacgccg ttggagactg 3060
cagcctccgc cgccgcttca gccgctgcag ccaccgcccg cgggattgtg actgactttg 3120
ctttcctgag cccgcttgca agcagtgcag cttcccgttc atccgcccgc gatgacaagt 3180
tgacggctct tttggcacaa ttggattctt tgacccggga acttaatgtc gtttctcagc 3240
agctgttgga tctgcgccag caggtttctg ccctgaaggc ttcctcccct cccaatgcgg 3300
tttaaaacat aaataaaaaa ccagactctg tttggatttg gatcaagcaa gtgtcttgct 3360
gtctttattt aggggttttg cgcgcgcggt aggcccggga ccagcggtct cggtcgttga 3420
gggtcctgtg tatttttttcc aggacgtggt aaaggtgact ctggatgttc agatacatgg 3480
gcataagccc gtctctgggg tggaggtagc accactgcag agcttcatgc tgcggggtgg 3540
tgttgtagat gatccagtcg tagcaggagc gctgggcgtg gtgcctaaaa atgtctttca 3600
gtagcaagct gattgccagg ggcaggccct tggtgtaagt gtttacaaag cggttaagct 3660
gggatgggtg catacgtggg gatatgagat gcatcttgga ctgtattttt aggttggcta 3720
tgttcccagc catatccctc cggggattca tgttgtgcag aaccaccagc acagtgtatc 3780
cggtgcactt gggaaatttg tcatgtagct tagaaggaaa tgcgtggaag aacttggaga 3840
cgcccttgtg acctccaaga ttttccatgc attcgtccat aatgatggca atgggcccac 3900
gggcggcggc ctgggcgaag atatttctgg gatcactaac gtcatagttg tgttccagga 3960
tgagatcgtc ataggccatt tttacaaagc gcgggcggag ggtgccagac tgcggtataa 4020
tggttccatc cggcccaggg gcgtagttac cctcacagat ttaagggtgg gaaagaatat 4080
ataaggtggg ggtcttatgt agttttgtat ctgttttgca gcagccgccg ccgccatgag 4140
caccaactcg tttgatggaa gcattgtgag ctcatatttg acaacgcgca tgcccccatg 4200
ggccggggtg cgtcagaatg tgatgggctc cagcattgat ggtcgccccg tcctgcccgc 4260
aaactctact accttgacct acgagaccgt gtctggaacg ccgttggaga ctgcagcctc 4320
cgccgccgct tcagccgctg cagccaccgc ccgcgggatt gtgactgact ttgctttcct 4380
gagcccgctt gcaagcagtg cagcttcccg ttcatccgcc cgcgatgaca agttgacggc 4440
tcttttggca caattggatt ctttgacccg ggaacttaat gtcgtttctc agcagctgtt 4500
ggatctgcgc cagcaggttt ctgccctgaa ggcttcctcc cctcccaatg cggtttaaaa 4560

-continued

```
cataaataaa aaaccagact ctgtttggat ttggatcaag caagtgtctt gctgtcttta   4620
tttaggggtt ttgcgcgcgc ggtaggcccg ggaccagcgg tctcggtcgt tgagggtcct   4680
gtgtattttt tccaggacgt ggtaaaggtg actctggatg ttcagataca tgggcataag   4740
cccgtctctg ggtggaggt agcaccactg cagagcttca tgctgcgggg tggtgttgta   4800
gatgatccag tcgtagcagg agcgctgggc gtggtgccta aaaatgtctt tcagtagcaa   4860
gctgattgcc aggggcaggc ccttggtgta agtgtttaca aagcggttaa gctgggatgg   4920
gtgcatacgt ggggatatga gatgcatctt ggactgtatt tttaggttgg ctatgttccc   4980
agccatatcc ctccggggat tcatgttgtg cagaaccacc agcacagtgt atccggtgca   5040
cttgggaaat ttgtcatgta gcttagaagg aaatgcgtgg aagaacttgg agacgccctt   5100
gtgacctcca agattttcca tgcattcgtc cataatgatg gcaatgggcc cacgggcggc   5160
ggcctgggcg aagatatttc tgggatcact aacgtcatag ttgtgttcca ggatgagatc   5220
gtcataggcc atttttacaa agcgcgggcg gagggtgcca gactgcggta taatggttcc   5280
atccggccca ggggcgtagt taccctcaca gatttgcatt tcccacgctt tgagttcaga   5340
tggggggatc atgtctacct gcggggcgat gaagaaaacg gtttccgggg taggggagat   5400
cagctgggaa gaaagcaggt tcctgagcag ctgcgactta ccgcagccgg tgggcccgta   5460
aatcacacct attaccggct gcaactggta gttaagagag ctgcagctgc cgtcatccct   5520
gagcaggggg gccacttcgt taagcatgtc cctgactcgc atgttttccc tgaccaaatc   5580
cgccagaagg cgctcgccgc ccagcgatag cagttcttgc aaggaagcaa agtttttcaa   5640
cggtttgaga ccgtccgccg taggcatgct tttgagcgtt tgaccaagca gttccaggcg   5700
gtcccacagc tcggtcacct gctctacggc atctcgatcc agcatatctc ctcgtttcgc   5760
gggttggggc ggctttcgct gtacggcagt agtcggtgct cgtccagacg ggccagggtc   5820
atgtctttcc acgggcgcag ggtcctcgtc agcgtagtct gggtcacggt gaaggggtgc   5880
gctccgggct gcgcgctggc cagggtgcgc ttgaggctgg tcctgctggt gctgaagcgc   5940
tgccggtctt cgccctgcgc gtcggccagg tagcatttga ccatggtgtc atagtccagc   6000
ccctccgcgg cgtggccctt ggcgcgcagc ttgcccttgg aggaggcgcc gcacgagggg   6060
cagtgcagac ttttgagggc gtagagcttg ggcgcgagaa ataccgattc cggggagtag   6120
gcatccgcgc cgcaggcccc gcagacggtc tcgcattcca cgagccaggt gagctctggc   6180
cgttcggggt caaaaaccag gtttccccca tgctttttga tgcgtttctt acctctggtt   6240
tccatgagcc ggtgtccacg ctcggtgacg aaaaggctgt ccgtgtcccc gtatacagac   6300
ttgagaggcc tgtcctcgag cggtgttccg cggtcctcct cgtatagaaa ctcggaccac   6360
tctgagacaa aggctcgcgt ccaggccagc acgaaggagg ctaagtggga ggggtagcgg   6420
tcgttgtcca ctagggggtc cactcgctcc agggtgtgaa gacacatgtc gccctcttcg   6480
gcatcaagga aggtgattgg tttgtaggtg taggccacgt gaccgggtgt tcctgaaggg   6540
gggctataaa agggggtggg ggcgcgttcg tcctcactct cttccgcatc gctgtctgcg   6600
agggccagct gttggggtga gtactccctc tgaaaagcgg gcatgacttc tgcgctaaga   6660
ttgtcagttt ccaaaaacga ggaggatttg atattcacct ggcccgcggt gatgcctttg   6720
agggtggccg catccatctg gtcagaaaag acaatctttt tgttgtcaag cttggtggca   6780
aacgacccgt agagggcgtt ggacagcaac ttggcgatgg agcgcagggt ttggtttttg   6840
tcgcgatcgg cgcgctcctt ggccgcgatg tttagctgca cgtattcgcg cgcaacgcac   6900
cgccattcgg gaaagacggt ggtgcgctcg tcgggcacca ggtgcacgcg ccaaccgcgg   6960
```

ttgtgcaggg tgacaaggtc aacgctggtg gctacctctc cgcgtaggcg ctcgttggtc 7020
cagcagaggc ggccgccctt gcgcgagcag aatggcggta gggggtctag ctgcgtctcg 7080
tccggggggt ctgcgtccac ggtaaagacc ccgggcagca ggcgcgcgtc gaagtagtct 7140
atcttgcatc cttgcaagtc tagcgcctgc tgccatgcgc gggcggcaag cgcgcgctcg 7200
tatgggttga gtgggggacc ccatggcatg gggtgggtga gcgcggaggc gtacatgccg 7260
caaatgtcgt aaacgtagag gggctctctg agtattccaa gatatgtagg gtagcatctt 7320
ccaccgcgga tgctggcgcg cacgtaatcg tatagttcgt gcgagggagc gaggaggtcg 7380
ggaccgaggt tgctacgggc gggctgctct gctcggaaga ctatctgcct gaagatggca 7440
tgtgagttgg atgatatggt tggacgctgg aagacgttga agctggcgtc tgtgagacct 7500
accgcgtcac gcacgaagga ggcgtaggag tcgcgcagct tgttgaccag ctcggcggtg 7560
acctgcacgt ctagggcgca gtagtccagg gtttccttga tgatgtcata cttatcctgt 7620
ccctttttt tccacagctc gcggttgagg acaaactctt cgcggtcttt ccagtactct 7680
tggatcggaa acccgtcggc ctccgaacgg taagagccta gcatgtagaa ctggttgacg 7740
gcctggtagg cgcagcatcc cttttctacg ggtagcgcgt atgcctgcgc ggccttccgg 7800
agcgaggtgt gggtgagcgc aaaggtgtcc ctgaccatga ctttgaggta ctggtatttg 7860
aagtcagtgt cgtcgcatcc gccctgctcc cagagcaaaa agtccgtgcg ctttttggaa 7920
cgcggatttg gcagggcgaa ggtgacatcg ttgaagagta tctttcccgc gcgaggcata 7980
aagttgcgtg tgatgcggaa gggtcccggc acctcggaac ggttgttaat tacctgggcg 8040
gcgagcacga tctcgtcaaa gccgttgatg ttgtggccca caatgtaaag ttccaagaag 8100
cgcgggatgc ccttgatgga aggcaatttt ttaagttcct cgtaggtgag ctcttcaggg 8160
gagctgagcc cgtgctctga aagggcccag tctgcaagat gagggttgga agcgacgaat 8220
gagctccaca ggtcacgggc cattagcatt tgcaggtggt cgcgaaaggt cctaaactgg 8280
cgacctatgg ccattttttc tggggtgatg cagtagaagg taagcgggtc ttgttcccag 8340
cggtcccatc caaggttcgc ggctaggtct cgcgcggcag tcactagagg ctcatctccg 8400
ccgaacttca tgaccagcat gaagggcacg agctgcttcc caaaggcccc catccaagta 8460
taggtctcta catcgtaggt gacaaagaga cgctcggtgc gaggatgcga gccgatcggg 8520
aagaactgga tctcccgcca ccaattggag gagtggctat tgatgtggtg aaagtagaag 8580
tccctgcgac gggccgaaca ctcgtgctgg cttttgtaaa aacgtgcgca gtactggcag 8640
cggtgcacgg gctgtacatc ctgcacgagg ttgacctgac gaccgcgcac aaggaagcag 8700
agtgggaatt tgagcccctc gcctggcggg tttggctggt ggtcttctac ttcggctgct 8760
tgtccttgac cgtctggctg ctcgagggga gttacggtgg atcggaccac cacgccgcgc 8820
gagcccaaag tccagatgtc cgcgcgcggc ggtcggagct tgatgacaac atcgcgcaga 8880
tgggagctgt ccatggtctg gagctcccgc ggcgtcaggt caggcgggag ctcctgcagg 8940
tttacctcgc atagacgggt cagggcgcgg gctagatcca ggtgatacct aatttccagg 9000
ggctggttgg tggcggcgtc gatggcttgc aagaggccgc atccccgcgg cgcgactacg 9060
gtaccgcgcg gcgggcggtg ggccgcgggg gtgtccttgg atgatgcatc taaaagcggt 9120
gacgcgggcg agcccccgga ggtagggggg gctccggacc cgccgggaga gggggcaggg 9180
gcacgtcggc gccgcgcgcg ggcaggagct ggtgctgcgc gcgtaggttg ctggcgaacg 9240
cgacgacgcg gcggttgatc tcctgaatct ggcgcctctg cgtgaagacg acgggcccgg 9300

```
tgagcttgaa cctgaaagag agttcgacag aatcaatttc ggtgtcgttg acggcggcct   9360
ggcgcaaaat ctcctgcacg tctcctgagt tgtcttgata ggcgatctcg gccatgaact   9420
gctcgatctc ttcctcctgg agatctccgc gtccggctcg ctccacggtg gcggcgaggt   9480
cgttggaaat gcgggccatg agctgcgaga aggcgttgag gcctccctcg ttccagacgc   9540
ggctgtagac cacgcccccct tcggcatcgc gggcgcgcat gaccacctgc gcgagattga   9600
gctccacgtg ccgggcgaag acggcgtagt ttcgcaggcg ctgaaagagg tagttgaggg   9660
tggtggcggt gtgttctgcc acgaagaagt acataaccca gcgtcgcaac gtggattcgt   9720
tgatatcccc caaggcctca aggcgctcca tggcctcgta gaagtccacg gcgaagttga   9780
aaaactggga gttgcgcgcc gacacggtta actcctcctc cagaagacgg atgagctcgg   9840
cgacagtgtc gcgcacctcg cgctcaaagg ctacaggggc ctcttcttct tcttcaatct   9900
cctcttccat aagggcctcc ccttcttctt cttctggcgg cggtggggga gggggggacac   9960
ggcggcgacg acggcgcacc gggaggcggt cgacaaagcg ctcgatcatc tccccgcggc  10020
gacggcgcat ggtctcggtg acggcgcggc cgttctcgcg gggcgcagt tggaagacgc  10080
cgcccgtcat gtcccggtta tgggttggcg gggggctgcc atgcggcagg gatacggcgc  10140
taacgatgca tctcaacaat tgttgtgtag gtactccgcc gccgagggac ctgagcgagt  10200
ccgcatcgac cggatcggaa aacctctcga gaaaggcgtc taaccagtca cagtcgcaag  10260
gtaggctgag caccgtggcg ggcggcagcg ggcggcggtc ggggttgttt ctggcggagg  10320
tgctgctgat gatgtaatta aagtaggcgg tcttgagacg gcggatggtc gacagaagca  10380
ccatgtcctt gggtccggcc tgctgaatgc gcaggcggtc ggccatgccc caggcttcgt  10440
tttgacatcg gcgcaggtct ttgtagtagt cttgcatgag cctttctacc ggcacttctt  10500
cttctccttc ctcttgtcct gcatctcttg catctatcgc tgcggcggcg gcggagtttg  10560
gccgtaggtg gcgccctctt cctcccatgc gtgtgacccc gaagcccctc atcggctgaa  10620
gcagggctag gtcggcgaca acgcgctcgg ctaatatggc ctgctgcacc tgcgtgaggg  10680
tagactggaa gtcatccatg tccacaaagc ggtggtatgc gcccgtgttg atggtgtaag  10740
tgcagttggc cataacggac cagttaacgg tctggtgacc cggctgcgag agctcggtgt  10800
acctgagacg cgagtaagcc ctcgagtcaa atacgtagtc gttgcaagtc cgcaccaggt  10860
actggtatcc caccaaaaag tgcggcggcg gctggcggta gaggggccag cgtagggtgg  10920
ccggggctcc gggggcgaga tcttccaaca taaggcgatg atatccgtag atgtacctgg  10980
acatccaggt gatgccggcg gcggtggtgg aggcgcgcgg aaagtcgcgg acgcggttcc  11040
agatgttgcg cagcggcaaa aagtgctcca tggtcgggac gctctggccg gtcaggcgcg  11100
cgcaatcgtt gacgctctag accgtgcaaa aggagagcct gtaagcgggc actcttccgt  11160
ggtctggtgg ataaattcgc aagggtatca tggcggacga ccggggttcg agccccgtat  11220
ccggccgtcc gccgtgatcc atgcggttac cgcccgcgtg tcgaacccag gtgtgcgacg  11280
tcagacaacg gggggagtgct ccttttggct tccttccagg cgcggcggct gctgcgctag  11340
ctttttggc cactggccgc gcgcagcgta agcggttagg ctggaaagcg aaagcattaa  11400
gtggctcgct ccctgtagcc ggagggttat tttccaaggg ttgagtcgcg ggaccccccgg  11460
ttcgagtctc ggaccggccg gactgcggcg aacgggggtt tgcctccccg tcatgcaaga  11520
ccccgcttgc aaattcctcc ggaaacaggg acgagcccct tttttgcttt tcccagatgc  11580
atccggtgct gcggcagatg cgccccccctc ctcagcagcg gcaagagcaa gagcagcggc  11640
agacatgcag ggcaccctcc cctcctccta ccgcgtcagg aggggcgaca tccgcggttg  11700
```

```
acgcggcagc agatggtgat tacgaacccc cgcggcgccg ggcccggcac tacctggact  11760
tggaggaggg cgagggcctg gcgcggctag gagcgccctc tcctgagcgg cacccaaggg  11820
tgcagctgaa gcgtgatacg cgtgaggcgt acgtgccgcg gcagaacctg tttcgcgacc  11880
gcgagggaga ggagcccgag gagatgcggg atcgaaagtt ccacgcaggg cgcgagctgc  11940
ggcatggcct gaatcgcgag cggttgctgc gcgaggagga ctttgagccc gacgcgcgaa  12000
ccgggattag tcccgcgcgc gcacacgtgg cggccgccga cctggtaacc gcatacgagc  12060
agacggtgaa ccaggagatt aactttcaaa aaagctttaa caaccacgtg cgtacgcttg  12120
tggcgcgcga ggaggtggct ataggactga tgcatctgtg ggactttgta agcgcgctgg  12180
agcaaaaccc aaatagcaag ccgctcatgg cgcagctgtt ccttatagtg cagcacagca  12240
gggacaacga ggcattcagg gatgcgctgc taaacatagt agagcccgag ggccgctggc  12300
tgctcgattt gataaacatc ctgcagagca tagtggtgca ggagcgcagc ttgagcctgg  12360
ctgacaaggt ggccgccatc aactattcca tgcttagcct gggcaagttt tacgcccgca  12420
agatatacca taccccttac gttcccatag acaaggaggt aaagatcgag gggttctaca  12480
tgcgcatggc gctgaaggtg cttaccttga gcgacgacct gggcgtttat cgcaacgagc  12540
gcatccacaa ggccgtgagc gtgagccggc ggcgcgagct cagcgaccgc gagctgatgc  12600
acagcctgca aagggccctg gctggcacgg gcagcggcga tagagaggcc gagtcctact  12660
ttgacgcggg cgctgacctg cgctgggccc caagccgacg cgccctggag gcagctgggg  12720
ccggacctgg gctggcggtg gcacccgcgc gcgctggcaa cgtcggcggc gtggaggaat  12780
atgacgagga cgatgagtac gagccagagg acggcgagta ctaagcggtg atgtttctga  12840
tcagatgatg caagacgcaa cggacccggc ggtgcgggcg gcgctgcaga gccagccgtc  12900
cggccttaac tccacggacg actggcgcca ggtcatggac cgcatcatgt cgctgactgc  12960
gcgcaatcct gacgcgttcc ggcagcagcc gcaggccaac cggctctccg caattctgga  13020
agcggtggtc ccggcgcgcg caaaccccac gcacgagaag gtgctggcga tcgtaaacgc  13080
gctggccgaa aacagggcca tccggcccga cgaggccggc ctggtctacg acgcgctgct  13140
tcagcgcgtg gctcgttaca acagcggcaa cgtgcagacc aacctggacc ggctggtggg  13200
ggatgtgcgc gaggccgtgg cgcagcgtga gcgcgcgcag cagcagggca acctgggctc  13260
catggttgca ctaaacgcct tcctgagtac acagcccgcc aacgtgccgc ggggacagga  13320
ggactacacc aactttgtga gcgcactgcg gctaatggtg actgagacac cgcaaagtga  13380
ggtgtaccag tctgggccag actatttttt ccagaccagt agacaaggcc tgcagaccgt  13440
aaacctgagc caggctttca aaaacttgca ggggctgtgg ggggtgcggg ctcccacagg  13500
cgaccgcgcg accgtgtcta gcttgctgac gcccaactcg cgcctgttgc tgctgctaat  13560
agcgcccttc acggacagtg gcagcgtgtc ccgggacaca tacctaggtc acttgctgac  13620
actgtaccgc gaggccatag gtcaggcgca tgtggacgag catactttcc aggagattac  13680
aagtgtcagc cgcgcgctgg ggcaggagga cacgggcagc ctggaggcaa ccctaaacta  13740
cctgctgacc aaccggcggc agaagatccc ctcgttgcac agtttaaaca gcgaggagga  13800
gcgcattttg cgctacgtgc agcagagcgt gagccttaac ctgatgcgcg acggggtaac  13860
gcccagcgtg gcgctggaca tgaccgcgcg caacatggaa ccgggcatgt atgcctcaaa  13920
ccggccgttt atcaaccgcc taatggacta cttgcatcgc gcggccgccg tgaaccccga  13980
gtatttcacc aatgccatct tgaacccgca ctggctaccg ccccctggtt tctacaccgg  14040
```

```
gggattcgag gtgcccgagg gtaacgatgg attcctctgg gacgacatag acgacagcgt  14100
gttttccccg caaccgcaga ccctgctaga gttgcaacag cgcgagcagg cagaggcggc  14160
gctgcgaaag gaaagcttcc gcaggccaag cagcttgtcc gatctaggcg ctgcggcccc  14220
gcggtcagat gctagtagcc catttccaag cttgataggg tctcttacca gcactcgcac  14280
cacccgcccg cgcctgctgg gcgaggagga gtacctaaac aactcgctgc tgcagccgca  14340
gcgcgaaaaa aacctgcctc cggcatttcc caacaacggg atagagagcc tagtggacaa  14400
gatgagtaga tggaagacgt acgcgcagga gcacagggac gtgccaggcc cgcgcccgcc  14460
cacccgtcgt caaaggcacg accgtcagcg gggtctggtg tgggaggacg atgactcggc  14520
agacgacagc agcgtcctgg atttgggagg gagtggcaac ccgtttgcgc accttcgccc  14580
caggctgggg agaatgtttt aaaaaaaaaa aaagcatgat gcaaaataaa aaactcacca  14640
aggccatggc accgagcgtt ggttttcttg tattcccctt agtatgcggc gcgcggcgat  14700
gtatgaggaa ggtcctcctc cctcctacga gagtgtggtg agcgcggcgc cagtggcggc  14760
ggcgctgggt tctcccttcg atgctcccct ggacccgccg tttgtgcctc cgcggtacct  14820
gcggcctacc ggggggagaa acagcatccg ttactctgag ttggcacccc tattcgacac  14880
cacccgtgtg tacctggtgg acaacaagtc aacggatgtg gcatccctga actaccagaa  14940
cgaccacagc aactttctga ccacggtcat tcaaaacaat gactacagcc cgggggaggc  15000
aagcacacag accatcaatc ttgacgaccg gtcgcactgg ggcggcgacc tgaaaaccat  15060
cctgcatacc aacatgccaa atgtgaacga gttcatgttt accaataagt ttaaggcgcg  15120
ggtgatggtg tcgcgcttgc ctactaagga caatcaggtg gagctgaaat acgagtgggt  15180
ggagttcacg ctgcccgagg gcaactactc cgagaccatg accatagacc ttatgaacaa  15240
cgcgatcgtg gagcactact tgaaagtggg cagacagaac ggggttctgg aaagcgacat  15300
cggggtaaag tttgacaccc gcaacttcag actggggttt gaccccgtca ctggtcttgt  15360
catgcctggg gtatatacaa acgaagcctt ccatccagac atcattttgc tgccaggatg  15420
cggggtggac ttcacccaca gccgcctgag caacttgttg ggcatccgca agcggcaacc  15480
cttccaggag ggctttagga tcacctacga tgatctggag ggtggtaaca ttcccgcact  15540
gttggatgtg gacgcctacc aggcgagctt gaaagatgac accgaacagg gcgggggtgg  15600
cgcaggcggc agcaacagca gtggcagcgg cgcggaagag aactccaacg cggcagccgc  15660
ggcaatgcag ccggtggagg acatgaacga tcatgccatt cgcggcgaca cctttgccac  15720
acgggctgag gagaagcgcg ctgaggccga agcagcggcc gaagctgccg cccccgctgc  15780
gcaacccgag gtcgagaagc ctcagaagaa accggtgatc aaacccctga cagaggacag  15840
caagaaacgc agttacaacc taataagcaa tgacagcacc ttcacccagt accgcagctg  15900
gtaccttgca tacaactacg gcgaccctca gaccggaatc cgctcatgga ccctgctttg  15960
cactcctgac gtaacctgcg gctcggagca ggtctactgg tcgttgccag acatgatgca  16020
agaccccgtg accttccgct ccacgcgcca gatcagcaac tttccggtgg tgggcgccga  16080
gctgttgccc gtgcactcca agagcttcta caacgaccag gccgtctact cccaactcat  16140
ccgccagttt acctctctga cccacgtgtt caatcgcttt cccgagaacc agattttggc  16200
gcgcccgcca gcccccacca tcaccaccgt cagtgaaaac gttcctgctc tcacagatca  16260
cgggacgcta ccgctgcgca acagcatcgg aggagtccag cgagtgacca ttactgacgc  16320
cagacgccgc acctgcccct acgtttacaa ggccctgggc atagtctcgc cgcgcgtcct  16380
atcgagccgc actttttgag caagcatgtc catccttata tcgcccagca ataacacagg  16440
```

```
ctggggcctg cgcttcccaa gcaagatgtt tggcggggcc aagaagcgct ccgaccaaca  16500
cccagtgcgc gtgcgcgggc actaccgcgc gccctggggc gcgcacaaac gcggccgcac  16560
tgggcgcacc accgtcgatg acgccatcga cgcggtggtg gaggaggcgc gcaactacac  16620
gcccacgccg ccaccagtgt ccacagtgga cgcggccatt cagaccgtgg tgcgcggagc  16680
ccggcgctat gctaaaatga agagacggcg gaggcgcgta gcacgtcgcc accgccgccg  16740
acccggcact gccgcccaac gcgcggcggc ggccctgctt aaccgcgcac gtcgcaccgg  16800
ccgacgggcg gccatgcggg ccgctcgaag gctggccgcg ggtattgtca ctgtgccccc  16860
caggtccagg cgacgagcgg ccgccgcagc agccgcggcc attagtgcta tgactcaggg  16920
tcgcaggggc aacgtgtatt gggtgcgcga ctcggttagc ggcctgcgcg tgcccgtgcg  16980
cacccgcccc ccgcgcaact agattgcaag aaaaaactac ttagactcgt actgttgtat  17040
gtatccagcg gcggcggcgc gcaacgaagc tatgtccaag cgcaaaatca aagaagagat  17100
gctccaggtc atcgcgccgg agatctatgg ccccccgaag aaggaagagc aggattacaa  17160
gccccgaaag ctaaagcggg tcaaaaagaa aaagaaagat gatgatgatg aacttgacga  17220
cgaggtggaa ctgctgcacg ctaccgcgcc caggcgacgg gtacagtgga aaggtcgacg  17280
cgtaaaacgt gttttgcgac ccggcaccac cgtagtcttt acgcccggtg agcgctccac  17340
ccgcacctac aagcgcgtgt atgatgaggt gtacggcgac gaggacctgc ttgagcaggc  17400
caacgagcgc ctcggggagt ttgcctacgg aaagcggcat aaggacatgc tggcgttgcc  17460
gctggacgag ggcaacccaa cacctagcct aaagcccgta acactgcagc aggtgctgcc  17520
cgcgcttgca ccgtccgaag aaaagcgcgg cctaaagcgc gagtctggtg acttggcacc  17580
caccgtgcag ctgatggtac ccaagcgcca gcgactggaa gatgtcttgg aaaaaatgac  17640
cgtggaacct gggctggagc ccgaggtccg cgtgcggcca atcaagcagg tggcgccggg  17700
actgggcgtg cagaccgtgg acgttcagat acccactacc agtagcacca gtattgccac  17760
cgccacagag ggcatggaga cacaaacgtc cccggttgcc tcagcggtgg cggatgccgc  17820
ggtgcaggcg gtcgctgcgg ccgcgtccaa gacctctacg gaggtgcaaa cggacccgtg  17880
gatgtttcgc gtttcagccc cccggcgccc gcgccgttcg aggaagtacg gcgccgccag  17940
cgcgctactg cccgaatatg ccctacatcc ttccattgcg cctacccccg gctatcgtgg  18000
ctacacctac cgccccagaa gacgagcaac tacccgacgc cgaaccacca ctggaacccg  18060
ccgccgccgt cgccgtcgcc agcccgtgct ggccccgatt tccgtgcgca gggtggctcg  18120
cgaaggaggc aggaccctgg tgctgccaac agcgcgctac caccccagca tcgtttaaaa  18180
gccggtcttt gtggttcttg cagatatggc cctcacctgc cgcctccgtt tcccggtgcc  18240
gggattccga ggaagaatgc accgtaggag gggcatggcc ggccacggcc tgacgggcgg  18300
catgcgtcgt gcgcaccacc ggcggcggcg cgcgtcgcac cgtcgcatgc gcggcggtat  18360
cctgcccctc cttattccac tgatcgccgc ggcgattggc gccgtgcccg gaattgcatc  18420
cgtggccttg caggcgcaga gacactgatt aaaaacaagt tgcatgtgga aaaatcaaaa  18480
taaaaagtct ggactctcac gctcgcttgg tcctgtaact attttgtaga atggaagaca  18540
tcaactttgc gtctctggcc ccgcgacacg gctcgcgccc gttcatggga aactggcaag  18600
atatcggcac cagcaatatg agcggtggcg ccttcagctg gggctcgctg tggagcggca  18660
ttaaaaattt cggttccacc gttaagaact atggcagcaa ggcctggaac agcagcacag  18720
gccagatgct gagggataag ttgaaagagc aaaatttcca acaaaaggtg gtagatggcc  18780
```

```
tggcctctgg cattagcggg gtggtggacc tggccaacca ggcagtgcaa aataagatta  18840
acagtaagct tgatccccgc cctcccgtag aggagcctcc accggccgtg gagacagtgt  18900
ctccagaggg gcgtggcgaa aagcgtccgc gccccgacag ggaagaaact ctggtgacgc  18960
aaatagacga gcctccctcg tacgaggagg cactaaagca aggcctgccc accacccgtc  19020
ccatcgcgcc catggctacc ggagtgctgg gccagcacac acccgtaacg ctggacctgc  19080
ctccccccgc cgacacccag cagaaacctg tgctgccagg cccgaccgcc gttgttgtaa  19140
cccgtcctag ccgcgcgtcc ctgcgccgcg ccgccagcgg tccgcgatcg ttgcggcccg  19200
tagccagtgg caactggcaa agcacactga acagcatcgt gggtctgggg gtgcaatccc  19260
tgaagcgccg acgatgcttc tgatagctaa cgtgtcgtat gtgtgtcatg tatgcgtcca  19320
tgtcgccgcc agaggagctg ctgagccgcc gcgcgcccgc tttccaagat ggctacccct  19380
tcgatgatgc cgcagtggtc ttacatgcac atctcgggcc aggacgcctc ggagtacctg  19440
agccccgggc tggtgcagtt tgcccgcgcc accgagacgt acttcagcct gaataacaag  19500
tttagaaacc ccacggtggc gcctacgcac gacgtgacca cagaccggtc ccagcgtttg  19560
acgctgcggt tcatccctgt ggaccgtgag gatactgcgt actcgtacaa ggcgcggttc  19620
accctagctg tgggtgataa ccgtgtgctg gacatggctt ccacgtactt tgacatccgc  19680
ggcgtgctgg acaggggccc tacttttaag ccctactctg gcactgccta caacgccctg  19740
gctcccaagg gtgccccaaa tccttgcgaa tgggatgaag ctgctactgc tcttgaaata  19800
aacctagaag aagaggacga tgacaacgaa gacgaagtag acgagcaagc tgagcagcaa  19860
aaaactcacg tatttgggca ggcgccttat tctggtataa atattacaaa ggagggtatt  19920
caaataggtg tcgaaggtca aacacctaaa tatgccgata aaacatttca acctgaacct  19980
caaataggag aatctcagtg gtacgaaaca gaaattaatc atgcagctgg gagagtccta  20040
aaaaagacta ccccaatgaa accatgttac ggttcatatg caaaacccac aaatgaaaat  20100
ggagggcaag gcattcttgt aaagcaacaa aatggaaagc tagaaagtca agtggaaatg  20160
caatttttct caactactga ggcagccgca ggcaatggtg ataacttgac tcctaaagtg  20220
gtattgtaca gtgaagatgt agatatagaa accccagaca ctcatatttc ttacatgccc  20280
actattaagg aaggtaactc acgagaacta atgggccaac aatctatgcc caacaggcct  20340
aattacattg cttttaggga caattttatt ggtctaatgt attacaacag cacgggtaat  20400
atgggtgttc tggcgggcca agcatcgcag ttgaatgctg ttgtagattt gcaagacaga  20460
aacacagagc tttcatacca gcttttgctt gattccattg gtgatagaac caggtacttt  20520
tctatgtgga atcaggctgt tgacagctat gatccagatg ttagaattat tgaaaatcat  20580
ggaactgaag atgaacttcc aaattactgc tttccactgg gaggtgtgat taatacagag  20640
actcttacca aggtaaaacc taaaacaggt caggaaaatg gatgggaaaa agatgctaca  20700
gaattttcag ataaaaatga aataagagtt ggaaataatt ttgccatgga aatcaatcta  20760
aatgccaacc tgtggagaaa tttcctgtac tccaacatag cgctgtattt gcccgacaag  20820
ctaaagtaca gtccttccaa cgtaaaaatt tctgataacc caaacaccta cgactacatg  20880
aacaagcgag tggtggctcc cgggctagtg gactgctaca ttaaccttgg agcacgctgg  20940
tcccttgact atatggacaa cgtcaaccca tttaaccacc accgcaatgc tggcctgcgc  21000
taccgctcaa tgttgctggg caatggtcgc tatgtgccct tccacatcca ggtgcctcag  21060
aagttctttg ccattaaaaa cctccttctc ctgccgggct catacaccta cgagtggaac  21120
ttcaggaagg atgttaacat ggttctgcag agctccctag gaaatgacct aagggttgac  21180
```

```
ggagccagca ttaagtttga tagcatttgc ctttacgcca ccttcttccc catggcccac  21240
aacaccgcct ccacgcttga ggccatgctt agaaacgaca ccaacgacca gtcctttaac  21300
gactatctct ccgccgccaa catgctctac cctatacccg ccaacgctac caacgtgccc  21360
atatccatcc cctcccgcaa ctgggcggct ttccgcggct gggccttcac gcgccttaag  21420
actaaggaaa ccccatcact gggctcgggc tacgaccctt attacaccta ctctggctct  21480
ataccctacc tagatggaac cttttacctc aaccacacct ttaagaaggt ggccattacc  21540
tttgactctt ctgtcagctg gcctggcaat gaccgcctgc ttacccccaa cgagtttgaa  21600
attaagcgct cagttgacgg ggagggttac aacgttgccc agtgtaacat gaccaaagac  21660
tggttcctgg tacaaatgct agctaactat aacattggct accagggctt ctatatccca  21720
gagagctaca aggaccgcat gtactccttc tttagaaact tccagcccat gagccgtcag  21780
gtggtggatg atactaaata caaggactac caacaggtgg gcatcctaca ccaacacaac  21840
aactctggat ttgttggcta ccttgccccc accatgcgcg aaggacaggc ctaccctgct  21900
aacttcccct atccgcttat aggcaagacc gcagttgaca gcattaccca gaaaaagttt  21960
ctttgcgatc gcaccctttg gcgcatccca ttctccagta actttatgtc catgggcgca  22020
ctcacagacc tgggccaaaa ccttctctac gccaactccg cccacgcgct agacatgact  22080
tttgaggtgg atcccatgga cgagcccacc cttctttatg ttttgtttga agtctttgac  22140
gtggtccgtg tgcaccagcc gcaccgcggc gtcatcgaaa ccgtgtacct gcgcacgccc  22200
ttctcggccg gcaacgccac aacataaaga agcaagcaac atcaacaaca gctgccgcca  22260
tgggctccag tgagcaggaa ctgaaagcca ttgtcaaaga tcttggttgt gggccatatt  22320
ttttgggcac ctatgacaag cgctttccag gctttgtttc tccacacaag ctcgcctgcg  22380
ccatagtcaa tacggccggt cgcgagactg ggggcgtaca ctggatggcc tttgcctgga  22440
acccgcactc aaaaacatgc tacctctttg agccctttgg cttttctgac cagcgactca  22500
agcaggttta ccagtttgag tacgagtcac tcctgcgccg tagcgccatt gcttcttccc  22560
ccgaccgctg tataacgctg gaaaagtcca cccaaagcgt acaggggccc aactcggccg  22620
cctgtggact attctgctgc atgtttctcc acgcctttgc caactggccc caaactccca  22680
tggatcacaa ccccaccatg aaccttatta ccggggtacc caactccatg ctcaacagtc  22740
cccaggtaca gcccaccctg cgtcgcaacc aggaacagct ctacagcttc ctggagcgcc  22800
actcgcccta cttccgcagc cacagtgcgc agattaggag cgccacttct ttttgtcact  22860
tgaaaaacat gtaaaaataa tgtactagag acactttcaa taaaggcaaa tgcttttatt  22920
tgtacactct cgggtgatta tttaccccca cccttgccgt ctgcgccgtt taaaaatcaa  22980
aggggttctg ccgcgcatcg ctatgcgcca ctggcaggga cacgttgcga tactggtgtt  23040
tagtgctcca cttaaactca ggcacaacca tccgcggcag ctcggtgaag ttttcactcc  23100
acaggctgcg caccatcacc aacgcgttta gcaggtcggg cgccgatatc ttgaagtcgc  23160
agttggggcc tccgccctgc gcgcgcgagt tgcgatacac agggttgcag cactggaaca  23220
ctatcagcgc cgggtggtgc acgctggcca gcacgctctt gtcggagatc agatccgcgt  23280
ccaggtcctc cgcgttgctc agggcgaacg gagtcaactt tggtagctgc cttcccaaaa  23340
agggcgcgtg cccaggcttt gagttgcact cgcaccgtag tggcatcaaa aggtgaccgt  23400
gcccggtctg ggcgttagga tacagcgcct gcataaaagc cttgatctgc ttaaaagcca  23460
cctgagcctt tgcgccttca gagaagaaca tgccgcaaga cttgccggaa aactgattgg  23520
```

```
ccggacaggc cgcgtcgtgc acgcagcacc ttgcgtcggt gttggagatc tgcaccacat  23580
ttcggcccca ccggttcttc acgatcttgg ccttgctaga ctgctccttc agcgcgcgct  23640
gcccgttttc gctcgtcaca tccatttcaa tcacgtgctc cttatttatc ataatgcttc  23700
cgtgtagaca cttaagctcg ccttcgatct cagcgcagcg gtgcagccac aacgcgcagc  23760
ccgtgggctc gtgatgcttg taggtcacct ctgcaaacga ctgcaggtac gcctgcagga  23820
atcgccccat catcgtcaca aaggtcttgt tgctggtgaa ggtcagctgc aacccgcggt  23880
gctcctcgtt cagccaggtc ttgcatacgg ccgccagagc ttccacttgg tcaggcagta  23940
gtttgaagtt cgcctttaga tcgttatcca cgtggtactt gtccatcagc gcgcgcgcag  24000
cctccatgcc cttctcccac gcagacacga tcggcacact cagcgggttc atcaccgtaa  24060
tttcactttc cgcttcgctg ggctcttcct cttcctcttg cgtccgcata ccacgcgcca  24120
ctgggtcgtc ttcattcagc cgccgcactg tgcgcttacc tcctttgcca tgcttgatta  24180
gcaccggtgg gttgctgaaa cccaccattt gtagcgccac atcttctctt tcttcctcgc  24240
tgtccacgat tacctctggt gatggcgggc gctcgggctt gggagaaggg cgcttctttt  24300
tcttcttggg cgcaatggcc aaatccgccg ccgaggtcga tggccgcggg ctgggtgtgc  24360
gcggcaccag cgcgtcttgt gatgagtctt cctcgtcctc ggactcgata cgccgcctca  24420
tccgcttttt tgggggcgcc cggggaggcg gcggcgacgg ggacggggac gacacgtcct  24480
ccatggttgg gggacgtcgc gccgcaccgc gtccgcgctc gggggtggtt tcgcgctgct  24540
cctcttcccg actggccatt tccttctcct ataggcagaa aaagatcatg gagtcagtcg  24600
agaagaagga cagcctaacc gccccctctg agttcgccac caccgcctcc accgatgccg  24660
ccaacgcgcc taccaccttc cccgtcgagg cacccccgct tgaggaggag gaagtgatta  24720
tcgagcagga cccaggtttt gtaagcgaag acgacgagga ccgctcagta ccaacagagg  24780
ataaaaagca agaccaggac aacgcagagg caaacgagga acaagtcggg cggggggacg  24840
aaaggcatgg cgactaccta gatgtgggag acgacgtgct gttgaagcat ctgcagcgcc  24900
agtgcgccat tatctgcgac gcgttgcaag agcgcagcga tgtgcccctc gccatagcgg  24960
atgtcagcct tgcctacgaa cgccacctat tctcaccgcg cgtacccccc aaacgccaag  25020
aaaacggcac atgcgagccc aacccgcgcc tcaacttcta ccccgtattt gccgtgccag  25080
aggtgcttgc cacctatcac atctttttcc aaaactgcaa gataccccta tcctgccgtg  25140
ccaaccgcag ccgagcggac aagcagctgg ccttgcggca gggcgctgtc atacctgata  25200
tcgcctcgct caacgaagtg ccaaaaatct ttgagggtct tggacgcgac gagaagcgcg  25260
cggcaaacgc tctgcaacag gaaaacagcg aaaatgaaag tcactctgga gtgttggtgg  25320
aactcgaggg tgacaacgcg cgcctagccg tactaaaacg cagcatcgag gtcacccact  25380
ttgcctaccc ggcacttaac ctacccccca aggtcatgag cacagtcatg agtgagctga  25440
tcgtgcgccg tgcgcagccc ctggagaggg atgcaaattt gcaagaacaa acagaggagg  25500
gcctacccgc agttggcgac gagcagctag cgcgctggct tcaaacgcgc gagcctgccg  25560
acttggagga gcgacgcaaa ctaatgatgg ccgcagtgct cgttaccgtg gagcttgagt  25620
gcatgcagcg gttctttgct gacccggaga tgcagcgcaa gctagaggaa acattgcact  25680
acacctttcg acagggctac gtacgccagg cctgcaagat ctccaacgtg gagctctgca  25740
acctggtctc ctaccttgga attttgcacg aaaaccgcct tgggcaaaac gtgcttcatt  25800
ccacgctcaa gggcgaggcg cgccgcgact acgtccgcga ctgcgtttac ttatttctat  25860
gctacacctg gcagacggcc atgggcgttt ggcagcagtg cttggaggag tgcaacctca  25920
```

```
aggagctgca gaaactgcta aagcaaaact tgaaggacct atggacggcc ttcaacgagc  25980
gctccgtggc cgcgcacctg gcggacatca ttttccccga acgcctgctt aaaaccctgc  26040
aacagggtct gccagacttc accagtcaaa gcatgttgca gaactttagg aactttatcc  26100
tagagcgctc aggaatcttg cccgccacct gctgtgcact tcctagcgac tttgtgccca  26160
ttaagtaccg cgaatgccct ccgccgcttt ggggccactg ctaccttctg cagctagcca  26220
actaccttgc ctaccactct gacataatgg aagacgtgag cggtgacggt ctactggagt  26280
gtcactgtcg ctgcaaccta tgcaccccgc accgctccct ggtttgcaat tcgcagctgc  26340
ttaacgaaag tcaaattatc ggtacctttg agctgcaggg tccctcgcct gacgaaaagt  26400
ccgcggctcc ggggttgaaa ctcactccgg ggctgtggac gtcggcttac cttcgcaaat  26460
ttgtacctga ggactaccac gcccacgaga ttaggttcta cgaagaccaa tcccgcccgc  26520
ctaatgcgga gcttaccgcc tgcgtcatta cccagggcca cattcttggc caattgcaag  26580
ccatcaacaa agcccgccaa gagtttctgc tacgaaaggg acgggggtt tacttggacc  26640
cccagtccgg cgaggagctc aacccaatcc ccccgccgcc gcagccctat cagcagcagc  26700
cgcgggccct tgcttcccag gatggcaccc aaaaagaagc tgcagctgcc gccgccaccc  26760
acggacgagg aggaatactg ggacagtcag gcagaggagg ttttggacga ggaggaggag  26820
gacatgatgg aagactggga gagcctagac gaggaagctt ccgaggtcga agaggtgtca  26880
gacgaaacac cgtcaccctc ggtcgcattc ccctcgccgg cgccccagaa atcggcaacc  26940
ggttccagca tggctacaac ctccgctcct caggcgccgc cggcactgcc cgttcgccga  27000
cccaaccgta gatgggacac cactggaacc agggccggta agtccaagca gccgccgccg  27060
ttagcccaag agcaacaaca gcgccaaggc taccgctcat ggcgcgggca caagaacgcc  27120
atagttgctt gcttgcaaga ctgtgggggc aacatctcct tcgcccgccg ctttcttctc  27180
taccatcacg gcgtggcctt cccccgtaac atcctgcatt actaccgtca tctctacagc  27240
ccatactgca ccggcggcag cggcagcaac agcagcggcc acacagaagc aaaggcgacc  27300
ggatagcaag actctgacaa agcccaagaa atccacagcg gcggcagcag caggaggagg  27360
agcgctgcgt ctggcgccca acgaacccgt atcgacccgc gagcttagaa acaggatttt  27420
tcccactctg tatgctatat ttcaacagag caggggccaa gaacaagagc tgaaaataaa  27480
aaacaggtct ctgcgatccc tcacccgcag ctgcctgtat cacaaaagcg aagatcagct  27540
tcggcgcacg ctggaagacg cggaggctct cttcagtaaa tactgcgcgc tgactcttaa  27600
ggactagttt cgcgcccttt ctcaaattta agcgcgaaaa ctacgtcatc tccagcggcc  27660
acacccggcg ccagcacctg ttgtcagcgc cattatgagc aaggaaattc ccacgcccta  27720
catgtggagt taccagccac aaatgggact tgcggctgga gctgcccaag actactcaac  27780
ccgaataaac tacatgagcg cgggacccca catgatatcc cgggtcaacg gaatacgcgc  27840
ccaccgaaac cgaattctcc tggaacaggc ggctattacc accacacctc gtaataacct  27900
taatccccgt agttggcccg ctgccctggt gtaccaggaa agtcccgctc ccaccactgt  27960
ggtacttccc agagacgccc aggccgaagt tcagatgact aactcagggg cgcagcttgc  28020
gggcggcttt cgtcacaggg tgcggtcgcc cgggcagggt ataactcacc tgacaatcag  28080
agggcgaggt attcagctca acgacgagtc ggtgagctcc tcgcttggtc tccgtccgga  28140
cgggacattt cagatcggcg gcgccggccg ctcttcattc acgcctcgtc aggcaatcct  28200
aactctgcag acctcgtcct ctgagccgcg ctctggaggc attggaactc tgcaatttat  28260
```

```
tgaggagttt gtgccatcgg tctactttaa ccccttctcg ggacctcccg gccactatcc  28320
ggatcaattt attcctaact ttgacgcggt aaaggactcg gcggacggct acgactgaat  28380
gttaagtgga gaggcagagc aactgcgcct gaaacacctg gtccactgtc gccgccacaa  28440
gtgctttgcc cgcgactccg gtgagttttg ctactttgaa ttgcccgagg atcatatcga  28500
gggcccggcg cacggcgtcc ggcttaccgc ccagggagag cttgcccgta gcctgattcg  28560
ggagtttacc cagcgccccc tgctagttga gcgggacagg ggaccctgtg ttctcactgt  28620
gatttgcaac tgtcctaacc ctggattaca tcaagatctt tgttgccatc tctgtgctga  28680
gtataataaa tacagaaatt aaaatatact ggggctccta tcgccatcct gtaaacgcca  28740
ccgtcttcac ccgcccaagc aaaccaaggc gaaccttacc tggtactttt aacatctctc  28800
cctctgtgat ttacaacagt ttcaacccag acggagtgag tctacgagag aacctctccg  28860
agctcagcta ctccatcaga aaaaacacca ccctccttac ctgccgggaa cgtacgagtg  28920
cgtcaccggc cgctgcacca cacctaccgc ctgaccgtaa accagacttt ttccggacag  28980
acctcaataa ctctgtttac cagaacagga ggtgagctta gaaaaccctt agggtattag  29040
gccaaaggcg cagctactgt ggggtttatg aacaattcaa gcaactctac gggctattct  29100
aattcaggtt tctctagaat cggggttggg gttattctct gtcttgtgat tctctttatt  29160
cttatactaa cgcttctctg cctaaggctc gccgcctgct gtgtgcacat ttgcatttat  29220
tgtcagcttt ttaaacgctg gggtcgccac ccaagatgat taggtacata atcctaggtt  29280
tactcaccct tgcgtcagcc cacggtacca cccaaaaggt ggattttaag gagccagcct  29340
gtaatgttac attcgcagct gaagctaatg agtgcaccac tcttataaaa tgcaccacag  29400
aacatgaaaa gctgcttatt cgccacaaaa acaaaattgg caagtatgct gtttatgcta  29460
tttggcagcc aggtgacact acagagtata atgttacagt tttccagggt aaaagtcata  29520
aaacttttat gtatactttt ccattttatg aaatgtgcga cattaccatg tacatgagca  29580
aacagtataa gttgtggccc ccacaaaatt gtgtggaaaa cactggcact ttctgctgca  29640
ctgctatgct aattacagtg ctcgctttgg tctgtaccct actctatatt aaatacaaaa  29700
gcagacgcag ctttattgag gaaaagaaaa tgccttaatt tactaagtta caaagctaat  29760
gtcaccacta actgctttac tcgctgcttg caaaacaaat tcaaaaagtt agcattataa  29820
ttagaatagg atttaaaccc cccggtcatt tcctgctcaa taccattccc ctgaacaatt  29880
gactctatgt gggatatgct ccagcgctac aaccttgaag tcaggcttcc tggatgtcag  29940
catctgactt tggccagcac ctgtcccgcg gatttgttcc agtccaacta cagcgaccca  30000
ccctaacaga gatgaccaac acaaccaacg cggccgccgc taccggactt acatctacca  30060
caaatacacc ccaagtttct gcctttgtca ataactggga taacttgggc atgtggtggt  30120
tctccatagc gcttatgttt gtatgcctta ttattatgtg gctcatctgc tgcctaaagc  30180
gcaaacgcgc ccgaccaccc atctatagtc ccatcattgt gctacaccca aacaatgatg  30240
gaatccatag attggacgga ctgaaacaca tgttcttttc tcttacagta tgattaaatg  30300
agacatgatt cctcgagttt ttatattact gacccttgtt gcgctttttt tgtgcgtgct  30360
ccacattggc tgcggtttct cacatcgaag tagactgcat tccagccttc acagtctatt  30420
tgctttacgg atttgtcacc ctcacgctca tctgcagcct catcactgtg gtcatcgcct  30480
ttatccagtg cattgactgg gtctgtgtgc gctttgcata tctcagacac catccccagt  30540
acagggacag gactatagct gagcttctta gaattcttta attatgaaat ttactgtgac  30600
ttttctgctg attatttgca ccctatctgc gttttgttcc ccgacctcca agcctcaaag  30660
```

```
acatatatca tgcagattca ctcgtatatg gaatattcca agttgctaca atgaaaaaag  30720
cgatctttcc gaagcctggt tatatgcaat catctctgtt atggtgttct gcagtaccat  30780
cttagcccta gctatatatc cctaccttga cattggctgg aacgcaatag atgccatgaa  30840
ccacccaact ttccccgcgc ccgctatgct tccactgcaa caagttgttg ccggcggctt  30900
tgtcccagcc aatcagcctc gcccaccttc tcccaccccc actgaaatca gctactttaa  30960
tctaacagga ggagatgact gacaccctag atctagaaat ggacggaatt attacagagc  31020
agcgcctgct agaaagacgc agggcagcgg ccgagcaaca gcgcatgaat caagagctcc  31080
aagacatggt taacttgcac cagtgcaaaa ggggtatctt ttgtctggta aagcaggcca  31140
aagtcaccta cgacagtaat accaccggac accgccttag ctacaagttg ccaaccaagc  31200
gtcagaaatt ggtggtcatg gtgggagaaa agcccattac cataactcag cactcggtag  31260
aaaccgaagg ctgcattcac tcaccttgtc aaggacctga ggatctctgc acccttatta  31320
agaccctgtg cggtctcaaa gatcttattc cctttaacta ataaaaaaaa ataataaagc  31380
atcacttact taaaatcagt tagcaaattt ctgtccagtt tattcagcag cacctccttg  31440
ccctcctccc agctctggta ttgcagcttc ctcctggctg caaactttct ccacaatcta  31500
aatggaatgt cagtttcctc ctgttcctgt ccatccgcac ccactatctt catgttgttg  31560
cagatgaagc gcgcaagacc gtctgaagat accttcaacc ccgtgtatcc atatgacacg  31620
gaaaccggtc ctccaactgt gccttttctt actcctccct ttgtatcccc caatgggttt  31680
caagagagtc cccctggggt actctctttg cgcctatccg aacctctagt tacctccaat  31740
ggcatgcttg cgctcaaaat gggcaacggc ctctctctgg acgaggccgg caaccttacc  31800
tcccaaaatg taaccactgt gagcccacct ctcaaaaaaa ccaagtcaaa cataaacctg  31860
gaaatatctg cacccctcac agttacctca gaagccctaa ctgtggctgc cgccgcacct  31920
ctaatggtcg cgggcaacac actcaccatg caatcacagg ccccgctaac cgtgcacgac  31980
tccaaactta gcattgccac ccaaggaccc ctcacagtgt cagaaggaaa gctagccctg  32040
caaacatcag gccccctcac caccaccgat agcagtaccc ttactatcac tgcctcaccc  32100
cctctaacta ctgccactgg tagcttgggc attgacttga aagagcccat ttatacacaa  32160
aatggaaaac taggactaaa gtacggggct cctttgcatg taacagacga cctaaacact  32220
ttgaccgtag caactggtcc aggtgtgact attaataata cttccttgca aactaaagtt  32280
actggagcct tgggttttga ttcacaaggc aatatgcaac ttaatgtagc aggaggacta  32340
aggattgatt ctcaaaacag acgccttata cttgatgtta gttatccgtt tgatgctcaa  32400
aaccaactaa atctaagact aggacagggc cctcttttta taaactcagc ccacaacttg  32460
gatattaact acaacaaagg cctttacttg tttacagctt caaacaattc caaaaagctt  32520
gaggttaacc taagcactgc caaggggttg atgtttgacg ctacagccat agccattaat  32580
gcaggagatg ggcttgaatt tggttcacct aatgcaccaa acacaaatcc cctcaaaaca  32640
aaaattggcc atggcctaga atttgattca aacaaggcta tggttcctaa actaggaact  32700
ggccttagtt ttgacagcac aggtgccatt acagtaggaa acaaaaataa tgataagcta  32760
actttgtgga ccacaccagc tccatctcct aactgtagac taaatgcaga gaaagatgct  32820
aaactcactt tggtcttaac aaaatgtggc agtcaaatac ttgctacagt ttcagttttg  32880
gctgttaaag gcagtttggc tccaatatct ggaacagttc aaagtgctca tcttattata  32940
agatttgacg aaaatggagt gctactaaac aattccttcc tggacccaga atattggaac  33000
```

```
tttagaaatg gagatcttac tgaaggcaca gcctatacaa acgctgttgg atttatgcct  33060
aacctatcag cttatccaaa atctcacggt aaaactgcca aaagtaacat tgtcagtcaa  33120
gtttacttaa acggagacaa aactaaacct gtaacactaa ccattacact aaacggtaca  33180
caggaaacag gagacacaac tccaagtgca tactctatgt cattttcatg gactggtct   33240
ggccacaact acattaatga aatatttgcc acatcctctt acactttttc atacattgcc  33300
caagaataaa gaatcgtttg tgttatgttt caacgtgttt atttttcaat tgcagaaaat  33360
ttcaagtcat ttttcattca gtagtatagc cccaccacca catagcttat acagatcacc  33420
gtaccttaat caaactcaca gaaccctagt attcaacctg ccacctccct cccaacacac  33480
agagtacaca gtcctttctc cccggctggc cttaaaaagc atcatatcat gggtaacaga  33540
catattctta ggtgttatat tccacacggt ttcctgtcga gccaaacgct catcagtgat  33600
attaataaac tccccgggca gctcacttaa gttcatgtcg ctgtccagct gctgagccac  33660
aggctgctgt ccaacttgcg gttgcttaac gggcggcgaa ggagaagtcc acgcctacat  33720
gggggtagag tcataatcgt gcatcaggat agggcggtgg tgctgcagca gcgcgcgaat  33780
aaactgctgc cgccgccgct ccgtcctgca ggaatacaac atggcagtgg tctcctcagc  33840
gatgattcgc accgcccgca gcataaggcg ccttgtcctc cgggcacagc agcgcaccct  33900
gatctcactt aaatcagcac agtaactgca gcacagcacc acaatattgt tcaaaatccc  33960
acagtgcaag gcgctgtatc caaagctcat ggcggggacc acagaaccca cgtggccatc  34020
ataccacaag cgcaggtaga ttaagtggcg acccctcata aacacgctgg acataaacat  34080
tacctctttt ggcatgttgt aattcaccac ctcccggtac catataaacc tctgattaaa  34140
catggcgcca tccaccacca tcctaaacca gctggccaaa acctgcccgc cggctataca  34200
ctgcagggaa ccgggactgg aacaatgaca gtggagagcc caggactcgt aaccatggat  34260
catcatgctc gtcatgatat caatgttggc acaacacagg cacacgtgca tacacttcct  34320
caggattaca agctcctccc gcgttagaac catatcccag ggaacaaccc attcctgaat  34380
cagcgtaaat cccacactgc agggaagacc tcgcacgtaa ctcacgttgt gcattgtcaa  34440
agtgttacat tcgggcagca gcggatgatc ctccagtatg gtagcgcggg tttctgtctc  34500
aaaaggaggt agacgatccc tactgtacgg agtgcgccga gacaaccgag atcgtgttgg  34560
tcgtagtgtc atgccaaatg gaacgccgga cgtagtcata tttcctgaag caaaaccagg  34620
tgcgggcgtg acaaacagat ctgcgtctcc ggtctcgccg cttagatcgc tctgtgtagt  34680
agttgtagta tatccactct ctcaaagcat ccaggcgccc cctggcttcg ggttctatgt  34740
aaactccttc atgcgccgct gccctgataa catccaccac cgcagaataa gccacaccca  34800
gccaacctac acattcgttc tgcgagtcac acacgggagg agcgggaaga gctggaagaa  34860
ccatgttttt ttttttattc caaaagatta tccaaaacct caaaatgaag atctattaag  34920
tgaacgcgct cccctccggt ggcgtggtca aactctacag ccaaagaaca gataatggca  34980
tttgtaagat gttgcacaat ggcttccaaa aggcaaacgg ccctcacgtc caagtggacg  35040
taaaggctaa acccttcagg gtgaatctcc tctataaaca ttccagcacc ttcaaccatg  35100
cccaaataat tctcatctcg ccaccttctc aatatatctc taagcaaatc ccgaatatta  35160
agtccggcca ttgtaaaaat ctgctccaga gcgccctcca ccttcagcct caagcagcga  35220
atcatgattg caaaaattca ggttcctcac agacctgtat aagattcaaa agcggaacat  35280
taacaaaaat accgcgatcc cgtaggtccc ttcgcagggc cagctgaaca taatcgtgca  35340
ggtctgcacg gaccagcgcg gccacttccc cgccaggaac catgacaaaa gaacccacac  35400
```

```
tgattatgac acgcatactc ggagctatgc taaccagcgt agccccgatg taagcttgtt  35460

gcatgggcgg cgatataaaa tgcaaggtgc tgctcaaaaa atcaggcaaa gcctcgcgca  35520

aaaaagaaag cacatcgtag tcatgctcat gcagataaag gcaggtaagc tccggaacca  35580

ccacagaaaa agacaccatt tttctctcaa acatgtctgc gggtttctgc ataaacacaa  35640

aataaaataa caaaaaaaca tttaaacatt agaagcctgt cttacaacag gaaaaacaac  35700

ccttataagc ataagacgga ctacggccat gccggcgtga ccgtaaaaaa actggtcacc  35760

gtgattaaaa agcaccaccg acagctcctc ggtcatgtcc ggagtcataa tgtaagactc  35820

ggtaaacaca tcaggttgat tcacatcggt cagtgctaaa aagcgaccga aatagcccgg  35880

gggaatacat acccgcaggc gtagagacaa cattacagcc cccataggag gtataacaaa  35940

attaatagga gagaaaaaca cataaacacc tgaaaaaccc tcctgcctag gcaaaatagc  36000

accctcccgc tccagaacaa catacagcgc ttccacagcg gcagccataa cagtcagcct  36060

taccagtaaa aaagaaaacc tattaaaaaa acaccactcg acacggcacc agctcaatca  36120

gtcacagtgt aaaaaagggc caagtgcaga gcgagtatat ataggactaa aaaatgacgt  36180

aacggttaaa gtccacaaaa aacacccaga aaaccgcacg cgaacctacg cccagaaacg  36240

aaagccaaaa aacccacaac ttcctcaaat cgtcacttcc gttttcccac gttacgtcac  36300

ttcccatttt aagaaaaacta caattcccaa cacatacaag ttactccgcc ctaaaaccta  36360

cgtcacccgc cccgttccca cgccccgcgc cacgtcacaa actccacccc ctcattatca  36420

tattggcttc aatccaaaat aaggtatatt attgatgatg                        36460
```

```
<210> SEQ ID NO 10
<211> LENGTH: 35203
<212> TYPE: DNA
<213> ORGANISM: Artificial sequence
<220> FEATURE:
<223> OTHER INFORMATION: PPE-1-3X-FasC virl construct (lacking repeats)
<220> FEATURE:
<221> NAME/KEY: misc_feature
<222> LOCATION: (460)..(1437)
<223> OTHER INFORMATION: A modified murine pre-proendothelin-1 promoter
      (PPE-1-3X)
<220> FEATURE:
<221> NAME/KEY: misc_feature
<222> LOCATION: (1438)..(1468)
<223> OTHER INFORMATION: Linker
<220> FEATURE:
<221> NAME/KEY: misc_feature
<222> LOCATION: (1469)..(2058)
<223> OTHER INFORMATION: TNFR portion of the Fas-TNFR-1 chimera (Fas-c)
<220> FEATURE:
<221> NAME/KEY: misc_feature
<222> LOCATION: (2059)..(2569)
<223> OTHER INFORMATION: FAS portion of the Fas-TNFR-1 chimera (Fas-c)

<400> SEQUENCE: 10

catcatcaat aatatacctt attttggatt gaagccaata tgataatgag gggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagtacgta cgtgtacttc tgatcggcga    480
```

```
tactagggag ataaggatgt acctgacaaa accacattgt tgttgttatc attattattt    540
agttttcctt ccttgctaac tcctgacgga atctttctca cctcaaatgc gaagtacttt    600
agtttagaaa agacttggtg gaaggggtgg tggtggaaaa gtagggtgat cttccaaact    660
aatctggttc cccgcccgcc ccagtagctg ggattcaaga gcgaagagtg ggatcgtcc     720
ccttgtttga tcagaaagac ataaaaggaa aatcaagtga acaatgatca gccccacctc    780
caccccaccc ccctgcgcgc gcacaataca atctatttaa ttgtacttca tacttttcat    840
tccaatgggg tgactttgct tctggagaaa ctcttgattc ttgaactctg gggctggcag    900
ctagcctcca gaagcaaagt caccccattg gaatgaaaag tatgaagtac aatgaaaagt    960
atgaagtact ggctccagaa gcaaagtcac cctccagaag caaagtcacc ccattggaat   1020
gaaaagtatg aagtacgcta gcaaaagggg aagcgggctg ctgctctctg caggttctgc   1080
agcggtctct gtctagtggg tgttttcttt ttcttagccc tgcccctgga ttgtcagacg   1140
gcgggcgtct gcctctgaag ttagccgtga tttcctctag agccgggtct tatctctggc   1200
tgcacgttgc ctgtgggtga ctaatcacac aataacattg tttagggctg gaataaagtc   1260
agagctgttt acccccactc tataggggtt caatataaaa aggcggcgga gaactgtccg   1320
agtcagaagc gttcctgcac cggcgctgag agcctgaccc ggtctgctcc gctgtccttg   1380
cgcgctgcct cccggctgcc cgcgacgctt tcgccccagt ggaagggcca cttgctgcgg   1440
ccgctaattc tgcagatcgg gatccggcat gggcctctcc accgtgcctg acctgctgct   1500
gccgctggtg ctcctggagc tgttggtggg aatatacccc tcaggggtta ttggactggt   1560
ccctcaccta ggggacaggg agaagagaga tagtgtgtgt ccccaaggaa aatatatcca   1620
ccctcaaaat aattcgattt gctgtaccaa gtgccacaaa ggaacctact tgtacaatga   1680
ctgtccaggc ccggggcagg atacggactg cagggagtgt gagagcggct ccttcaccgc   1740
ttcagaaaac cacctcagac actgcctcag ctgctccaaa tgccgaaagg aaatgggtca   1800
ggtggagatc tcttcttgca cagtggaccg ggacaccgtg tgtggctgca ggaagaacca   1860
gtaccggcat tattggagtg aaaacctttt ccagtgcttc aattgcagcc tctgcctcaa   1920
tgggaccgtg cacctctcct gccaggagaa acagaacacc gtgtgcacct gccatgcagg   1980
tttctttcta agagaaaacg agtgtgtctc ctgtagtaac tgtaagaaaa gcctggagtg   2040
cacgaagttg tgcctaccaa gcttaggatc cagatctaac ttggggtggc tttgtcttct   2100
tcttttgcca attccactaa ttgtttgggt gaagagaaag gaagtacaga aaacatgcag   2160
aaagcacaga aaggaaaacc aaggttctca tgaatctcca accttaaatc ctgaaacagt   2220
ggcaataaat ttatctgatg ttgacttgag taaatatatc accactattg ctggagtcat   2280
gacactaagt caagttaaag gctttgttcg aaagaatggt gtcaatgaag ccaaaataga   2340
tgagatcaag aatgacaatg tccaagacac agcagaacag aaagttcaac tgcttcgtaa   2400
ttggcatcaa cttcatggaa agaaagaagc gtatgacaca ttgattaaag atctcaaaaa   2460
agccaatctt tgtactcttg cagagaaaat tcagactatc atcctcaagg acattactag   2520
tgactcagaa aattcaaact tcagaaatga aatccaaagc ttggtctagc tcgagcatgc   2580
atctaggcgg ccgcatggca gaaattcgcg aattcgctag cgttaacgga tcctctagac   2640
gagatccgaa cttgtttatt gcagcttata atggttacaa ataaagcaat agcatcacaa   2700
atttcacaaa taaagcattt ttttcactgc attctagttg tggtttgtcc aaactcatca   2760
atgtatctta tcatgtctag atctgtactg aaatgtgtgg gcgtggctta agggtgggaa   2820
```

-continued

```
agaatatata aggtgggggt cttatgtagt tttgtatctg ttttgcagca gccgccgccg   2880

ccatgagcac caactcgttt gatggaagca ttgtgagctc atatttgaca acgcgcatgc   2940

ccccatgggc cggggtgcgt cagaatgtga tgggctccag cattgatggt cgccccgtcc   3000

tgcccgcaaa ctctactacc ttgacctacg agaccgtgtc tggaacgccg ttggagactg   3060

cagcctccgc cgccgcttca gccgctgcag ccaccgcccg cgggattgtg actgactttg   3120

ctttcctgag cccgcttgca agcagtgcag cttcccgttc atccgcccgc gatgacaagt   3180

tgacggctct tttggcacaa ttggattctt tgacccggga acttaatgtc gtttctcagc   3240

agctgttgga tctgcgccag caggtttctg ccctgaaggc ttcctcccct cccaatgcgg   3300

tttaaaacat aaataaaaaa ccagactctg tttggatttg gatcaagcaa gtgtcttgct   3360

gtctttattt aggggttttg cgcgcgcggt aggcccggga ccagcggtct cggtcgttga   3420

gggtcctgtg tatttttttcc aggacgtggt aaaggtgact ctggatgttc agatacatgg   3480

gcataagccc gtctctgggg tggaggtagc accactgcag agcttcatgc tgcggggtgg   3540

tgttgtagat gatccagtcg tagcaggagc gctgggcgtg gtgcctaaaa atgtctttca   3600

gtagcaagct gattgccagg ggcaggccct tggtgtaagt gtttacaaag cggttaagct   3660

gggatgggtg catacgtggg gatatgagat gcatcttgga ctgtattttt aggttggcta   3720

tgttcccagc catatccctc cggggattca tgttgtgcag aaccaccagc acagtgtatc   3780

cggtgcactt gggaaatttg tcatgtagct tagaaggaaa tgcgtggaag aacttggaga   3840

cgcccttgtg acctccaaga ttttccatgc attcgtccat aatgatggca atgggcccac   3900

gggcggcggc ctgggcgaag atatttctgg gatcactaac gtcatagttg tgttccagga   3960

tgagatcgtc ataggccatt tttacaaagc gcgggcggag ggtgccagac tgcggtataa   4020

tggttccatc cggcccaggg gcgtagttac cctcacagat ttgcatttcc cacgctttga   4080

gttcagatgg ggggatcatg tctacctgcg gggcgatgaa gaaaacggtt tccggggtag   4140

gggagatcag ctgggaagaa agcaggttcc tgagcagctg cgacttaccg cagccggtgg   4200

gcccgtaaat cacacctatt accggctgca actggtagtt aagagagctg cagctgccgt   4260

catccctgag caggggggcc acttcgttaa gcatgtccct gactcgcatg ttttccctga   4320

ccaaatccgc cagaaggcgc tcgccgccca gcgatagcag ttcttgcaag gaagcaaagt   4380

ttttcaacgg tttgagaccg tccgccgtag gcatgctttt gagcgtttga ccaagcagtt   4440

ccaggcggtc ccacagctcg gtcacctgct ctacggcatc tcgatccagc atatctcctc   4500

gtttcgcggg ttggggcggc tttcgctgta cggcagtagt cggtgctcgt ccagacgggc   4560

cagggtcatg tctttccacg ggcgcagggt cctcgtcagc gtagtctggg tcacggtgaa   4620

ggggtgcgct ccgggctgcg cgctggccag ggtgcgcttg aggctggtcc tgctggtgct   4680

gaagcgctgc cggtcttcgc cctgcgcgtc ggccaggtag catttgacca tggtgtcata   4740

gtccagcccc tccgcggcgt ggcccttggc gcgcagcttg cccttggagg aggcgccgca   4800

cgaggggcag tgcagacttt tgagggcgta gagcttgggc gcgagaaata ccgattccgg   4860

ggagtaggca tccgcgccgc aggccccgca gacggtctcg cattccacga gccaggtgag   4920

ctctggccgt tcggggtcaa aaaccaggtt tcccccatgc tttttgatgc gtttcttacc   4980

tctggtttcc atgagccggt gtccacgctc ggtgacgaaa aggctgtccg tgtccccgta   5040

tacagacttg agaggcctgt cctcgagcgg tgttccgcgg tcctcctcgt atagaaactc   5100

ggaccactct gagacaaagg ctcgcgtcca ggccagcacg aaggaggcta agtgggaggg   5160

gtagcggtcg ttgtccacta gggggtccac tcgctccagg gtgtgaagac acatgtcgcc   5220
```

```
ctcttcggca tcaaggaagg tgattggttt gtaggtgtag gccacgtgac cgggtgttcc   5280
tgaagggggg ctataaaagg gggtgggggc gcgttcgtcc tcactctctt ccgcatcgct   5340
gtctgcgagg gccagctgtt ggggtgagta ctccctctga aaagcgggca tgacttctgc   5400
gctaagattg tcagtttcca aaaacgagga ggatttgata ttcacctggc ccgcggtgat   5460
gcctttgagg gtggccgcat ccatctggtc agaaaagaca atctttttgt tgtcaagctt   5520
ggtggcaaac gacccgtaga gggcgttgga cagcaacttg gcgatggagc gcagggtttg   5580
gtttttgtcg cgatcggcgc gctccttggc cgcgatgttt agctgcacgt attcgcgcgc   5640
aacgcaccgc cattcgggaa agacggtggt gcgctcgtcg ggcaccaggt gcacgcgcca   5700
accgcggttg tgcagggtga caaggtcaac gctggtggct acctctccgc gtaggcgctc   5760
gttggtccag cagaggcggc cgcccttgcg cgagcagaat ggcggtaggg ggtctagctg   5820
cgtctcgtcc ggggggtctg cgtccacggt aaagaccccg ggcagcaggc gcgcgtcgaa   5880
gtagtctatc ttgcatcctt gcaagtctag cgcctgctgc catgcgcggg cggcaagcgc   5940
gcgctcgtat gggttgagtg ggggacccca tggcatgggg tgggtgagcg cggaggcgta   6000
catgccgcaa atgtcgtaaa cgtagagggg ctctctgagt attccaagat atgtagggta   6060
gcatcttcca ccgcggatgc tggcgcgcac gtaatcgtat agttcgtgcg agggagcgag   6120
gaggtcggga ccgaggttgc tacgggcggg ctgctctgct cggaagacta tctgcctgaa   6180
gatggcatgt gagttggatg atatggttgg acgctggaag acgttgaagc tggcgtctgt   6240
gagacctacc gcgtcacgca cgaaggaggc gtaggagtcg cgcagcttgt tgaccagctc   6300
ggcggtgacc tgcacgtcta gggcgcagta gtccagggtt tccttgatga tgtcatactt   6360
atcctgtccc ttttttttcc acagctcgcg gttgaggaca aactcttcgc ggtctttcca   6420
gtactcttgg atcggaaacc cgtcggcctc cgaacggtaa gagcctagca tgtagaactg   6480
gttgacggcc tggtaggcgc agcatccctt ttctacgggt agcgcgtatg cctgcgcggc   6540
cttccggagc gaggtgtggg tgagcgcaaa ggtgtccctg accatgactt tgaggtactg   6600
gtatttgaag tcagtgtcgt cgcatccgcc ctgctcccag agcaaaaagt ccgtgcgctt   6660
tttggaacgc ggatttggca gggcgaaggt gacatcgttg aagagtatct ttcccgcgcg   6720
aggcataaag ttgcgtgtga tgcggaaggg tcccggcacc tcggaacggt tgttaattac   6780
ctgggcggcg agcacgatct cgtcaaagcc gttgatgttg tggcccacaa tgtaaagttc   6840
caagaagcgc gggatgccct tgatggaagg caatttttta agttcctcgt aggtgagctc   6900
ttcaggggag ctgagcccgt gctctgaaag ggcccagtct gcaagatgag ggttggaagc   6960
gacgaatgag ctccacaggt cacgggccat tagcatttgc aggtggtcgc gaaaggtcct   7020
aaactggcga cctatggcca tttttctgg ggtgatgcag tagaaggtaa gcgggtcttg    7080
ttcccagcgg tcccatccaa ggttcgcggc taggtctcgc gcggcagtca ctagaggctc   7140
atctccgccg aacttcatga ccagcatgaa gggcacgagc tgcttcccaa aggcccccat   7200
ccaagtatag gtctctacat cgtaggtgac aaagagacgc tcggtgcgag gatgcgagcc   7260
gatcgggaag aactggatct cccgccacca attggaggag tggctattga tgtggtgaaa   7320
gtagaagtcc ctgcgacggg ccgaacactc gtgctggctt ttgtaaaaac gtgcgcagta   7380
ctggcagcgg tgcacgggct gtacatcctg cacgaggttg acctgacgac cgcgcacaag   7440
gaagcagagt gggaatttga gcccctcgcc tggcgggttt ggctggtggt cttctacttc   7500
ggctgcttgt ccttgaccgt ctggctgctc gaggggagtt acggtggatc ggaccaccac   7560
```

```
gccgcgcgag cccaaagtcc agatgtccgc gcgcggcggt cggagcttga tgacaacatc   7620
gcgcagatgg gagctgtcca tggtctggag ctcccgcggc gtcaggtcag gcgggagctc   7680
ctgcaggttt acctcgcata gacgggtcag ggcgcgggct agatccaggt gatacctaat   7740
ttccaggggc tggttggtgg cggcgtcgat ggcttgcaag aggccgcatc cccgcggcgc   7800
gactacggta ccgcgcggcg ggcggtgggc cgcgggggtg tccttggatg atgcatctaa   7860
aagcggtgac gcgggcgagc ccccggaggt aggggggct ccggacccgc cgggagaggg   7920
ggcaggggca cgtcggcgcc gcgcgcgggc aggagctggt gctgcgcgcg taggttgctg   7980
gcgaacgcga cgacgcggcg gttgatctcc tgaatctggc gcctctgcgt gaagacgacg   8040
ggcccggtga gcttgaacct gaaagagagt tcgacagaat caatttcggt gtcgttgacg   8100
gcggcctggc gcaaaatctc ctgcacgtct cctgagttgt cttgataggc gatctcggcc   8160
atgaactgct cgatctcttc ctcctggaga tctccgcgtc cggctcgctc cacggtggcg   8220
gcgaggtcgt tggaaatgcg ggccatgagc tgcgagaagg cgttgaggcc tccctcgttc   8280
cagacgcggc tgtagaccac gccccccttcg gcatcgcggg cgcgcatgac cacctgcgcg   8340
agattgagct ccacgtgccg ggcgaagacg gcgtagtttc gcaggcgctg aaagaggtag   8400
ttgagggtgg tggcggtgtg ttctgccacg aagaagtaca taacccagcg tcgcaacgtg   8460
gattcgttga tatcccccaa ggcctcaagg cgctccatgg cctcgtagaa gtccacggcg   8520
aagttgaaaa actgggagtt gcgcgccgac acggttaact cctcctccag aagacggatg   8580
agctcggcga cagtgtcgcg cacctcgcgc tcaaaggcta caggggcctc ttcttcttct   8640
tcaatctcct cttccataag ggcctcccct tcttcttctt ctggcggcgg tgggggaggg   8700
gggacacggc ggcgacgacg gcgcaccggg aggcggtcga caaagcgctc gatcatctcc   8760
ccgcggcgac ggcgcatggt ctcggtgacg gcgcggccgt tctcgcgggg gcgcagttgg   8820
aagacgccgc ccgtcatgtc ccggttatgg gttggcgggg ggctgccatg cggcagggat   8880
acggcgctaa cgatgcatct caacaattgt tgtgtaggta ctccgccgcc gagggacctg   8940
agcgagtccg catcgaccgg atcggaaaac ctctcgagaa aggcgtctaa ccagtcacag   9000
tcgcaaggta ggctgagcac cgtggcgggc ggcagcgggc ggcggtcggg gttgtttctg   9060
gcggaggtgc tgctgatgat gtaattaaag taggcggtct tgagacggcg gatggtcgac   9120
agaagcacca tgtccttggg tccggcctgc tgaatgcgca ggcggtcggc catgccccag   9180
gcttcgtttt gacatcggcg caggtctttg tagtagtctt gcatgagcct ttctaccggc   9240
acttcttctt ctccttcctc ttgtcctgca tctcttgcat ctatcgctgc ggcggcggcg   9300
gagtttggcc gtaggtggcg ccctcttcct cccatgcgtg tgaccccgaa gcccctcatc   9360
ggctgaagca gggctaggtc ggcgacaacg cgctcggcta atatggcctg ctgcacctgc   9420
gtgagggtag actggaagtc atccatgtcc acaaagcggt ggtatgcgcc cgtgttgatg   9480
gtgtaagtgc agttggccat aacggaccag ttaacggtct ggtgacccgg ctgcgagagc   9540
tcggtgtacc tgagacgcga gtaagccctc gagtcaaata cgtagtcgtt gcaagtccgc   9600
accaggtact ggtatcccac caaaaagtgc ggcggcggct ggcggtagag gggccagcgt   9660
agggtggccg gggctccggg ggcgagatct tccaacataa ggcgatgata tccgtagatg   9720
tacctggaca tccaggtgat gccggcggcg gtggtggagg cgcgcggaaa gtcgcggacg   9780
cggttccaga tgttgcgcag cggcaaaaag tgctccatgg tcgggacgct ctggccggtc   9840
aggcgcgcgc aatcgttgac gctctagacc gtgcaaaagg agagcctgta agcgggcact   9900
cttccgtggt ctggtggata aattcgcaag ggtatcatgg cggacgaccg gggttcgagc   9960
```

```
cccgtatccg gccgtccgcc gtgatccatg cggttaccgc ccgcgtgtcg aacccaggtg  10020
tgcgacgtca gacaacgggg gagtgctcct tttggcttcc ttccaggcgc ggcggctgct  10080
gcgctagctt ttttggccac tggccgcgcg cagcgtaagc ggttaggctg gaaagcgaaa  10140
gcattaagtg gctcgctccc tgtagccgga gggttatttt ccaagggttg agtcgcggga  10200
cccccggttc gagtctcgga ccggccggac tgcggcgaac gggggtttgc ctccccgtca  10260
tgcaagaccc cgcttgcaaa ttcctccgga aacagggacg agcccctttt ttgcttttcc  10320
cagatgcatc cggtgctgcg gcagatgcgc ccccctcctc agcagcggca agagcaagag  10380
cagcggcaga catgcagggc accctcccct cctcctaccg cgtcaggagg ggcgacatcc  10440
gcggttgacg cggcagcaga tggtgattac gaacccccgc ggcgccgggc ccggcactac  10500
ctggacttgg aggagggcga gggcctggcg cggctaggag cgccctctcc tgagcggcac  10560
ccaagggtgc agctgaagcg tgatacgcgt gaggcgtacg tgccgcggca gaacctgttt  10620
cgcgaccgcg agggagagga gcccgaggag atgcgggatc gaaagttcca cgcagggcgc  10680
gagctgcggc atggcctgaa tcgcgagcgg ttgctgcgcg aggaggactt tgagcccgac  10740
gcgcgaaccg ggattagtcc cgcgcgcgca cacgtggcgg ccgccgacct ggtaaccgca  10800
tacgagcaga cggtgaacca ggagattaac tttcaaaaaa gctttaacaa ccacgtgcgt  10860
acgcttgtgg cgcgcgagga ggtggctata ggactgatgc atctgtggga ctttgtaagc  10920
gcgctggagc aaaacccaaa tagcaagccg ctcatggcgc agctgttcct tatagtgcag  10980
cacagcaggg acaacgaggc attcagggat gcgctgctaa acatagtaga gcccgagggc  11040
cgctggctgc tcgatttgat aaacatcctg cagagcatag tggtgcagga gcgcagcttg  11100
agcctggctg acaaggtggc cgccatcaac tattccatgc ttagcctggg caagttttac  11160
gcccgcaaga tataccatac cccttacgtt cccatagaca aggaggtaaa gatcgagggg  11220
ttctacatgc gcatggcgct gaaggtgctt accttgagcg acgacctggg cgtttatcgc  11280
aacgagcgca tccacaaggc cgtgagcgtg agccggcggc gcgagctcag cgaccgcgag  11340
ctgatgcaca gcctgcaaag ggccctggct ggcacgggca gcggcgatag agaggccgag  11400
tcctactttg acgcgggcgc tgacctgcgc tgggccccaa gccgacgcgc cctggaggca  11460
gctggggccg gacctgggct ggcggtggca cccgcgcgcg ctggcaacgt cggcggcgtg  11520
gaggaatatg acgaggacga tgagtacgag ccagaggacg gcgagtacta agcggtgatg  11580
tttctgatca gatgatgcaa gacgcaacgg acccggcggt gcgggcggcg ctgcagagcc  11640
agccgtccgg ccttaactcc acggacgact ggcgccaggt catggaccgc atcatgtcgc  11700
tgactgcgcg caatcctgac gcgttccggc agcagccgca ggccaaccgg ctctccgcaa  11760
ttctggaagc ggtggtcccg gcgcgcgcaa accccacgca cgagaaggtg ctggcgatcg  11820
taaacgcgct ggccgaaaac agggccatcc ggcccgacga ggccggcctg gtctacgacg  11880
cgctgcttca gcgcgtggct cgttacaaca gcggcaacgt gcagaccaac ctggaccggc  11940
tggtggggga tgtgcgcgag gccgtggcgc agcgtgagcg cgcgcagcag cagggcaacc  12000
tgggctccat ggttgcacta aacgccttcc tgagtacaca gcccgccaac gtgccgcggg  12060
gacaggagga ctacaccaac tttgtgagcg cactgcggct aatggtgact gagacaccgc  12120
aaagtgaggt gtaccagtct gggccagact atttttttcca gaccagtaga caaggcctgc  12180
agaccgtaaa cctgagccag gctttcaaaa acttgcaggg gctgtggggg gtgcgggctc  12240
ccacaggcga ccgcgcgacc gtgtctagct tgctgacgcc caactcgcgc ctgttgctgc  12300
```

-continued

```
tgctaatagc gcccttcacg gacagtggca gcgtgtcccg ggacacatac ctaggtcact  12360
tgctgacact gtaccgcgag gccataggtc aggcgcatgt ggacgagcat actttccagg  12420
agattacaag tgtcagccgc gcgctggggc aggaggacac gggcagcctg gaggcaaccc  12480
taaactacct gctgaccaac cggcggcaga agatcccctc gttgcacagt ttaaacagcg  12540
aggaggagcg cattttgcgc tacgtgcagc agagcgtgag ccttaacctg atgcgcgacg  12600
gggtaacgcc cagcgtggcg ctggacatga ccgcgcgcaa catggaaccg ggcatgtatg  12660
cctcaaaccg gccgtttatc aaccgcctaa tggactactt gcatcgcgcg gccgccgtga  12720
accccgagta tttcaccaat gccatcttga acccgcactg gctaccgccc cctggtttct  12780
acaccggggg attcgaggtg cccgagggta acgatggatt cctctgggac gacatagacg  12840
acagcgtgtt ttccccgcaa ccgcagaccc tgctagagtt gcaacagcgc gagcaggcag  12900
aggcggcgct gcgaaaggaa agcttccgca ggccaagcag cttgtccgat ctaggcgctg  12960
cggccccgcg gtcagatgct agtagcccat ttccaagctt gatagggtct cttaccagca  13020
ctcgcaccac ccgcccgcgc ctgctgggcg aggaggagta cctaaacaac tcgctgctgc  13080
agccgcagcg cgaaaaaaac ctgcctccgg catttcccaa caacgggata gagagcctag  13140
tggacaagat gagtagatgg aagacgtacg cgcaggagca cagggacgtg ccaggcccgc  13200
gcccgcccac ccgtcgtcaa aggcacgacc gtcagcgggg tctggtgtgg gaggacgatg  13260
actcggcaga cgacagcagc gtcctggatt tgggagggag tggcaacccg tttgcgcacc  13320
ttcgccccag gctggggaga atgttttaaa aaaaaaaaaa gcatgatgca aaataaaaaa  13380
ctcaccaagg ccatggcacc gagcgttggt tttcttgtat tccccttagt atgcggcgcg  13440
cggcgatgta tgaggaaggt cctcctccct cctacgagag tgtggtgagc gcggcgccag  13500
tggcggcggc gctgggttct cccttcgatg ctcccctgga cccgccgttt gtgcctccgc  13560
ggtacctgcg gcctaccggg gggagaaaca gcatccgtta ctctgagttg gcacccctat  13620
tcgacaccac ccgtgtgtac ctggtggaca acaagtcaac ggatgtggca tccctgaact  13680
accagaacga ccacagcaac tttctgacca cggtcattca aaacaatgac tacagcccgg  13740
gggaggcaag cacacagacc atcaatcttg acgaccggtc gcactggggc ggcgacctga  13800
aaaccatcct gcataccaac atgccaaatg tgaacgagtt catgtttacc aataagttta  13860
aggcgcgggt gatggtgtcg cgcttgccta ctaaggacaa tcaggtggag ctgaaatacg  13920
agtgggtgga gttcacgctg cccgagggca actactccga gaccatgacc atagacctta  13980
tgaacaacgc gatcgtggag cactacttga aagtgggcag acagaacggg gttctggaaa  14040
gcgacatcgg ggtaaagttt gacacccgca acttcagact ggggtttgac cccgtcactg  14100
gtcttgtcat gcctggggta tatacaaacg aagccttcca tccagacatc attttgctgc  14160
caggatgcgg ggtggacttc acccacagcc gcctgagcaa cttgttgggc atccgcaagc  14220
ggcaaccctt ccaggagggc tttaggatca cctacgatga tctggagggt ggtaacattc  14280
ccgcactgtt ggatgtggac gcctaccagg cgagcttgaa agatgacacc gaacagggcg  14340
gggtggcgc aggcggcagc aacagcagtg gcagcggcgc ggaagagaac tccaacgcgg  14400
cagccgcggc aatgcagccg gtggaggaca tgaacgatca tgccattcgc ggcgacacct  14460
ttgccacacg ggctgaggag aagcgcgctg aggccgaagc agcggccgaa gctgccgccc  14520
ccgctgcgca acccgaggtc gagaagcctc agaagaaacc ggtgatcaaa cccctgacag  14580
aggacagcaa gaaacgcagt tacaacctaa taagcaatga cagcaccttc acccagtacc  14640
gcagctggta ccttgcatac aactacggcg accctcagac cggaatccgc tcatggaccc  14700
```

```
tgctttgcac tcctgacgta acctgcggct cggagcaggt ctactggtcg ttgccagaca  14760
tgatgcaaga ccccgtgacc ttccgctcca cgcgccagat cagcaacttt ccggtggtgg  14820
gcgccgagct gttgcccgtg cactccaaga gcttctacaa cgaccaggcc gtctactccc  14880
aactcatccg ccagtttacc tctctgaccc acgtgttcaa tcgctttccc gagaaccaga  14940
ttttggcgcg cccgccagcc cccaccatca ccaccgtcag tgaaaacgtt cctgctctca  15000
cagatcacgg gacgctaccg ctgcgcaaca gcatcggagg agtccagcga gtgaccatta  15060
ctgacgccag acgccgcacc tgcccctacg tttacaaggc cctgggcata gtctcgccgc  15120
gcgtcctatc gagccgcact ttttgagcaa gcatgtccat ccttatatcg cccagcaata  15180
acacaggctg gggcctgcgc ttcccaagca agatgtttgg cggggccaag aagcgctccg  15240
accaacaccc agtgcgcgtg cgcgggcact accgcgcgcc ctggggcgcg cacaaacgcg  15300
gccgcactgg gcgcaccacc gtcgatgacg ccatcgacgc ggtggtggag gaggcgcgca  15360
actacacgcc cacgccgcca ccagtgtcca cagtggacgc ggccattcag accgtggtgc  15420
gcggagcccg gcgctatgct aaaatgaaga gacggcggag gcgcgtagca cgtcgccacc  15480
gccgccgacc cggcactgcc gcccaacgcg cggcggcggc cctgcttaac cgcgcacgtc  15540
gcaccggccg acgggcggcc atgcgggccg ctcgaaggct ggccgcgggt attgtcactg  15600
tgccccccag gtccaggcga cgagcggccg ccgcagcagc cgcggccatt agtgctatga  15660
ctcagggtcg caggggcaac gtgtattggg tgcgcgactc ggttagcggc ctgcgcgtgc  15720
ccgtgcgcac ccgccccccg cgcaactaga ttgcaagaaa aaactactta gactcgtact  15780
gttgtatgta tccagcggcg gcggcgcgca acgaagctat gtccaagcgc aaaatcaaag  15840
aagagatgct ccaggtcatc gcgccggaga tctatggccc cccgaagaag gaagagcagg  15900
attacaagcc ccgaaagcta aagcgggtca aaaagaaaaa gaaagatgat gatgatgaac  15960
ttgacgacga ggtggaactg ctgcacgcta ccgcgcccag gcgacgggta cagtggaaag  16020
gtcgacgcgt aaaacgtgtt ttgcgacccg gcaccaccgt agtctttacg cccggtgagc  16080
gctccacccg cacctacaag cgcgtgtatg atgaggtgta cggcgacgag gacctgcttg  16140
agcaggccaa cgagcgcctc ggggagtttg cctacggaaa gcggcataag gacatgctgg  16200
cgttgccgct ggacgagggc aacccaacac ctagcctaaa gcccgtaaca ctgcagcagg  16260
tgctgcccgc gcttgcaccg tccgaagaaa agcgcggcct aaagcgcgag tctggtgact  16320
tggcacccac cgtgcagctg atggtaccca agcgccagcg actggaagat gtcttggaaa  16380
aaatgaccgt ggaacctggg ctggagcccg aggtccgcgt gcggccaatc aagcaggtgg  16440
cgccgggact gggcgtgcag accgtggacg ttcagatacc cactaccagt agcaccagta  16500
ttgccaccgc cacagagggc atggagacac aaacgtcccc ggttgcctca gcggtggcgg  16560
atgccgcggt gcaggcggtc gctgcggccg cgtccaagac ctctacggag gtgcaaacgg  16620
acccgtggat gtttcgcgtt tcagcccccc ggcgcccgcg ccgttcgagg aagtacggcg  16680
ccgccagcgc gctactgccc gaatatgccc tacatccttc cattgcgcct acccccggct  16740
atcgtggcta cacctaccgc cccagaagac gagcaactac ccgacgccga accaccactg  16800
gaacccgccg ccgccgtcgc cgtcgccagc ccgtgctggc cccgatttcc gtgcgcaggg  16860
tggctcgcga aggaggcagg accctggtgc tgccaacagc gcgctaccac cccagcatcg  16920
tttaaaagcc ggtctttgtg gttcttgcag atatggccct cacctgccgc ctccgtttcc  16980
cggtgccggg attccgagga agaatgcacc gtaggagggg catggccggc cacggcctga  17040
```

```
cgggcggcat gcgtcgtgcg caccaccggc ggcggcgcgc gtcgcaccgt cgcatgcgcg  17100
gcggtatcct gcccctcctt attccactga tcgccgcggc gattggcgcc gtgcccggaa  17160
ttgcatccgt ggccttgcag gcgcagagac actgattaaa aacaagttgc atgtggaaaa  17220
atcaaaataa aaagtctgga ctctcacgct cgcttggtcc tgtaactatt ttgtagaatg  17280
gaagacatca actttgcgtc tctggccccg cgacacggct cgcgcccgtt catgggaaac  17340
tggcaagata tcggcaccag caatatgagc ggtggcgcct tcagctgggg ctcgctgtgg  17400
agcggcatta aaaatttcgg ttccaccgtt aagaactatg gcagcaaggc ctggaacagc  17460
agcacaggcc agatgctgag ggataagttg aaagagcaaa atttccaaca aaaggtggta  17520
gatggcctgg cctctggcat tagcggggtg gtggacctgg ccaaccaggc agtgcaaaat  17580
aagattaaca gtaagcttga tccccgccct cccgtagagg agcctccacc ggccgtggag  17640
acagtgtctc cagaggggcg tggcgaaaag cgtccgcgcc ccgacaggga agaaactctg  17700
gtgacgcaaa tagacgagcc tccctcgtac gaggaggcac taaagcaagg cctgcccacc  17760
acccgtccca tcgcgcccat ggctaccgga gtgctgggcc agcacacacc cgtaacgctg  17820
gacctgcctc cccccgccga cacccagcag aaacctgtgc tgccaggccc gaccgccgtt  17880
gttgtaaccc gtcctagccg cgcgtccctg cgccgcgccg ccagcggtcc gcgatcgttg  17940
cggcccgtag ccagtggcaa ctggcaaagc acactgaaca gcatcgtggg tctgggggtg  18000
caatccctga agcgccgacg atgcttctga tagctaacgt gtcgtatgtg tgtcatgtat  18060
gcgtccatgt cgccgccaga ggagctgctg agccgccgcg cgcccgcttt ccaagatggc  18120
taccccttcg atgatgccgc agtggtctta catgcacatc tcgggccagg acgcctcgga  18180
gtacctgagc cccgggctgg tgcagtttgc ccgcgccacc gagacgtact tcagcctgaa  18240
taacaagttt agaaacccca cggtggcgcc tacgcacgac gtgaccacag accggtccca  18300
gcgtttgacg ctgcggttca tccctgtgga ccgtgaggat actgcgtact cgtacaaggc  18360
gcggttcacc ctagctgtgg gtgataaccg tgtgctggac atggcttcca cgtactttga  18420
catccgcggc gtgctggaca ggggccctac ttttaagccc tactctggca ctgcctacaa  18480
cgccctggct cccaagggtg ccccaaatcc ttgcgaatgg gatgaagctg ctactgctct  18540
tgaaataaac ctagaagaag aggacgatga caacgaagac gaagtagacg agcaagctga  18600
gcagcaaaaa actcacgtat ttgggcaggc gccttattct ggtataaata ttacaaagga  18660
gggtattcaa ataggtgtcg aaggtcaaac acctaaatat gccgataaaa catttcaacc  18720
tgaacctcaa ataggagaat ctcagtggta cgaaacagaa attaatcatg cagctgggag  18780
agtcctaaaa aagactaccc caatgaaacc atgttacggt tcatatgcaa aacccacaaa  18840
tgaaaatgga gggcaaggca ttcttgtaaa gcaacaaaat ggaaagctag aaagtcaagt  18900
ggaaatgcaa tttttctcaa ctactgaggc agccgcaggc aatggtgata acttgactcc  18960
taaagtggta ttgtacagtg aagatgtaga tatagaaacc ccagacactc atatttctta  19020
catgcccact attaaggaag gtaactcacg agaactaatg ggccaacaat ctatgcccaa  19080
caggcctaat tacattgctt ttagggacaa ttttattggt ctaatgtatt acaacagcac  19140
gggtaatatg ggtgttctgg cgggccaagc atcgcagttg aatgctgttg tagatttgca  19200
agacagaaac acagagcttt cataccagct tttgcttgat tccattggtg atagaaccag  19260
gtacttttct atgtggaatc aggctgttga cagctatgat ccagatgtta gaattattga  19320
aaatcatgga actgaagatg aacttccaaa ttactgcttt ccactgggag gtgtgattaa  19380
tacagagact cttaccaagg taaaacctaa aacaggtcag gaaaatggat gggaaaaaga  19440
```

```
tgctacagaa ttttcagata aaaatgaaat aagagttgga aataattttg ccatggaaat  19500

caatctaaat gccaacctgt ggagaaattt cctgtactcc aacatagcgc tgtatttgcc  19560

cgacaagcta aagtacagtc cttccaacgt aaaaatttct gataacccaa acacctacga  19620

ctacatgaac aagcgagtgg tggctcccgg gctagtggac tgctacatta accttggagc  19680

acgctggtcc cttgactata tggacaacgt caacccattt aaccaccacc gcaatgctgg  19740

cctgcgctac cgctcaatgt tgctgggcaa tggtcgctat gtgcccttcc acatccaggt  19800

gcctcagaag ttctttgcca ttaaaaacct ccttctcctg ccgggctcat acacctacga  19860

gtggaacttc aggaaggatg ttaacatggt tctgcagagc tccctaggaa atgacctaag  19920

ggttgacgga gccagcatta agtttgatag catttgcctt tacgccacct tcttccccat  19980

ggcccacaac accgcctcca cgcttgaggc catgcttaga aacgacacca acgaccagtc  20040

ctttaacgac tatctctccg ccgccaacat gctctaccct atacccgcca acgctaccaa  20100

cgtgcccata tccatcccct cccgcaactg ggcggctttc cgcggctggg ccttcacgcg  20160

ccttaagact aaggaaaccc catcactggg ctcgggctac gacccttatt acacctactc  20220

tggctctata ccctacctag atggaacctt ttacctcaac cacaccttta agaaggtggc  20280

cattaccttt gactcttctg tcagctggcc tggcaatgac cgcctgctta cccccaacga  20340

gtttgaaatt aagcgctcag ttgacgggga gggttacaac gttgcccagt gtaacatgac  20400

caaagactgg ttcctggtac aaatgctagc taactataac attggctacc agggcttcta  20460

tatcccagag agctacaagg accgcatgta ctccttcttt agaaacttcc agcccatgag  20520

ccgtcaggtg gtggatgata ctaaatacaa ggactaccaa caggtgggca tcctacacca  20580

acacaacaac tctggatttg ttggctacct tgcccccacc atgcgcgaag gacaggccta  20640

ccctgctaac ttccccctatc cgcttatagg caagaccgca gttgacagca ttacccagaa  20700

aaagtttctt tgcgatcgca ccctttggcg catcccattc tccagtaact ttatgtccat  20760

gggcgcactc acagacctgg gccaaaacct tctctacgcc aactccgccc acgcgctaga  20820

catgactttt gaggtggatc ccatggacga gcccaccctt ctttatgttt tgtttgaagt  20880

ctttgacgtg gtccgtgtgc accagccgca ccgcggcgtc atcgaaaccg tgtacctgcg  20940

cacgcccttc tcggccggca acgccacaac ataaagaagc aagcaacatc aacaacagct  21000

gccgccatgg gctccagtga gcaggaactg aaagccattg tcaaagatct tggttgtggg  21060

ccatattttt tgggcaccta tgacaagcgc tttccaggct ttgtttctcc acacaagctc  21120

gcctgcgcca tagtcaatac ggccggtcgc gagactgggg gcgtacactg gatggccttt  21180

gcctggaacc cgcactcaaa aacatgctac ctctttgagc cctttggctt ttctgaccag  21240

cgactcaagc aggtttacca gtttgagtac gagtcactcc tgcgccgtag cgccattgct  21300

tcttcccccg accgctgtat aacgctggaa aagtccaccc aaagcgtaca ggggcccaac  21360

tcggccgcct gtggactatt ctgctgcatg tttctccacg cctttgccaa ctggccccaa  21420

actcccatgg atcacaaccc caccatgaac cttattaccg ggtacccaa ctccatgctc  21480

aacagtcccc aggtacagcc caccctgcgt cgcaaccagg aacagctcta cagcttcctg  21540

gagcgccact cgccctactt ccgcagccac agtgcgcaga ttaggagcgc cacttctttt  21600

tgtcacttga aaaacatgta aaaataatgt actagagaca ctttcaataa aggcaaatgc  21660

ttttatttgt acactctcgg gtgattattt acccccaccc ttgccgtctg cgccgtttaa  21720

aaatcaaagg ggttctgccg cgcatcgcta tgcgccactg gcagggacac gttgcgatac  21780
```

```
tggtgtttag tgctccactt aaactcaggc acaaccatcc gcggcagctc ggtgaagttt  21840
tcactccaca ggctgcgcac catcaccaac gcgtttagca ggtcgggcgc cgatatcttg  21900
aagtcgcagt tggggcctcc gccctgcgcg cgcgagttgc gatacacagg gttgcagcac  21960
tggaacacta tcagcgccgg gtggtgcacg ctggccagca cgctcttgtc ggagatcaga  22020
tccgcgtcca ggtcctccgc gttgctcagg gcgaacggag tcaactttgg tagctgcctt  22080
cccaaaaagg gcgcgtgccc aggctttgag ttgcactcgc accgtagtgg catcaaaagg  22140
tgaccgtgcc cggtctgggc gttaggatac agcgcctgca taaaagcctt gatctgctta  22200
aaagccacct gagcctttgc gccttcagag aagaacatgc cgcaagactt gccggaaaac  22260
tgattggccg gacaggccgc gtcgtgcacg cagcaccttg cgtcggtgtt ggagatctgc  22320
accacatttc ggccccaccg gttcttcacg atcttggcct tgctagactg ctccttcagc  22380
gcgcgctgcc cgttttcgct cgtcacatcc atttcaatca cgtgctcctt atttatcata  22440
atgcttccgt gtagacactt aagctcgcct tcgatctcag cgcagcggtg cagccacaac  22500
gcgcagcccg tgggctcgtg atgcttgtag gtcacctctg caaacgactg caggtacgcc  22560
tgcaggaatc gccccatcat cgtcacaaag gtcttgttgc tggtgaaggt cagctgcaac  22620
ccgcggtgct cctcgttcag ccaggtcttg catacggccg ccagagcttc cacttggtca  22680
ggcagtagtt tgaagttcgc ctttagatcg ttatccacgt ggtacttgtc catcagcgcg  22740
cgcgcagcct ccatgccctt ctcccacgca gacacgatcg gcacactcag cgggttcatc  22800
accgtaattt cactttccgc ttcgctgggc tcttcctctt cctcttgcgt ccgcatacca  22860
cgcgccactg ggtcgtcttc attcagccgc cgcactgtgc gcttacctcc tttgccatgc  22920
ttgattagca ccggtgggtt gctgaaaccc accatttgta gcgccacatc ttctctttct  22980
tcctcgctgt ccacgattac ctctggtgat ggcgggcgct cgggcttggg agaagggcgc  23040
ttctttttct tcttgggcgc aatggccaaa tccgccgccg aggtcgatgg ccgcgggctg  23100
ggtgtgcgcg gcaccagcgc gtcttgtgat gagtcttcct cgtcctcgga ctcgatacgc  23160
cgcctcatcc gcttttttgg gggcgcccgg ggaggcggcg gcgacgggga cggggacgac  23220
acgtcctcca tggttggggg acgtcgcgcc gcaccgcgtc cgcgctcggg ggtggtttcg  23280
cgctgctcct cttcccgact ggccatttcc ttctcctata ggcagaaaaa gatcatggag  23340
tcagtcgaga agaaggacag cctaaccgcc ccctctgagt tcgccaccac cgcctccacc  23400
gatgccgcca acgcgcctac caccttcccc gtcgaggcac ccccgcttga ggaggaggaa  23460
gtgattatcg agcaggaccc aggttttgta agcgaagacg acgaggaccg ctcagtacca  23520
acagaggata aaaagcaaga ccaggacaac gcagaggcaa acgaggaaca agtcgggcgg  23580
ggggacgaaa ggcatggcga ctacctagat gtgggagacg acgtgctgtt gaagcatctg  23640
cagcgccagt gcgccattat ctgcgacgcg ttgcaagagc gcagcgatgt gcccctcgcc  23700
atagcggatg tcagccttgc ctacgaacgc cacctattct caccgcgcgt accccccaaa  23760
cgccaagaaa acggcacatg cgagcccaac ccgcgcctca acttctaccc cgtatttgcc  23820
gtgccagagg tgcttgccac ctatcacatc tttttccaaa actgcaagat acccctatcc  23880
tgccgtgcca accgcagccg agcggacaag cagctggcct tgcggcaggg cgctgtcata  23940
cctgatatcg cctcgctcaa cgaagtgcca aaaatctttg agggtcttgg acgcgacgag  24000
aagcgcgcgg caaacgctct gcaacaggaa aacagcgaaa atgaaagtca ctctggagtg  24060
ttggtggaac tcgagggtga caacgcgcgc ctagccgtac taaaacgcag catcgaggtc  24120
acccactttg cctacccggc acttaaccta ccccccaagg tcatgagcac agtcatgagt  24180
```

```
gagctgatcg tgcgccgtgc gcagcccctg gagagggatg caaatttgca agaacaaaca  24240
gaggagggcc tacccgcagt tggcgacgag cagctagcgc gctggcttca aacgcgcgag  24300
cctgccgact tggaggagcg acgcaaacta atgatggccg cagtgctcgt taccgtggag  24360
cttgagtgca tgcagcggtt ctttgctgac ccggagatgc agcgcaagct agaggaaaca  24420
ttgcactaca cctttcgaca gggctacgta cgccaggcct gcaagatctc caacgtggag  24480
ctctgcaacc tggtctccta ccttggaatt ttgcacgaaa accgccttgg gcaaaacgtg  24540
cttcattcca cgctcaaggg cgaggcgcgc cgcgactacg tccgcgactg cgtttactta  24600
tttctatgct acacctggca gacggccatg ggcgtttggc agcagtgctt ggaggagtgc  24660
aacctcaagg agctgcagaa actgctaaag caaaacttga aggacctatg gacggccttc  24720
aacgagcgct ccgtggccgc gcacctggcg gacatcattt tccccgaacg cctgcttaaa  24780
accctgcaac agggtctgcc agacttcacc agtcaaagca tgttgcagaa ctttaggaac  24840
tttatcctag agcgctcagg aatcttgccc gccacctgct gtgcacttcc tagcgacttt  24900
gtgcccatta agtaccgcga atgccctccg ccgctttggg gccactgcta ccttctgcag  24960
ctagccaact accttgccta ccactctgac ataatggaag acgtgagcgg tgacggtcta  25020
ctggagtgtc actgtcgctg caacctatgc accccgcacc gctccctggt ttgcaattcg  25080
cagctgctta acgaaagtca aattatcggt acctttgagc tgcagggtcc ctcgcctgac  25140
gaaaagtccg cggctccggg gttgaaactc actccggggc tgtggacgtc ggcttacctt  25200
cgcaaatttg tacctgagga ctaccacgcc cacgagatta ggttctacga agaccaatcc  25260
cgcccgccta atgcggagct taccgcctgc gtcattaccc agggccacat tcttggccaa  25320
ttgcaagcca tcaacaaagc ccgccaagag tttctgctac gaaagggacg gggggtttac  25380
ttggaccccc agtccggcga ggagctcaac ccaatccccc cgccgccgca gccctatcag  25440
cagcagccgc gggcccttgc ttcccaggat ggcacccaaa aagaagctgc agctgccgcc  25500
gccacccacg gacgaggagg aatactggga cagtcaggca gaggaggttt tggacgagga  25560
ggaggaggac atgatggaag actgggagag cctagacgag gaagcttccg aggtcgaaga  25620
ggtgtcagac gaaacaccgt caccctcggt cgcattcccc tcgccggcgc cccagaaatc  25680
ggcaaccggt tccagcatgg ctacaacctc cgctcctcag gcgccgccgg cactgcccgt  25740
tcgccgaccc aaccgtagat gggacaccac tggaaccagg gccggtaagt ccaagcagcc  25800
gccgccgtta gcccaagagc aacaacagcg ccaaggctac cgctcatggc gcgggcacaa  25860
gaacgccata gttgcttgct tgcaagactg tgggggcaac atctccttcg cccgccgctt  25920
tcttctctac catcacggcg tggccttccc ccgtaacatc ctgcattact accgtcatct  25980
ctacagccca tactgcaccg gcggcagcgg cagcaacagc agcggccaca cagaagcaaa  26040
ggcgaccgga tagcaagact ctgacaaagc ccaagaaatc cacagcggcg gcagcagcag  26100
gaggaggagc gctgcgtctg gcgcccaacg aacccgtatc gacccgcgag cttagaaaca  26160
ggatttttcc cactctgtat gctatatttc aacagagcag ggccaagaa caagagctga  26220
aaataaaaaa caggtctctg cgatccctca cccgcagctg cctgtatcac aaaagcgaag  26280
atcagcttcg gcgcacgctg gaagacgcgg aggctctctt cagtaaatac tgcgcgctga  26340
ctcttaagga ctagtttcgc gccctttctc aaatttaagc gcgaaaacta cgtcatctcc  26400
agcggccaca cccggcgcca gcacctgttg tcagcgccat tatgagcaag gaaattccca  26460
cgccctacat gtggagttac cagccacaaa tgggacttgc ggctggagct gcccaagact  26520
```

```
actcaacccg aataaactac atgagcgcgg gaccccacat gatatcccgg gtcaacggaa  26580
tacgcgccca ccgaaaccga attctcctgg aacaggcggc tattaccacc acacctcgta  26640
ataaccttaa tccccgtagt tggcccgctg ccctggtgta ccaggaaagt cccgctccca  26700
ccactgtggt acttcccaga gacgcccagg ccgaagttca gatgactaac tcaggggcgc  26760
agcttgcggg cggctttcgt cacagggtgc ggtcgcccgg gcagggtata actcacctga  26820
caatcagagg gcgaggtatt cagctcaacg acgagtcggt gagctcctcg cttggtctcc  26880
gtccggacgg gacatttcag atcggcggcg ccggccgctc ttcattcacg cctcgtcagg  26940
caatcctaac tctgcagacc tcgtcctctg agccgcgctc tggaggcatt ggaactctgc  27000
aatttattga ggagtttgtg ccatcggtct actttaaccc cttctcggga cctcccggcc  27060
actatccgga tcaatttatt cctaactttg acgcggtaaa ggactcggcg gacggctacg  27120
actgaatgtt aagtggagag gcagagcaac tgcgcctgaa acacctggtc cactgtcgcc  27180
gccacaagtg ctttgcccgc gactccggtg agttttgcta ctttgaattg cccgaggatc  27240
atatcgaggg cccggcgcac ggcgtccggc ttaccgccca gggagagctt gcccgtagcc  27300
tgattcggga gtttacccag cgcccccctgc tagttgagcg ggacagggga ccctgtgttc  27360
tcactgtgat ttgcaactgt cctaaccctg gattacatca agatctttgt tgccatctct  27420
gtgctgagta taataaatac agaaattaaa atatactggg gctcctatcg ccatcctgta  27480
aacgccaccg tcttcacccg cccaagcaaa ccaaggcgaa ccttacctgg tacttttaac  27540
atctctccct ctgtgattta caacagtttc aacccagacg gagtgagtct acgagagaac  27600
ctctccgagc tcagctactc catcagaaaa aacaccaccc tccttacctg ccgggaacgt  27660
acgagtgcgt caccggccgc tgcaccacac ctaccgcctg accgtaaacc agactttttc  27720
cggacagacc tcaataactc tgtttaccag aacaggaggt gagcttagaa aacccttagg  27780
gtattaggcc aaaggcgcag ctactgtggg gtttatgaac aattcaagca actctacggg  27840
ctattctaat tcaggtttct ctagaatcgg ggttggggtt attctctgtc ttgtgattct  27900
ctttattctt atactaacgc ttctctgcct aaggctcgcc gcctgctgtg tgcacatttg  27960
catttattgt cagcttttta aacgctgggg tcgccaccca agatgattag gtacataatc  28020
ctaggtttac tcacccttgc gtcagcccac ggtaccaccc aaaaggtgga ttttaaggag  28080
ccagcctgta atgttacatt cgcagctgaa gctaatgagt gcaccactct tataaaatgc  28140
accacagaac atgaaaagct gcttattcgc cacaaaaaca aaattggcaa gtatgctgtt  28200
tatgctattt ggcagccagg tgacactaca gagtataatg ttacagtttt ccagggtaaa  28260
agtcataaaa cttttatgta tacttttcca ttttatgaaa tgtgcgacat taccatgtac  28320
atgagcaaac agtataagtt gtggccccca caaaattgtg tggaaaacac tggcactttc  28380
tgctgcactg ctatgctaat tacagtgctc gctttggtct gtaccctact ctatattaaa  28440
tacaaaagca gacgcagctt tattgaggaa aagaaaatgc cttaatttac taagttacaa  28500
agctaatgtc accactaact gctttactcg ctgcttgcaa aacaaattca aaaagttagc  28560
attataatta gaataggatt taaacccccc ggtcatttcc tgctcaatac cattcccctg  28620
aacaattgac tctatgtggg atatgctcca gcgctacaac cttgaagtca ggcttcctgg  28680
atgtcagcat ctgactttgg ccagcacctg tcccgcggat ttgttccagt ccaactacag  28740
cgacccaccc taacagagat gaccaacaca accaacgcgg ccgccgctac cggacttaca  28800
tctaccacaa atacacccca agtttctgcc tttgtcaata actgggataa cttgggcatg  28860
tggtggttct ccatagcgct tatgtttgta tgccttatta ttatgtggct catctgctgc  28920
```

-continued

```
ctaaagcgca aacgcgcccg accacccatc tatagtccca tcattgtgct acacccaaac  28980
aatgatggaa tccatagatt ggacggactg aaacacatgt tcttttctct tacagtatga  29040
ttaaatgaga catgattcct cgagttttta tattactgac ccttgttgcg cttttttttgt  29100
gcgtgctcca cattggctgc ggtttctcac atcgaagtag actgcattcc agccttcaca  29160
gtctatttgc tttacggatt tgtcaccctc acgctcatct gcagcctcat cactgtggtc  29220
atcgccttta tccagtgcat tgactgggtc tgtgtgcgct ttgcatatct cagacaccat  29280
ccccagtaca gggacaggac tatagctgag cttcttagaa ttctttaatt atgaaattta  29340
ctgtgacttt tctgctgatt atttgcaccc tatctgcgtt ttgttccccg acctccaagc  29400
ctcaaagaca tatatcatgc agattcactc gtatatggaa tattccaagt tgctacaatg  29460
aaaaaagcga tctttccgaa gcctggttat atgcaatcat ctctgttatg gtgttctgca  29520
gtaccatctt agccctagct atatatccct accttgacat tggctggaac gcaatagatg  29580
ccatgaacca cccaactttc cccgcgcccg ctatgcttcc actgcaacaa gttgttgccg  29640
gcggctttgt cccagccaat cagcctcgcc caccttctcc cacccccact gaaatcagct  29700
actttaatct aacaggagga gatgactgac accctagatc tagaaatgga cggaattatt  29760
acagagcagc gcctgctaga aagacgcagg gcagcggccg agcaacagcg catgaatcaa  29820
gagctccaag acatggttaa cttgcaccag tgcaaaaggg gtatcttttg tctggtaaag  29880
caggccaaag tcacctacga cagtaatacc accggacacc gccttagcta caagttgcca  29940
accaagcgtc agaaattggt ggtcatggtg ggagaaaagc ccattaccat aactcagcac  30000
tcggtagaaa ccgaaggctg cattcactca ccttgtcaag gacctgagga tctctgcacc  30060
cttattaaga ccctgtgcgg tctcaaagat cttattccct ttaactaata aaaaaaaata  30120
ataaagcatc acttacttaa aatcagttag caaatttctg tccagtttat tcagcagcac  30180
ctccttgccc tcctcccagc tctggtattg cagcttcctc ctggctgcaa actttctcca  30240
caatctaaat ggaatgtcag tttcctcctg ttcctgtcca tccgcaccca ctatcttcat  30300
gttgttgcag atgaagcgcg caagaccgtc tgaagatacc ttcaaccccg tgtatccata  30360
tgacacggaa accggtcctc caactgtgcc ttttcttact cctccctttg tatcccccaa  30420
tgggtttcaa gagagtcccc ctggggtact ctctttgcgc ctatccgaac ctctagttac  30480
ctccaatggc atgcttgcgc tcaaaatggg caacggcctc tctctggacg aggccggcaa  30540
ccttacctcc caaaatgtaa ccactgtgag cccacctctc aaaaaaacca agtcaaacat  30600
aaacctggaa atatctgcac ccctcacagt tacctcagaa gccctaactg tggctgccgc  30660
cgcacctcta atggtcgcgg gcaacacact caccatgcaa tcacaggccc cgctaaccgt  30720
gcacgactcc aaacttagca ttgccaccca aggacccctc acagtgtcag aaggaaagct  30780
agccctgcaa acatcaggcc ccctcaccac caccgatagc agtaccctta ctatcactgc  30840
ctcacccccct ctaactactg ccactggtag cttgggcatt gacttgaaag agcccattta  30900
tacacaaaat ggaaaactag gactaaagta cggggctcct ttgcatgtaa cagacgacct  30960
aaacactttg accgtagcaa ctggtccagg tgtgactatt aataatactt ccttgcaaac  31020
taaagttact ggagccttgg gttttgattc acaaggcaat atgcaactta atgtagcagg  31080
aggactaagg attgattctc aaaacagacg ccttatactt gatgttagtt atccgtttga  31140
tgctcaaaac caactaaatc taagactagg acagggccct ctttttataa actcagccca  31200
caacttggat attaactaca acaaaggcct ttacttgttt acagcttcaa acaattccaa  31260
```

-continued

```
aaagcttgag gttaacctaa gcactgccaa ggggttgatg tttgacgcta cagccatagc  31320
cattaatgca ggagatgggc ttgaatttgg ttcacctaat gcaccaaaca caaatcccct  31380
caaaacaaaa attggccatg gcctagaatt tgattcaaac aaggctatgg ttcctaaact  31440
aggaactggc cttagttttg acagcacagg tgccattaca gtaggaaaca aaaataatga  31500
taagctaact ttgtggacca caccagctcc atctcctaac tgtagactaa atgcagagaa  31560
agatgctaaa ctcactttgg tcttaacaaa atgtggcagt caaatacttg ctacagtttc  31620
agttttggct gttaaaggca gtttggctcc aatatctgga acagttcaaa gtgctcatct  31680
tattataaga tttgacgaaa atggagtgct actaaacaat tccttcctgg acccagaata  31740
ttggaacttt agaaatggag atcttactga aggcacagcc tatacaaacg ctgttggatt  31800
tatgcctaac ctatcagctt atccaaaatc tcacggtaaa actgccaaaa gtaacattgt  31860
cagtcaagtt tacttaaacg gagacaaaac taaacctgta acactaacca ttacactaaa  31920
cggtacacag gaaacaggag acacaactcc aagtgcatac tctatgtcat tttcatggga  31980
ctggtctggc cacaactaca ttaatgaaat atttgccaca tcctcttaca ctttttcata  32040
cattgcccaa gaataaagaa tcgtttgtgt tatgtttcaa cgtgtttatt tttcaattgc  32100
agaaaatttc aagtcatttt tcattcagta gtatagcccc accaccacat agcttataca  32160
gatcaccgta ccttaatcaa actcacagaa ccctagtatt caacctgcca cctccctccc  32220
aacacacaga gtacacagtc ctttctcccc ggctggcctt aaaaagcatc atatcatggg  32280
taacagacat attcttaggt gttatattcc acacggtttc ctgtcgagcc aaacgctcat  32340
cagtgatatt aataaactcc ccgggcagct cacttaagtt catgtcgctg tccagctgct  32400
gagccacagg ctgctgtcca acttgcggtt gcttaacggg cggcgaagga gaagtccacg  32460
cctacatggg ggtagagtca taatcgtgca tcaggatagg gcggtggtgc tgcagcagcg  32520
cgcgaataaa ctgctgccgc cgccgctccg tcctgcagga atacaacatg gcagtggtct  32580
cctcagcgat gattcgcacc gcccgcagca taaggcgcct tgtcctccgg gcacagcagc  32640
gcaccctgat ctcacttaaa tcagcacagt aactgcagca cagcaccaca atattgttca  32700
aaatcccaca gtgcaaggcg ctgtatccaa agctcatggc ggggaccaca gaacccacgt  32760
ggccatcata ccacaagcgc aggtagatta agtggcgacc cctcataaac acgctggaca  32820
taaacattac ctcttttggc atgttgtaat tcaccacctc ccggtaccat ataaacctct  32880
gattaaacat ggcgccatcc accaccatcc taaaccagct ggccaaaacc tgcccgccgg  32940
ctatacactg cagggaaccg ggactggaac aatgacagtg gagagcccag gactcgtaac  33000
catggatcat catgctcgtc atgatatcaa tgttggcaca acacaggcac acgtgcatac  33060
acttcctcag gattacaagc tcctcccgcg ttagaaccat atcccaggga acaacccatt  33120
cctgaatcag cgtaaatccc acactgcagg gaagacctcg cacgtaactc acgttgtgca  33180
ttgtcaaagt gttacattcg ggcagcagcg gatgatcctc cagtatggta gcgcgggttt  33240
ctgtctcaaa aggaggtaga cgatccctac tgtacggagt gcgccgagac aaccgagatc  33300
gtgttggtcg tagtgtcatg ccaaatggaa cgccggacgt agtcatattt cctgaagcaa  33360
aaccaggtgc gggcgtgaca aacagatctg cgtctccggt ctcgccgctt agatcgctct  33420
gtgtagtagt tgtagtatat ccactctctc aaagcatcca ggcgccccct ggcttcgggt  33480
tctatgtaaa ctccttcatg cgccgctgcc ctgataacat ccaccaccgc agaataagcc  33540
acacccagcc aacctacaca ttcgttctgc gagtcacaca cgggaggagc gggaagagct  33600
ggaagaacca tgtttttttt tttattccaa aagattatcc aaaacctcaa aatgaagatc  33660
```

```
tattaagtga acgcgctccc ctccggtggc gtggtcaaac tctacagcca aagaacagat  33720
aatggcattt gtaagatgtt gcacaatggc ttccaaaagg caaacggccc tcacgtccaa  33780
gtggacgtaa aggctaaacc cttcagggtg aatctcctct ataaacattc cagcaccttc  33840
aaccatgccc aaataattct catctcgcca ccttctcaat atatctctaa gcaaatcccg  33900
aatattaagt ccggccattg taaaaatctg ctccagagcg ccctccacct tcagcctcaa  33960
gcagcgaatc atgattgcaa aaattcaggt tcctcacaga cctgtataag attcaaaagc  34020
ggaacattaa caaaaatacc gcgatcccgt aggtcccttc gcagggccag ctgaacataa  34080
tcgtgcaggt ctgcacggac cagcgcggcc acttccccgc caggaaccat gacaaaagaa  34140
cccacactga ttatgacacg catactcgga gctatgctaa ccagcgtagc cccgatgtaa  34200
gcttgttgca tgggcggcga tataaaatgc aaggtgctgc tcaaaaaatc aggcaaagcc  34260
tcgcgcaaaa aagaaagcac atcgtagtca tgctcatgca gataaaggca ggtaagctcc  34320
ggaaccacca cagaaaaaga caccattttt ctctcaaaca tgtctgcggg tttctgcata  34380
aacacaaaat aaaataacaa aaaaacattt aaacattaga agcctgtctt acaacaggaa  34440
aaacaaccct tataagcata agacggacta cggccatgcc ggcgtgaccg taaaaaaact  34500
ggtcaccgtg attaaaaagc accaccgaca gctcctcggt catgtccgga gtcataatgt  34560
aagactcggt aaacacatca ggttgattca catcggtcag tgctaaaaag cgaccgaaat  34620
agcccggggg aatacatacc cgcaggcgta gagacaacat tacagccccc ataggaggta  34680
taacaaaatt aataggagag aaaaacacat aaacacctga aaaaccctcc tgcctaggca  34740
aaatagcacc ctcccgctcc agaacaacat acagcgcttc cacagcggca gccataacag  34800
tcagccttac cagtaaaaaa gaaaacctat taaaaaaaca ccactcgaca cggcaccagc  34860
tcaatcagtc acagtgtaaa aaagggccaa gtgcagagcg agtatatata ggactaaaaa  34920
atgacgtaac ggttaaagtc cacaaaaaac acccagaaaa ccgcacgcga acctacgccc  34980
agaaacgaaa gccaaaaaac ccacaacttc ctcaaatcgt cacttccgtt ttcccacgtt  35040
acgtcacttc ccattttaag aaaactacaa ttcccaacac atacaagtta ctccgcccta  35100
aaacctacgt cacccgcccc gttcccacgc ccgcgccac gtcacaaact ccaccccctc  35160
attatcatat tggcttcaat ccaaaataag gtatattatt gat                    35203
```

<210> SEQ ID NO 11
<211> LENGTH: 33093
<212> TYPE: DNA
<213> ORGANISM: Artificial sequence
<220> FEATURE:
<223> OTHER INFORMATION: Empty Ad5 vector sequence (repeats included)

<400> SEQUENCE: 11

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtacgtc tcgagcatgc atctaggcgg    480
```

-continued

```
ccgcatggca gaaattcgcg aattcgctag cgttaacgga tcctctagac gagatccgaa    540
cttgtttatt gcagcttata atggttacaa ataaagcaat agcatcacaa atttcacaaa    600
taaagcattt ttttcactgc attctagttg tggtttgtcc aaactcatca atgtatctta    660
tcatgtctag atctgtactg aaatgtgtgg gcgtggctta agggtgggaa agaatatata    720
aggtgggggt cttatgtagt tttgtatctg ttttgcagca gccgccgccg ccatgagcac    780
caactcgttt gatggaagca ttgtgagctc atatttgaca acgcgcatgc ccccatgggc    840
cggggtgcgt cagaatgtga tgggctccag cattgatggt cgccccgtcc tgcccgcaaa    900
ctctactacc ttgacctacg agaccgtgtc tggaacgccg ttggagactg cagcctccgc    960
cgccgcttca gccgctgcag ccaccgcccg cgggattgtg actgactttg ctttcctgag   1020
cccgcttgca agcagtgcag cttcccgttc atccgcccgc gatgacaagt tgacggctct   1080
tttggcacaa ttggattctt tgacccggga acttaatgtc gtttctcagc agctgttgga   1140
tctgcgccag caggtttctg ccctgaaggc ttcctcccct cccaatgcgg tttaaaacat   1200
aaataaaaaa ccagactctg tttggatttg gatcaagcaa gtgtcttgct gtctttattt   1260
aggggttttg cgcgcgcggt aggcccggga ccagcggtct cggtcgttga gggtcctgtg   1320
tatttttcc aggacgtggt aaaggtgact ctggatgttc agatacatgg gcataagccc   1380
gtctctgggg tggaggtagc accactgcag agcttcatgc tgcggggtgg tgttgtagat   1440
gatccagtcg tagcaggagc gctgggcgtg gtgcctaaaa atgtctttca gtagcaagct   1500
gattgccagg ggcaggccct tggtgtaagt gtttacaaag cggttaagct gggatgggtg   1560
catacgtggg gatatgagat gcatcttgga ctgtattttt aggttggcta tgttcccagc   1620
catatccctc cggggattca tgttgtgcag aaccaccagc acagtgtatc cggtgcactt   1680
gggaaatttg tcatgtagct tagaaggaaa tgcgtggaag aacttggaga cgcccttgtg   1740
acctccaaga ttttccatgc attcgtccat aatgatggca atgggcccac gggcggcggc   1800
ctgggcgaag atatttctgg gatcactaac gtcatagttg tgttccagga tgagatcgtc   1860
ataggccatt tttacaaagc gcgggcggag ggtgccagac tgcggtataa tggttccatc   1920
cggcccaggg gcgtagttac cctcacagat ttgcatttcc cacgctttga gttcagatgg   1980
ggggatcatg tctacctgcg gggcgatgaa gaaaacggtt tccggggtag gggagatcag   2040
ctgggaagaa agcaggttcc tgagcagctg cgacttaccg cagccggtgg gcccgtaaat   2100
cacacctatt accggctgca actggtagtt aagagagctg cagctgccgt catccctgag   2160
caggggggcc acttcgttaa gcatgtccct gactcgcatg ttttccctga ccaaatccgc   2220
cagaaggcgc tcgccgccca gcgatagcag ttcttgcaag gaagcaaagt ttttcaacgg   2280
tttgagaccg tccgccgtag gcatgctttt gagcgtttga ccaagcagtt ccaggcggtc   2340
ccacagctcg gtcacctgct ctacggcatc tcgatccagc atatctcctc gtttcgcggg   2400
ttggggcggc tttcgctgta cggcagtagt cggtgctcgt ccagacgggc cagggtcatg   2460
tctttccacg ggcgcagggt cctcgtcagc gtagtctggg tcacggtgaa ggggtgcgct   2520
ccgggctgcg cgctggccag ggtgcgcttg aggctggtcc tgctggtgct gaagcgctgc   2580
cggtcttcgc cctgcgcgtc ggccaggtag catttgacca tggtgtcata gtccagcccc   2640
tccgcggcgt ggcccttggc gcgcagcttg cccttggagg aggcgccgca cgaggggcag   2700
tgcagacttt tgagggcgta gagcttgggc gcgagaaata ccgattccgg ggagtaggca   2760
tccgcgccgc aggccccgca gacggtctcg cattccacga gccaggtgag ctctggccgt   2820
tcggggtcaa aaaccaggtt tcccccatgc tttttgatgc gtttcttacc tctggtttcc   2880
```

```
atgagccggt gtccacgctc ggtgacgaaa aggctgtccg tgtccccgta tacagacttg   2940
agaggcctgt cctcgagcgg tgttccgcgg tcctcctcgt atagaaactc ggaccactct   3000
gagacaaagg ctcgcgtcca ggccagcacg aaggaggcta agtgggaggg gtagcggtcg   3060
ttgtccacta gggggtccac tcgctccagg gtgtgaagac acatgtcgcc ctcttcggca   3120
tcaaggaagg tgattggttt gtaggtgtag gccacgtgac cgggtgttcc tgaagggggg   3180
ctataaaagg gggtgggggc gcgttcgtcc tcactctctt ccgcatcgct gtctgcgagg   3240
gccagctgtt ggggtgagta ctccctctga aaagcgggca tgacttctgc gctaagattg   3300
tcagtttcca aaaacgagga ggatttgata ttcacctggc ccgcggtgat gcctttgagg   3360
gtggccgcat ccatctggtc agaaaagaca atctttttgt tgtcaagctt ggtggcaaac   3420
gacccgtaga gggcgttgga cagcaacttg gcgatggagc gcagggtttg gtttttgtcg   3480
cgatcggcgc gctccttggc cgcgatgttt agctgcacgt attcgcgcgc aacgcaccgc   3540
cattcgggaa agacggtggt gcgctcgtcg ggcaccaggt gcacgcgcca accgcggttg   3600
tgcagggtga caaggtcaac gctggtggct acctctccgc gtaggcgctc gttggtccag   3660
cagaggcggc cgcccttgcg cgagcagaat ggcggtaggg ggtctagctg cgtctcgtcc   3720
ggggggtctg cgtccacggt aaagaccccg ggcagcaggc gcgcgtcgaa gtagtctatc   3780
ttgcatcctt gcaagtctag cgcctgctgc catgcgcggg cggcaagcgc gcgctcgtat   3840
gggttgagtg gggaccccca tggcatgggg tgggtgagcg cggaggcgta catgccgcaa   3900
atgtcgtaaa cgtagagggg ctctctgagt attccaagat atgtagggta gcatcttcca   3960
ccgcggatgc tggcgcgcac gtaatcgtat agttcgtgcg agggagcgag gaggtcggga   4020
ccgaggttgc tacgggcggg ctgctctgct cggaagacta tctgcctgaa gatggcatgt   4080
gagttggatg atatggttgg acgctggaag acgttgaagc tggcgtctgt gagacctacc   4140
gcgtcacgca cgaaggaggc gtaggagtcg cgcagcttgt tgaccagctc ggcggtgacc   4200
tgcacgtcta gggcgcagta gtccagggtt tccttgatga tgtcatactt atcctgtccc   4260
ttttttttcc acagctcgcg gttgaggaca aactcttcgc ggtctttcca gtactcttgg   4320
atcggaaacc cgtcggcctc cgaacggtaa gagcctagca tgtagaactg gttgacggcc   4380
tggtaggcgc agcatccctt ttctacgggt agcgcgtatg cctgcgcggc cttccggagc   4440
gaggtgtggg tgagcgcaaa ggtgtccctg accatgactt tgaggtactg gtatttgaag   4500
tcagtgtcgt cgcatccgcc ctgctcccag agcaaaaagt ccgtgcgctt tttggaacgc   4560
ggatttggca gggcgaaggt gacatcgttg aagagtatct ttcccgcgcg aggcataaag   4620
ttgcgtgtga tgcggaaggg tcccggcacc tcggaacggt tgttaattac ctgggcggcg   4680
agcacgatct cgtcaaagcc gttgatgttg tggcccacaa tgtaaagttc caagaagcgc   4740
gggatgccct tgatggaagg caattttta agttcctcgt aggtgagctc ttcaggggag   4800
ctgagcccgt gctctgaaag ggcccagtct gcaagatgag ggttggaagc gacgaatgag   4860
ctccacaggt cacgggccat tagcatttgc aggtggtcgc gaaaggtcct aaactggcga   4920
cctatggcca ttttttctgg ggtgatgcag tagaaggtaa gcgggtcttg ttcccagcgg   4980
tcccatccaa ggttcgcggc taggtctcgc gcggcagtca ctagaggctc atctccgccg   5040
aacttcatga ccagcatgaa gggcacgagc tgcttcccaa aggcccccat ccaagtatag   5100
gtctctacat cgtaggtgac aaagagacgc tcggtgcgag gatgcgagcc gatcgggaag   5160
aactggatct cccgccacca attggaggag tggctattga tgtggtgaaa gtagaagtcc   5220
```

-continued

```
ctgcgacggg ccgaacactc gtgctggctt ttgtaaaaac gtgcgcagta ctggcagcgg   5280
tgcacgggct gtacatcctg cacgaggttg acctgacgac cgcgcacaag gaagcagagt   5340
gggaatttga gcccctcgcc tggcgggttt ggctggtggt cttctacttc ggctgcttgt   5400
ccttgaccgt ctggctgctc gaggggagtt acggtggatc ggaccaccac gccgcgcgag   5460
cccaaagtcc agatgtccgc gcgcggcggt cggagcttga tgacaacatc gcgcagatgg   5520
gagctgtcca tggtctggag ctcccgcggc gtcaggtcag gcgggagctc ctgcaggttt   5580
acctcgcata gacgggtcag ggcgcgggct agatccaggt gatacctaat ttccaggggc   5640
tggttggtgg cggcgtcgat ggcttgcaag aggccgcatc cccgcggcgc gactacggta   5700
ccgcgcggcg ggcggtgggc cgcgggggtg tccttggatg atgcatctaa aagcggtgac   5760
gcgggcgagc ccccggaggt aggggggggct ccggacccgc cgggagaggg ggcaggggca   5820
cgtcggcgcc gcgcgcgggc aggagctggt gctgcgcgcg taggttgctg gcgaacgcga   5880
cgacgcggcg gttgatctcc tgaatctggc gcctctgcgt gaagacgacg ggcccggtga   5940
gcttgaacct gaaagagagt tcgacagaat caatttcggt gtcgttgacg gcggcctggc   6000
gcaaaatctc ctgcacgtct cctgagttgt cttgataggc gatctcggcc atgaactgct   6060
cgatctcttc ctcctggaga tctccgcgtc cggctcgctc cacggtggcg gcgaggtcgt   6120
tggaaatgcg ggccatgagc tgcgagaagg cgttgaggcc tccctcgttc cagacgcggc   6180
tgtagaccac gccccccttcg gcatcgcggg cgcgcatgac cacctgcgcg agattgagct   6240
ccacgtgccg ggcgaagacg gcgtagtttc gcaggcgctg aaagaggtag ttgagggtgg   6300
tggcggtgtg ttctgccacg aagaagtaca taacccagcg tcgcaacgtg gattcgttga   6360
tatcccccaa ggcctcaagg cgctccatgg cctcgtagaa gtccacggcg aagttgaaaa   6420
actgggagtt gcgcgccgac acggttaact cctcctccag aagacggatg agctcggcga   6480
cagtgtcgcg cacctcgcgc tcaaaggcta caggggcctc ttcttcttct tcaatctcct   6540
cttccataag ggcctcccct tcttcttctt ctggcggcgg tgggggaggg gggacacggc   6600
ggcgacgacg gcgcaccggg aggcggtcga caaagcgctc gatcatctcc ccgcggcgac   6660
ggcgcatggt ctcggtgacg gcgcggccgt tctcgcgggg gcgcagttgg aagacgccgc   6720
ccgtcatgtc ccggttatgg gttggcgggg ggctgccatg cggcagggat acggcgctaa   6780
cgatgcatct caacaattgt tgtgtaggta ctccgccgcc gagggacctg agcgagtccg   6840
catcgaccgg atcggaaaac ctctcgagaa aggcgtctaa ccagtcacag tcgcaaggta   6900
ggctgagcac cgtggcgggc ggcagcgggc ggcggtcggg gttgtttctg gcggaggtgc   6960
tgctgatgat gtaattaaag taggcggtct tgagacggcg gatggtcgac agaagcacca   7020
tgtccttggg tccggcctgc tgaatgcgca ggcggtcggc catgccccag gcttcgtttt   7080
gacatcggcg caggtctttg tagtagtctt gcatgagcct ttctaccggc acttcttctt   7140
ctccttcctc ttgtcctgca tctcttgcat ctatcgctgc ggcggcggcg gagtttggcc   7200
gtaggtggcg ccctcttcct cccatgcgtg tgaccccgaa gcccctcatc ggctgaagca   7260
gggctaggtc ggcgacaacg cgctcggcta atatggcctg ctgcacctgc gtgagggtag   7320
actggaagtc atccatgtcc acaaagcggt ggtatgcgcc cgtgttgatg gtgtaagtgc   7380
agttggccat aacggaccag ttaacggtct ggtgacccgg ctgcgagagc tcggtgtacc   7440
tgagacgcga gtaagccctc gagtcaaata cgtagtcgtt gcaagtccgc accaggtact   7500
ggtatcccac caaaaagtgc ggcggcggct ggcggtagag gggccagcgt agggtggccg   7560
gggctccggg ggcgagatct tccaacataa ggcgatgata tccgtagatg tacctggaca   7620
```

```
tccaggtgat gccggcggcg gtggtggagg cgcgcggaaa gtcgcggacg cggttccaga   7680
tgttgcgcag cggcaaaaag tgctccatgg tcgggacgct ctggccggtc aggcgcgcgc   7740
aatcgttgac gctctagacc gtgcaaaagg agagcctgta agcgggcact cttccgtggt   7800
ctggtggata aattcgcaag ggtatcatgg cggacgaccg gggttcgagc cccgtatccg   7860
gccgtccgcc gtgatccatg cggttaccgc ccgcgtgtcg aacccaggtg tgcgacgtca   7920
gacaacgggg gagtgctcct tttggcttcc ttccaggcgc ggcggctgct gcgctagctt   7980
ttttggccac tggccgcgcg cagcgtaagc ggttaggctg gaaagcgaaa gcattaagtg   8040
gctcgctccc tgtagccgga gggttatttt ccaagggttg agtcgcggga cccccggttc   8100
gagtctcgga ccggccggac tgcggcgaac gggggtttgc ctccccgtca tgcaagaccc   8160
cgcttgcaaa ttcctccgga aacagggacg agcccctttt ttgcttttcc cagatgcatc   8220
cggtgctgcg gcagatgcgc ccccctcctc agcagcggca agagcaagag cagcggcaga   8280
catgcagggc accctcccct cctcctaccg cgtcaggagg ggcgacatcc gcggttgacg   8340
cggcagcaga tggtgattac gaacccccgc ggcgccgggc ccggcactac ctggacttgg   8400
aggagggcga gggcctggcg cggctaggag cgccctctcc tgagcggcac ccaagggtgc   8460
agctgaagcg tgatacgcgt gaggcgtacg tgccgcggca gaacctgttt cgcgaccgcg   8520
agggagagga gcccgaggag atgcgggatc gaaagttcca cgcagggcgc gagctgcggc   8580
atggcctgaa tcgcgagcgg ttgctgcgcg aggaggactt tgagcccgac gcgcgaaccg   8640
ggattagtcc cgcgcgcgca cacgtggcgg ccgccgacct ggtaaccgca tacgagcaga   8700
cggtgaacca ggagattaac tttcaaaaaa gctttaacaa ccacgtgcgt acgcttgtgg   8760
cgcgcgagga ggtggctata ggactgatgc atctgtggga ctttgtaagc gcgctggagc   8820
aaaacccaaa tagcaagccg ctcatggcgc agctgttcct tatagtgcag cacagcaggg   8880
acaacgaggc attcagggat gcgctgctaa acatagtaga gcccgagggc cgctggctgc   8940
tcgatttgat aaacatcctg cagagcatag tggtgcagga gcgcagcttg agcctggctg   9000
acaaggtggc cgccatcaac tattccatgc ttagcctggg caagttttac gcccgcaaga   9060
tataccatac cccttacgtt cccatagaca aggaggtaaa gatcgagggg ttctacatgc   9120
gcatggcgct gaaggtgctt accttgagcg acgacctggg cgtttatcgc aacgagcgca   9180
tccacaaggc cgtgagcgtg agccggcggc gcgagctcag cgaccgcgag ctgatgcaca   9240
gcctgcaaag ggccctggct ggcacgggca gcggcgatag agaggccgag tcctactttg   9300
acgcgggcgc tgacctgcgc tgggccccaa gccgacgcgc cctggaggca gctggggccg   9360
gacctgggct ggcggtggca cccgcgcgcg ctggcaacgt cggcggcgtg gaggaatatg   9420
acgaggacga tgagtacgag ccagaggacg gcgagtacta agcggtgatg tttctgatca   9480
gatgatgcaa gacgcaacgg acccggcggt gcgggcggcg ctgcagagcc agccgtccgg   9540
ccttaactcc acggacgact ggcgccaggt catggaccgc atcatgtcgc tgactgcgcg   9600
caatcctgac gcgttccggc agcagccgca ggccaaccgg ctctccgcaa ttctggaagc   9660
ggtggtcccg gcgcgcgcaa accccacgca cgagaaggtg ctggcgatcg taaacgcgct   9720
ggccgaaaac agggccatcc ggcccgacga ggccggcctg gtctacgacg cgctgcttca   9780
gcgcgtggct cgttacaaca gcggcaacgt gcagaccaac ctggaccggc tggtggggga   9840
tgtgcgcgag gccgtggcgc agcgtgagcg cgcgcagcag cagggcaacc tgggctccat   9900
ggttgcacta aacgccttcc tgagtacaca gcccgccaac gtgccgcggg gacaggagga   9960
```

```
ctacaccaac tttgtgagcg cactgcggct aatggtgact gagacaccgc aaagtgaggt  10020
gtaccagtct gggccagact attttttcca gaccagtaga caaggcctgc agaccgtaaa  10080
cctgagccag gctttcaaaa acttgcaggg gctgtggggg gtgcgggctc ccacaggcga  10140
ccgcgcgacc gtgtctagct tgctgacgcc caactcgcgc ctgttgctgc tgctaatagc  10200
gcccttcacg gacagtggca gcgtgtcccg ggacacatac ctaggtcact tgctgacact  10260
gtaccgcgag gccataggtc aggcgcatgt ggacgagcat actttccagg agattacaag  10320
tgtcagccgc gcgctggggc aggaggacac gggcagcctg gaggcaaccc taaactacct  10380
gctgaccaac cggcggcaga agatcccctc gttgcacagt ttaaacagcg aggaggagcg  10440
cattttgcgc tacgtgcagc agagcgtgag ccttaacctg atgcgcgacg gggtaacgcc  10500
cagcgtggcg ctggacatga ccgcgcgcaa catggaaccg ggcatgtatg cctcaaaccg  10560
gccgtttatc aaccgcctaa tggactactt gcatcgcgcg gccgccgtga accccgagta  10620
tttcaccaat gccatcttga acccgcactg gctaccgccc cctggtttct acaccggggg  10680
attcgaggtg cccgagggta acgatggatt cctctgggac gacatagacg acagcgtgtt  10740
ttccccgcaa ccgcagaccc tgctagagtt gcaacagcgc gagcaggcag aggcggcgct  10800
gcgaaaggaa agcttccgca ggccaagcag cttgtccgat ctaggcgctg cggccccgcg  10860
gtcagatgct agtagcccat ttccaagctt gatagggtct cttaccagca ctcgcaccac  10920
ccgcccgcgc ctgctgggcg aggaggagta cctaaacaac tcgctgctgc agccgcagcg  10980
cgaaaaaaac ctgcctccgg catttcccaa caacgggata gagagcctag tggacaagat  11040
gagtagatgg aagacgtacg cgcaggagca cagggacgtg ccaggcccgc gcccgcccac  11100
ccgtcgtcaa aggcacgacc gtcagcgggg tctggtgtgg gaggacgatg actcggcaga  11160
cgacagcagc gtcctggatt tgggagggag tggcaacccg tttgcgcacc ttcgccccag  11220
gctggggaga atgttttaaa aaaaaaaaaa gcatgatgca aaataaaaaa ctcaccaagg  11280
ccatggcacc gagcgttggt ttcttgtatt tccccttagt atgcggcgcg cggcgatgta  11340
tgaggaaggt cctcctccct cctacgagag tgtggtgagc gcggcgccag tggcggcggc  11400
gctgggttct cccttcgatg ctcccctgga cccgccgttt gtgcctccgc ggtacctgcg  11460
gcctaccggg gggagaaaca gcatccgtta ctctgagttg gcacccctat tcgacaccac  11520
ccgtgtgtac ctggtggaca acaagtcaac ggatgtggca tccctgaact accagaacga  11580
ccacagcaac tttctgacca cggtcattca aaacaatgac tacagcccgg gggaggcaag  11640
cacacagacc atcaatcttg acgaccggtc gcactggggc ggcgacctga aaaccatcct  11700
gcataccaac atgccaaatg tgaacgagtt catgtttacc aataagttta aggcgcgggt  11760
gatggtgtcg cgcttgccta ctaaggacaa tcaggtggag ctgaaatacg agtgggtgga  11820
gttcacgctg cccgagggca actactccga gaccatgacc atagacctta tgaacaacgc  11880
gatcgtggag cactacttga aagtgggcag acagaacggg gttctggaaa gcgacatcgg  11940
ggtaaagttt gacacccgca acttcagact ggggtttgac cccgtcactg gtcttgtcat  12000
gcctggggta tatacaaacg aagccttcca tccagacatc attttgctgc caggatgcgg  12060
ggtggacttc acccacagcc gcctgagcaa cttgttgggc atccgcaagc ggcaaccctt  12120
ccaggagggc tttaggatca cctacgatga tctggagggt ggtaacattc ccgcactgtt  12180
ggatgtggac gcctaccagg cgagcttgaa agatgacacc gaacagggcg ggggtggcgc  12240
aggcggcagc aacagcagtg gcagcggcgc ggaagagaac tccaacgcgg cagccgcggc  12300
aatgcagccg gtggaggaca tgaacgatca tgccattcgc ggcgacacct ttgccacacg  12360
```

```
ggctgaggag aagcgcgctg aggccgaagc agcggccgaa gctgccgccc ccgctgcgca  12420

acccgaggtc gagaagcctc agaagaaacc ggtgatcaaa cccctgacag aggacagcaa  12480

gaaacgcagt tacaacctaa taagcaatga cagcaccttc acccagtacc gcagctggta  12540

ccttgcatac aactacggcg accctcagac cggaatccgc tcatggaccc tgctttgcac  12600

tcctgacgta acctgcggct cggagcaggt ctactggtcg ttgccagaca tgatgcaaga  12660

ccccgtgacc ttccgctcca cgcgccagat cagcaacttt ccggtggtgg gcgccgagct  12720

gttgcccgtg cactccaaga gcttctacaa cgaccaggcc gtctactccc aactcatccg  12780

ccagtttacc tctctgaccc acgtgttcaa tcgctttccc gagaaccaga ttttggcgcg  12840

cccgccagcc cccaccatca ccaccgtcag tgaaaacgtt cctgctctca cagatcacgg  12900

gacgctaccg ctgcgcaaca gcatcggagg agtccagcga gtgaccatta ctgacgccag  12960

acgccgcacc tgcccctacg tttacaaggc cctgggcata gtctcgccgc gcgtcctatc  13020

gagccgcact ttttgagcaa gcatgtccat ccttatatcg cccagcaata acacaggctg  13080

gggcctgcgc ttcccaagca agatgtttgg cggggccaag aagcgctccg accaacaccc  13140

agtgcgcgtg cgcgggcact accgcgcgcc ctggggcgcg cacaaacgcg gccgcactgg  13200

gcgcaccacc gtcgatgacg ccatcgacgc ggtggtggag gaggcgcgca actacacgcc  13260

cacgccgcca ccagtgtcca cagtggacgc ggccattcag accgtggtgc gcggagcccg  13320

gcgctatgct aaaatgaaga gacggcggag gcgcgtagca cgtcgccacc gccgccgacc  13380

cggcactgcc gcccaacgcg cggcggcggc cctgcttaac cgcgcacgtc gcaccggccg  13440

acgggcggcc atgcgggccg ctcgaaggct ggccgcgggt attgtcactg tgccccccag  13500

gtccaggcga cgagcggccg ccgcagcagc cgcggccatt agtgctatga ctcagggtcg  13560

caggggcaac gtgtattggg tgcgcgactc ggttagcggc ctgcgcgtgc ccgtgcgcac  13620

ccgcccccg cgcaactaga ttgcaagaaa aaactactta gactcgtact gttgtatgta  13680

tccagcggcg gcggcgcgca acgaagctat gtccaagcgc aaaatcaaag aagagatgct  13740

ccaggtcatc gcgccggaga tctatggccc cccgaagaag gaagagcagg attacaagcc  13800

ccgaaagcta aagcgggtca aaaagaaaaa gaaagatgat gatgatgaac ttgacgacga  13860

ggtggaactg ctgcacgcta ccgcgcccag gcgacgggta cagtggaaag gtcgacgcgt  13920

aaaacgtgtt ttgcgacccg gcaccaccgt agtctttacg cccggtgagc gctccacccg  13980

cacctacaag cgcgtgtatg atgaggtgta cggcgacgag gacctgcttg agcaggccaa  14040

cgagcgcctc ggggagtttg cctacggaaa gcggcataag gacatgctgg cgttgccgct  14100

ggacgagggc aacccaacac ctagcctaaa gcccgtaaca ctgcagcagg tgctgcccgc  14160

gcttgcaccg tccgaagaaa agcgcggcct aaagcgcgag tctggtgact tggcacccac  14220

cgtgcagctg atggtaccca agcgccagcg actggaagat gtcttggaaa aaatgaccgt  14280

ggaacctggg ctggagcccg aggtccgcgt gcggccaatc aagcaggtgg cgccgggact  14340

gggcgtgcag accgtggacg ttcagatacc cactaccagt agcaccagta ttgccaccgc  14400

cacagagggc atggagacac aaacgtcccc ggttgcctca gcggtggcgg atgccgcggt  14460

gcaggcggtc gctgcggccg cgtccaagac ctctacggag gtgcaaacgg acccgtggat  14520

gtttcgcgtt tcagcccccc ggcgcccgcg ccgttcgagg aagtacggcg ccgccagcgc  14580

gctactgccc gaatatgccc tacatccttc cattgcgcct acccccggct atcgtggcta  14640

cacctaccgc cccagaagac gagcaactac ccgacgccga accaccactg gaacccgccg  14700
```

```
ccgccgtcgc cgtcgccagc ccgtgctggc cccgatttcc gtgcgcaggg tggctcgcga  14760

aggaggcagg accctggtgc tgccaacagc gcgctaccac cccagcatcg tttaaaagcc  14820

ggtctttgtg gttcttgcag atatggccct cacctgccgc ctccgtttcc cggtgccggg  14880

attccgagga agaatgcacc gtaggagggg catggccggc cacggcctga cgggcggcat  14940

gcgtcgtgcg caccaccggc ggcggcgcgc gtcgcaccgt cgcatgcgcg gcggtatcct  15000

gcccctcctt attccactga tcgccgcggc gattggcgcc gtgcccggaa ttgcatccgt  15060

ggccttgcag gcgcagagac actgattaaa aacaagttgc atgtggaaaa atcaaaataa  15120

aaagtctgga ctctcacgct cgcttggtcc tgtaactatt ttgtagaatg gaagacatca  15180

actttgcgtc tctggccccg cgacacggct cgcgcccgtt catgggaaac tggcaagata  15240

tcggcaccag caatatgagc ggtggcgcct tcagctgggg ctcgctgtgg agcggcatta  15300

aaaatttcgg ttccaccgtt aagaactatg gcagcaaggc ctggaacagc agcacaggcc  15360

agatgctgag ggataagttg aaagagcaaa atttccaaca aaaggtggta gatggcctgg  15420

cctctggcat tagcggggtg gtggacctgg ccaaccaggc agtgcaaaat aagattaaca  15480

gtaagcttga tccccgccct cccgtagagg agcctccacc ggccgtggag acagtgtctc  15540

cagaggggcg tggcgaaaag cgtccgcgcc ccgacaggga agaaactctg gtgacgcaaa  15600

tagacgagcc tccctcgtac gaggaggcac taaagcaagg cctgcccacc acccgtccca  15660

tcgcgcccat ggctaccgga gtgctgggcc agcacacacc cgtaacgctg gacctgcctc  15720

cccccgccga cacccagcag aaacctgtgc tgccaggccc gaccgccgtt gttgtaaccc  15780

gtcctagccg cgcgtccctg cgccgcgccg ccagcggtcc gcgatcgttg cggcccgtag  15840

ccagtggcaa ctggcaaagc acactgaaca gcatcgtggg tctgggggtg caatccctga  15900

agcgccgacg atgcttctga tagctaacgt gtcgtatgtg tgtcatgtat gcgtccatgt  15960

cgccgccaga ggagctgctg agccgccgcg cgcccgcttt ccaagatggc taccccttcg  16020

atgatgccgc agtggtctta catgcacatc tcgggccagg acgcctcgga gtacctgagc  16080

cccgggctgg tgcagtttgc ccgcgccacc gagacgtact tcagcctgaa taacaagttt  16140

agaaacccca cggtggcgcc tacgcacgac gtgaccacag accggtccca gcgtttgacg  16200

ctgcggttca tccctgtgga ccgtgaggat actgcgtact cgtacaaggc gcggttcacc  16260

ctagctgtgg gtgataaccg tgtgctggac atggcttcca cgtactttga catccgcggc  16320

gtgctggaca ggggccctac ttttaagccc tactctggca ctgcctacaa cgccctggct  16380

cccaagggtg ccccaaatcc ttgcgaatgg gatgaagctg ctactgctct tgaaataaac  16440

ctagaagaag aggacgatga caacgaagac gaagtagacg agcaagctga gcagcaaaaa  16500

actcacgtat ttgggcaggc gccttattct ggtataaata ttacaaagga gggtattcaa  16560

ataggtgtcg aaggtcaaac acctaaatat gccgataaaa catttcaacc tgaacctcaa  16620

ataggagaat ctcagtggta cgaaacagaa attaatcatg cagctgggag agtcctaaaa  16680

aagactaccc caatgaaacc atgttacggt tcatatgcaa aacccacaaa tgaaaatgga  16740

gggcaaggca ttcttgtaaa gcaacaaaat ggaaagctag aaagtcaagt ggaaatgcaa  16800

tttttctcaa ctactgaggc agccgcaggc aatggtgata acttgactcc taaagtggta  16860

ttgtacagtg aagatgtaga tatagaaacc ccagacactc atatttctta catgcccact  16920

attaaggaag gtaactcacg agaactaatg ggccaacaat ctatgcccaa caggcctaat  16980

tacattgctt ttagggacaa ttttattggt ctaatgtatt acaacagcac gggtaatatg  17040

ggtgttctgg cgggccaagc atcgcagttg aatgctgttg tagatttgca agacagaaac  17100
```

```
acagagcttt cataccagct tttgcttgat tccattggtg atagaaccag gtacttttct  17160
atgtggaatc aggctgttga cagctatgat ccagatgtta gaattattga aaatcatgga  17220
actgaagatg aacttccaaa ttactgcttt ccactgggag gtgtgattaa tacagagact  17280
cttaccaagg taaaacctaa aacaggtcag gaaaatggat gggaaaaaga tgctacagaa  17340
ttttcagata aaaatgaaat aagagttgga aataattttg ccatggaaat caatctaaat  17400
gccaacctgt ggagaaattt cctgtactcc aacatagcgc tgtatttgcc cgacaagcta  17460
aagtacagtc cttccaacgt aaaaatttct gataacccaa acacctacga ctacatgaac  17520
aagcgagtgg tggctcccgg gctagtggac tgctacatta accttggagc acgctggtcc  17580
cttgactata tggacaacgt caacccattt aaccaccacc gcaatgctgg cctgcgctac  17640
cgctcaatgt tgctgggcaa tggtcgctat gtgcccttcc acatccaggt gcctcagaag  17700
ttctttgcca ttaaaaacct ccttctcctg ccgggctcat acacctacga gtggaacttc  17760
aggaaggatg ttaacatggt tctgcagagc tccctaggaa atgacctaag ggttgacgga  17820
gccagcatta agtttgatag catttgcctt tacgccacct tcttccccat ggcccacaac  17880
accgcctcca cgcttgaggc catgcttaga aacgacacca acgaccagtc ctttaacgac  17940
tatctctccg ccgccaacat gctctaccct atacccgcca acgctaccaa cgtgcccata  18000
tccatcccct cccgcaactg ggcggctttc cgcggctggg ccttcacgcg ccttaagact  18060
aaggaaaccc catcactggg ctcgggctac gacccttatt acacctactc tggctctata  18120
ccctacctag atggaacctt ttacctcaac cacaccttta agaaggtggc cattaccttt  18180
gactcttctg tcagctggcc tggcaatgac cgcctgctta cccccaacga gtttgaaatt  18240
aagcgctcag ttgacgggga gggttacaac gttgcccagt gtaacatgac caaagactgg  18300
ttcctggtac aaatgctagc taactataac attggctacc agggcttcta tatcccagag  18360
agctacaagg accgcatgta ctccttcttt agaaacttcc agcccatgag ccgtcaggtg  18420
gtggatgata ctaaatacaa ggactaccaa caggtgggca tcctacacca acacaacaac  18480
tctggatttg ttggctacct tgcccccacc atgcgcgaag gacaggccta ccctgctaac  18540
ttcccctatc cgcttatagg caagaccgca gttgacagca ttacccagaa aaagtttctt  18600
tgcgatcgca ccctttggcg catcccattc tccagtaact ttatgtccat gggcgcactc  18660
acagacctgg gccaaaacct tctctacgcc aactccgccc acgcgctaga catgactttt  18720
gaggtggatc ccatggacga gcccaccctt ctttatgttt tgtttgaagt ctttgacgtg  18780
gtccgtgtgc accagccgca ccgcggcgtc atcgaaaccg tgtacctgcg cacgcccttc  18840
tcggccggca acgccacaac ataaagaagc aagcaacatc aacaacagct gccgccatgg  18900
gctccagtga gcaggaactg aaagccattg tcaaagatct tggttgtggg ccatattttt  18960
tgggcaccta tgacaagcgc tttccaggct ttgtttctcc acacaagctc gcctgcgcca  19020
tagtcaatac ggccggtcgc gagactgggg gcgtacactg gatggccttt gcctggaacc  19080
cgcactcaaa aacatgctac ctctttgagc cctttggctt ttctgaccag cgactcaagc  19140
aggtttacca gtttgagtac gagtcactcc tgcgccgtag cgccattgct tcttcccccg  19200
accgctgtat aacgctggaa aagtccaccc aaagcgtaca ggggcccaac tcggccgcct  19260
gtggactatt ctgctgcatg tttctccacg cctttgccaa ctggccccaa actcccatgg  19320
atcacaaccc caccatgaac cttattaccg gggtacccaa ctccatgctc aacagtcccc  19380
aggtacagcc caccctgcgt cgcaaccagg aacagctcta cagcttcctg gagcgccact  19440
```

```
cgccctactt ccgcagccac agtgcgcaga ttaggagcgc cacttctttt tgtcacttga  19500
aaaacatgta aaaataatgt actagagaca ctttcaataa aggcaaatgc ttttatttgt  19560
acactctcgg gtgattattt acccccaccc ttgccgtctg cgccgtttaa aaatcaaagg  19620
ggttctgccg cgcatcgcta tgcgccactg gcagggacac gttgcgatac tggtgtttag  19680
tgctccactt aaactcaggc acaaccatcc gcggcagctc ggtgaagttt tcactccaca  19740
ggctgcgcac catcaccaac gcgtttagca ggtcgggcgc cgatatcttg aagtcgcagt  19800
tggggcctcc gccctgcgcg cgcgagttgc gatacacagg gttgcagcac tggaacacta  19860
tcagcgccgg gtggtgcacg ctggccagca cgctcttgtc ggagatcaga tccgcgtcca  19920
ggtcctccgc gttgctcagg gcgaacggag tcaactttgg tagctgcctt cccaaaaagg  19980
gcgcgtgccc aggctttgag ttgcactcgc accgtagtgg catcaaaagg tgaccgtgcc  20040
cggtctgggc gttaggatac agcgcctgca taaaagcctt gatctgctta aaagccacct  20100
gagcctttgc gccttcagag aagaacatgc cgcaagactt gccggaaaac tgattggccg  20160
gacaggccgc gtcgtgcacg cagcaccttg cgtcggtgtt ggagatctgc accacatttc  20220
ggccccaccg gttcttcacg atcttggcct tgctagactg ctccttcagc gcgcgctgcc  20280
cgttttcgct cgtcacatcc atttcaatca cgtgctcctt atttatcata atgcttccgt  20340
gtagacactt aagctcgcct tcgatctcag cgcagcggtg cagccacaac gcgcagcccg  20400
tgggctcgtg atgcttgtag gtcacctctg caaacgactg caggtacgcc tgcaggaatc  20460
gccccatcat cgtcacaaag gtcttgttgc tggtgaaggt cagctgcaac ccgcggtgct  20520
cctcgttcag ccaggtcttg catacggccg ccagagcttc cacttggtca ggcagtagtt  20580
tgaagttcgc ctttagatcg ttatccacgt ggtacttgtc catcagcgcg cgcgcagcct  20640
ccatgccctt ctcccacgca gacacgatcg gcacactcag cgggttcatc accgtaattt  20700
cactttccgc ttcgctgggc tcttcctctt cctcttgcgt ccgcatacca cgcgccactg  20760
ggtcgtcttc attcagccgc cgcactgtgc gcttacctcc tttgccatgc ttgattagca  20820
ccggtgggtt gctgaaaccc accatttgta gcgccacatc ttctctttct tcctcgctgt  20880
ccacgattac ctctggtgat ggcgggcgct cgggcttggg agaagggcgc ttcttttttct  20940
tcttgggcgc aatggccaaa tccgccgccg aggtcgatgg ccgcgggctg ggtgtgcgcg  21000
gcaccagcgc gtcttgtgat gagtcttcct cgtcctcgga ctcgatacgc cgcctcatcc  21060
gcttttttgg gggcgcccgg ggaggcggcg gcgacgggga cggggacgac acgtcctcca  21120
tggttggggg acgtcgcgcc gcaccgcgtc cgcgctcggg ggtggtttcg cgctgctcct  21180
cttcccgact ggccatttcc ttctcctata ggcagaaaaa gatcatggag tcagtcgaga  21240
agaaggacag cctaaccgcc ccctctgagt tcgccaccac cgcctccacc gatgccgcca  21300
acgcgcctac caccttcccc gtcgaggcac ccccgcttga ggaggaggaa gtgattatcg  21360
agcaggaccc aggttttgta agcgaagacg acgaggaccg ctcagtacca acagaggata  21420
aaaagcaaga ccaggacaac gcagaggcaa acgaggaaca agtcgggcgg ggggacgaaa  21480
ggcatggcga ctacctagat gtgggagacg acgtgctgtt gaagcatctg cagcgccagt  21540
gcgccattat ctgcgacgcg ttgcaagagc gcagcgatgt gcccctcgcc atagcggatg  21600
tcagccttgc ctacgaacgc cacctattct caccgcgcgt accccccaaa cgccaagaaa  21660
acggcacatg cgagcccaac ccgcgcctca acttctaccc cgtatttgcc gtgccagagg  21720
tgcttgccac ctatcacatc tttttccaaa actgcaagat acccctatcc tgccgtgcca  21780
accgcagccg agcggacaag cagctggcct tgcggcaggg cgctgtcata cctgatatcg  21840
```

```
cctcgctcaa cgaagtgcca aaaatctttg agggtcttgg acgcgacgag aagcgcgcgg  21900
caaacgctct gcaacaggaa aacagcgaaa atgaaagtca ctctggagtg ttggtggaac  21960
tcgagggtga caacgcgcgc ctagccgtac taaaacgcag catcgaggtc acccactttg  22020
cctacccggc acttaaccta ccccccaagg tcatgagcac agtcatgagt gagctgatcg  22080
tgcgccgtgc gcagcccctg gagagggatg caaatttgca agaacaaaca gaggagggcc  22140
tacccgcagt tggcgacgag cagctagcgc gctggcttca aacgcgcgag cctgccgact  22200
tggaggagcg acgcaaacta atgatggccg cagtgctcgt taccgtggag cttgagtgca  22260
tgcagcggtt ctttgctgac ccggagatgc agcgcaagct agaggaaaca ttgcactaca  22320
cctttcgaca gggctacgta cgccaggcct gcaagatctc caacgtggag ctctgcaacc  22380
tggtctccta ccttggaatt ttgcacgaaa accgccttgg gcaaaacgtg cttcattcca  22440
cgctcaaggg cgaggcgcgc cgcgactacg tccgcgactg cgtttactta tttctatgct  22500
acacctggca gacggccatg ggcgtttggc agcagtgctt ggaggagtgc aacctcaagg  22560
agctgcagaa actgctaaag caaaacttga aggacctatg gacggccttc aacgagcgct  22620
ccgtggccgc gcacctggcg gacatcattt tccccgaacg cctgcttaaa accctgcaac  22680
agggtctgcc agacttcacc agtcaaagca tgttgcagaa ctttaggaac tttatcctag  22740
agcgctcagg aatcttgccc gccacctgct gtgcacttcc tagcgacttt gtgcccatta  22800
agtaccgcga atgccctccg ccgctttggg gccactgcta ccttctgcag ctagccaact  22860
accttgccta ccactctgac ataatggaag acgtgagcgg tgacggtcta ctggagtgtc  22920
actgtcgctg caacctatgc accccgcacc gctccctggt ttgcaattcg cagctgctta  22980
acgaaagtca aattatcggt acctttgagc tgcagggtcc ctcgcctgac gaaaagtccg  23040
cggctccggg gttgaaactc actccggggc tgtggacgtc ggcttacctt cgcaaatttg  23100
tacctgagga ctaccacgcc cacgagatta ggttctacga agaccaatcc cgcccgccta  23160
atgcggagct taccgcctgc gtcattaccc agggccacat tcttggccaa ttgcaagcca  23220
tcaacaaagc ccgccaagag tttctgctac gaaagggacg gggggtttac ttggaccccc  23280
agtccggcga ggagctcaac ccaatccccc cgccgccgca gccctatcag cagcagccgc  23340
gggcccttgc ttcccaggat ggcacccaaa aagaagctgc agctgccgcc gccacccacg  23400
gacgaggagg aatactggga cagtcaggca gaggaggttt tggacgagga ggaggaggac  23460
atgatggaag actgggagag cctagacgag gaagcttccg aggtcgaaga ggtgtcagac  23520
gaaacaccgt caccctcggt cgcattcccc tcgccggcgc cccagaaatc ggcaaccggt  23580
tccagcatgg ctacaacctc cgctcctcag gcgccgccgg cactgcccgt tcgccgaccc  23640
aaccgtagat gggacaccac tggaaccagg gccggtaagt ccaagcagcc gccgccgtta  23700
gcccaagagc aacaacagcg ccaaggctac cgctcatggc gcgggcacaa gaacgccata  23760
gttgcttgct tgcaagactg tgggggcaac atctccttcg cccgccgctt tcttctctac  23820
catcacggcg tggccttccc ccgtaacatc ctgcattact accgtcatct ctacagccca  23880
tactgcaccg gcggcagcgg cagcaacagc agcggccaca cagaagcaaa ggcgaccgga  23940
tagcaagact ctgacaaagc ccaagaaatc cacagcggcg gcagcagcag gaggaggagc  24000
gctgcgtctg gcgcccaacg aacccgtatc gacccgcgag cttagaaaca ggatttttcc  24060
cactctgtat gctatatttc aacagagcag gggccaagaa caagagctga aaataaaaaa  24120
caggtctctg cgatccctca cccgcagctg cctgtatcac aaaagcgaag atcagcttcg  24180
```

```
gcgcacgctg gaagacgcgg aggctctctt cagtaaatac tgcgcgctga ctcttaagga  24240
ctagtttcgc gccctttctc aaatttaagc gcgaaaacta cgtcatctcc agcggccaca  24300
cccggcgcca gcacctgttg tcagcgccat tatgagcaag gaaattccca cgccctacat  24360
gtggagttac cagccacaaa tgggacttgc ggctggagct gcccaagact actcaacccg  24420
aataaactac atgagcgcgg gaccccacat gatatcccgg gtcaacggaa tacgcgccca  24480
ccgaaaccga attctcctgg aacaggcggc tattaccacc acacctcgta ataaccttaa  24540
tccccgtagt tggcccgctg ccctggtgta ccaggaaagt cccgctccca ccactgtggt  24600
acttcccaga gacgcccagg ccgaagttca gatgactaac tcaggggcgc agcttgcggg  24660
cggctttcgt cacagggtgc ggtcgcccgg gcagggtata actcacctga caatcagagg  24720
gcgaggtatt cagctcaacg acgagtcggt gagctcctcg cttggtctcc gtccggacgg  24780
gacatttcag atcggcggcg ccggccgctc ttcattcacg cctcgtcagg caatcctaac  24840
tctgcagacc tcgtcctctg agccgcgctc tggaggcatt ggaactctgc aatttattga  24900
ggagtttgtg ccatcggtct actttaaccc cttctcggga cctcccggcc actatccgga  24960
tcaatttatt cctaactttg acgcggtaaa ggactcggcg gacggctacg actgaatgtt  25020
aagtggagag gcagagcaac tgcgcctgaa acacctggtc cactgtcgcc gccacaagtg  25080
ctttgcccgc gactccggtg agttttgcta ctttgaattg cccgaggatc atatcgaggg  25140
cccggcgcac ggcgtccggc ttaccgccca gggagagctt gcccgtagcc tgattcggga  25200
gtttacccag cgcccccctgc tagttgagcg ggacagggga ccctgtgttc tcactgtgat  25260
ttgcaactgt cctaaccctg gattacatca agatctttgt tgccatctct gtgctgagta  25320
taataaatac agaaattaaa atatactggg gctcctatcg ccatcctgta aacgccaccg  25380
tcttcacccg cccaagcaaa ccaaggcgaa ccttacctgg tacttttaac atctctccct  25440
ctgtgattta caacagtttc aacccagacg gagtgagtct acgagagaac ctctccgagc  25500
tcagctactc catcagaaaa aacaccaccc tccttacctg ccgggaacgt acgagtgcgt  25560
caccggccgc tgcaccacac ctaccgcctg accgtaaacc agacttttc cggacagacc  25620
tcaataactc tgtttaccag aacaggaggt gagcttagaa aaccccttagg gtattaggcc  25680
aaaggcgcag ctactgtggg gtttatgaac aattcaagca actctacggg ctattctaat  25740
tcaggtttct ctagaatcgg ggttggggtt attctctgtc ttgtgattct ctttattctt  25800
atactaacgc ttctctgcct aaggctcgcc gcctgctgtg tgcacatttg catttattgt  25860
cagcttttta aacgctgggg tcgccaccca agatgattag gtacataatc ctaggtttac  25920
tcacccttgc gtcagcccac ggtaccaccc aaaaggtgga ttttaaggag ccagcctgta  25980
atgttacatt cgcagctgaa gctaatgagt gcaccactct tataaaatgc accacagaac  26040
atgaaaagct gcttattcgc cacaaaaaca aaattggcaa gtatgctgtt tatgctattt  26100
ggcagccagg tgacactaca gagtataatg ttacagtttt ccagggtaaa agtcataaaa  26160
cttttatgta tacttttcca ttttatgaaa tgtgcgacat taccatgtac atgagcaaac  26220
agtataagtt gtggccccca caaaattgtg tggaaaacac tggcactttc tgctgcactg  26280
ctatgctaat tacagtgctc gctttggtct gtaccctact ctatattaaa tacaaaagca  26340
gacgcagctt tattgaggaa aagaaaatgc cttaatttac taagttacaa agctaatgtc  26400
accactaact gctttactcg ctgcttgcaa aacaaattca aaaagttagc attataatta  26460
gaataggatt taaacccccc ggtcatttcc tgctcaatac cattcccctg aacaattgac  26520
tctatgtggg atatgctcca gcgctacaac cttgaagtca ggcttcctgg atgtcagcat  26580
```

```
ctgactttgg ccagcacctg tcccgcggat ttgttccagt ccaactacag cgacccaccc  26640
taacagagat gaccaacaca accaacgcgg ccgccgctac cggacttaca tctaccacaa  26700
atacacccca agtttctgcc tttgtcaata actgggataa cttgggcatg tggtggttct  26760
ccatagcgct tatgtttgta tgccttatta ttatgtggct catctgctgc ctaaagcgca  26820
aacgcgcccg accacccatc tatagtccca tcattgtgct acacccaaac aatgatggaa  26880
tccatagatt ggacggactg aaacacatgt tcttttctct tacagtatga ttaaatgaga  26940
catgattcct cgagttttta tattactgac ccttgttgcg cttttttttgt gcgtgctcca  27000
cattggctgc ggtttctcac atcgaagtag actgcattcc agccttcaca gtctatttgc  27060
tttacggatt tgtcaccctc acgctcatct gcagcctcat cactgtggtc atcgccttta  27120
tccagtgcat tgactgggtc tgtgtgcgct ttgcatatct cagacaccat ccccagtaca  27180
gggacaggac tatagctgag cttcttagaa ttctttaatt atgaaattta ctgtgacttt  27240
tctgctgatt atttgcaccc tatctgcgtt ttgttccccg acctccaagc ctcaaagaca  27300
tatatcatgc agattcactc gtatatggaa tattccaagt tgctacaatg aaaaaagcga  27360
tctttccgaa gcctggttat atgcaatcat ctctgttatg gtgttctgca gtaccatctt  27420
agccctagct atatatccct accttgacat tggctggaac gcaatagatg ccatgaacca  27480
cccaactttc cccgcgcccg ctatgcttcc actgcaacaa gttgttgccg gcggctttgt  27540
cccagccaat cagcctcgcc caccttctcc cacccccact gaaatcagct actttaatct  27600
aacaggagga gatgactgac accctagatc tagaaatgga cggaattatt acagagcagc  27660
gcctgctaga aagacgcagg gcagcggccg agcaacagcg catgaatcaa gagctccaag  27720
acatggttaa cttgcaccag tgcaaaaggg gtatcttttg tctggtaaag caggccaaag  27780
tcacctacga cagtaatacc accggacacc gccttagcta caagttgcca accaagcgtc  27840
agaaattggt ggtcatggtg ggagaaaagc ccattaccat aactcagcac tcggtagaaa  27900
ccgaaggctg cattcactca ccttgtcaag gacctgagga tctctgcacc cttattaaga  27960
ccctgtgcgg tctcaaagat cttattccct ttaactaata aaaaaaaata ataaagcatc  28020
acttacttaa aatcagttag caaatttctg tccagtttat tcagcagcac ctccttgccc  28080
tcctcccagc tctggtattg cagcttcctc ctggctgcaa actttctcca caatctaaat  28140
ggaatgtcag tttcctcctg ttcctgtcca tccgcaccca ctatcttcat gttgttgcag  28200
atgaagcgcg caagaccgtc tgaagatacc ttcaaccccg tgtatccata tgacacggaa  28260
accggtcctc caactgtgcc ttttcttact cctccctttg tatcccccaa tgggtttcaa  28320
gagagtcccc ctggggtact ctctttgcgc ctatccgaac ctctagttac ctccaatggc  28380
atgcttgcgc tcaaaatggg caacggcctc tctctggacg aggccggcaa ccttacctcc  28440
caaaatgtaa ccactgtgag cccacctctc aaaaaaacca agtcaaacat aaacctggaa  28500
atatctgcac ccctcacagt tacctcagaa gccctaactg tggctgccgc cgcacctcta  28560
atggtcgcgg gcaacacact caccatgcaa tcacaggccc cgctaaccgt gcacgactcc  28620
aaacttagca ttgccaccca aggacccctc acagtgtcag aaggaaagct agccctgcaa  28680
acatcaggcc ccctcaccac caccgatagc agtaccctta ctatcactgc ctcacccccct  28740
ctaactactg ccactggtag cttgggcatt gacttgaaag agcccattta tacacaaaat  28800
ggaaaactag gactaaagta cggggctcct ttgcatgtaa cagacgacct aaacactttg  28860
accgtagcaa ctggtccagg tgtgactatt aataatactt ccttgcaaac taaagttact  28920
```

-continued

```
ggagccttgg gttttgattc acaaggcaat atgcaactta atgtagcagg aggactaagg  28980
attgattctc aaaacagacg ccttatactt gatgttagtt atccgtttga tgctcaaaac  29040
caactaaatc taagactagg acagggccct ctttttataa actcagccca caacttggat  29100
attaactaca acaaaggcct ttacttgttt acagcttcaa acaattccaa aaagcttgag  29160
gttaacctaa gcactgccaa ggggttgatg tttgacgcta cagccatagc cattaatgca  29220
ggagatgggc ttgaatttgg ttcacctaat gcaccaaaca caaatcccct caaaacaaaa  29280
attggccatg gcctagaatt tgattcaaac aaggctatgg ttcctaaact aggaactggc  29340
cttagttttg acagcacagg tgccattaca gtaggaaaca aaaataatga taagctaact  29400
ttgtggacca caccagctcc atctcctaac tgtagactaa atgcagagaa agatgctaaa  29460
ctcactttgg tcttaacaaa atgtggcagt caaatacttg ctacagtttc agttttggct  29520
gttaaaggca gtttggctcc aatatctgga acagttcaaa gtgctcatct tattataaga  29580
tttgacgaaa atggagtgct actaaacaat tccttcctgg acccagaata ttggaacttt  29640
agaaatggag atcttactga aggcacagcc tatacaaacg ctgttggatt tatgcctaac  29700
ctatcagctt atccaaaatc tcacggtaaa actgccaaaa gtaacattgt cagtcaagtt  29760
tacttaaacg gagacaaaac taaacctgta acactaacca ttacactaaa cggtacacag  29820
gaaacaggag acacaactcc aagtgcatac tctatgtcat tttcatggga ctggtctggc  29880
cacaactaca ttaatgaaat atttgccaca tcctcttaca ctttttcata cattgcccaa  29940
gaataaagaa tcgtttgtgt tatgtttcaa cgtgtttatt tttcaattgc agaaaatttc  30000
aagtcatttt tcattcagta gtatagcccc accaccacat agcttataca gatcaccgta  30060
ccttaatcaa actcacagaa ccctagtatt caacctgcca cctccctccc aacacacaga  30120
gtacacagtc ctttctcccc ggctggcctt aaaaagcatc atatcatggg taacagacat  30180
attcttaggt gttatattcc acacggtttc ctgtcgagcc aaacgctcat cagtgatatt  30240
aataaactcc ccgggcagct cacttaagtt catgtcgctg tccagctgct gagccacagg  30300
ctgctgtcca acttgcggtt gcttaacggg cggcgaagga gaagtccacg cctacatggg  30360
ggtagagtca taatcgtgca tcaggatagg gcggtggtgc tgcagcagcg cgcgaataaa  30420
ctgctgccgc cgccgctccg tcctgcagga atacaacatg gcagtggtct cctcagcgat  30480
gattcgcacc gcccgcagca taaggcgcct tgtcctccgg gcacagcagc gcaccctgat  30540
ctcacttaaa tcagcacagt aactgcagca cagcaccaca atattgttca aaatcccaca  30600
gtgcaaggcg ctgtatccaa agctcatggc ggggaccaca gaacccacgt ggccatcata  30660
ccacaagcgc aggtagatta agtggcgacc cctcataaac acgctggaca taaacattac  30720
ctcttttggc atgttgtaat tcaccacctc ccggtaccat ataaacctct gattaaacat  30780
ggcgccatcc accaccatcc taaaccagct ggccaaaacc tgcccgccgg ctatacactg  30840
cagggaaccg ggactggaac aatgacagtg gagagcccag gactcgtaac catggatcat  30900
catgctcgtc atgatatcaa tgttggcaca acacaggcac acgtgcatac acttcctcag  30960
gattacaagc tcctcccgcg ttagaaccat atcccaggga acaacccatt cctgaatcag  31020
cgtaaatccc acactgcagg gaagacctcg cacgtaactc acgttgtgca ttgtcaaagt  31080
gttacattcg ggcagcagcg gatgatcctc cagtatggta gcgcgggttt ctgtctcaaa  31140
aggaggtaga cgatccctac tgtacggagt gcgccgagac aaccgagatc gtgttggtcg  31200
tagtgtcatg ccaaatggaa cgccggacgt agtcatattt cctgaagcaa aaccaggtgc  31260
gggcgtgaca aacagatctg cgtctccggt ctcgccgctt agatcgctct gtgtagtagt  31320
```

```
tgtagtatat ccactctctc aaagcatcca ggcgcccct ggcttcgggt tctatgtaaa 31380

ctccttcatg cgccgctgcc ctgataacat ccaccaccgc agaataagcc acacccagcc 31440

aacctacaca ttcgttctgc gagtcacaca cgggaggagc gggaagagct ggaagaacca 31500

tgttttttt tttattccaa aagattatcc aaaacctcaa aatgaagatc tattaagtga 31560

acgcgctccc ctccggtggc gtggtcaaac tctacagcca aagaacagat aatggcattt 31620

gtaagatgtt gcacaatggc ttccaaaagg caaacggccc tcacgtccaa gtggacgtaa 31680

aggctaaacc cttcagggtg aatctcctct ataaacattc cagcaccttc aaccatgccc 31740

aaataattct catctcgcca ccttctcaat atatctctaa gcaaatcccg aatattaagt 31800

ccggccattg taaaaatctg ctccagagcg ccctccacct tcagcctcaa gcagcgaatc 31860

atgattgcaa aaattcaggt tcctcacaga cctgtataag attcaaaagc ggaacattaa 31920

caaaaatacc gcgatcccgt aggtcccttc gcagggccag ctgaacataa tcgtgcaggt 31980

ctgcacggac cagcgcggcc acttccccgc caggaaccat gacaaaagaa cccacactga 32040

ttatgacacg catactcgga gctatgctaa ccagcgtagc cccgatgtaa gcttgttgca 32100

tgggcggcga tataaaatgc aaggtgctgc tcaaaaaatc aggcaaagcc tcgcgcaaaa 32160

aagaaagcac atcgtagtca tgctcatgca gataaaggca ggtaagctcc ggaaccacca 32220

cagaaaaaga caccattttt ctctcaaaca tgtctgcggg tttctgcata aacacaaaat 32280

aaaataacaa aaaaacattt aaacattaga agcctgtctt acaacaggaa aaacaaccct 32340

tataagcata agacggacta cggccatgcc ggcgtgaccg taaaaaaact ggtcaccgtg 32400

attaaaaagc accaccgaca gctcctcggt catgtccgga gtcataatgt aagactcggt 32460

aaacacatca ggttgattca catcggtcag tgctaaaaag cgaccgaaat agcccggggg 32520

aatacatacc cgcaggcgta gagacaacat tacagccccc ataggaggta taacaaaatt 32580

aataggagag aaaaacacat aaacacctga aaaaccctcc tgcctaggca aaatagcacc 32640

ctcccgctcc agaacaacat acagcgcttc cacagcggca gccataacag tcagccttac 32700

cagtaaaaaa gaaaacctat taaaaaaaca ccactcgaca cggcaccagc tcaatcagtc 32760

acagtgtaaa aaagggccaa gtgcagagcg agtatatata ggactaaaaa atgacgtaac 32820

ggttaaagtc cacaaaaaac acccagaaaa ccgcacgcga acctacgccc agaaacgaaa 32880

gccaaaaaac ccacaacttc ctcaaatcgt cacttccgtt ttcccacgtt acgtcacttc 32940

ccattttaag aaaactacaa ttcccaacac atacaagtta ctccgcccta aaacctacgt 33000

cacccgcccc gttcccacgc ccgcgccac gtcacaaact ccaccccctc attatcatat 33060

tggcttcaat ccaaaataag gtatattatt gat 33093
```

<210> SEQ ID NO 12
<211> LENGTH: 978
<212> TYPE: DNA
<213> ORGANISM: Artificial sequence
<220> FEATURE:
<223> OTHER INFORMATION: PPE-1-3X promoter

<400> SEQUENCE: 12

```
acgtgtactt ctgatcggcg atactaggga gataaggatg tacctgacaa aaccacattg 60

ttgttgttat cattattatt tagttttcct tccttgctaa ctcctgacgg aatctttctc 120

acctcaaatg cgaagtactt tagtttagaa aagacttggt ggaaggggtg gtggtggaaa 180

agtagggtga tcttccaaac taatctggtt ccccgcccgc cccagtagct gggattcaag 240
```

```
agcgaagagt ggggatcgtc cccttgtttg atcagaaaga cataaaagga aaatcaagtg    300

aacaatgatc agccccacct ccaccccacc cccctgcgcg cgcacaatac aatctattta    360

attgtacttc atacttttca ttccaatggg gtgactttgc ttctggagaa actcttgatt    420

cttgaactct ggggctggca gctagcctcc agaagcaaag tcaccccatt ggaatgaaaa    480

gtatgaagta caatgaaaag tatgaagtac tggctccaga agcaaagtca ccctccagaa    540

gcaaagtcac cccattggaa tgaaaagtat gaagtacgct agcaaaaggg gaagcgggct    600

gctgctctct gcaggttctg cagcggtctc tgtctagtgg gtgttttctt tttcttagcc    660

ctgcccctgg attgtcagac ggcgggcgtc tgcctctgaa gttagccgtg atttcctcta    720

gagccgggtc ttatctctgg ctgcacgttg cctgtgggtg actaatcaca caataacatt    780

gtttagggct ggaataaagt cagagctgtt tacccccact ctataggggt tcaatataaa    840

aaggcggcgg agaactgtcc gagtcagaag cgttcctgca ccggcgctga gagcctgacc    900

cggtctgctc cgctgtcctt gcgcgctgcc tcccggctgc ccgcgacgct ttcgccccag    960

tggaagggcc acttgctg                                                  978
```

<210> SEQ ID NO 13
<211> LENGTH: 1334
<212> TYPE: DNA
<213> ORGANISM: Mus musculus

<400> SEQUENCE: 13

```
gtgtgtgtgt gtgtgtgtgt gtgtgtgtgt gtgtgtgtgt gtgtagtgta cttctgatcg     60

gcgatactag ggagataagg atgtacctga caaaaccaca ttgttgttgt tatcattatt    120

atttagtttt ccttccttgc taactcctga cggaatcttt ctcacctcaa atgcgaagta    180

ctttagttta gaaaagactt ggtggaaggg gtggtggtgg aaaagtaggg tgatcttcca    240

aactaatctg gttccccgcc cgccccagta gctgggattc aagagcgaag agtggggatc    300

gtccccttgt ttgatcagaa agacataaaa ggaaaatcaa gtgaacaatg atcagcccca    360

cctccacccc accccccctgc gcgcgcacaa tacaatctat ttaattgtac ttcatacttt    420

tcattccaat ggggtgactt tgcttctgga gaaactcttg attcttgaac tctggggctg    480

gcagctagca aaggggaag cgggctgctg ctctctgcag gttctgcagc ggtctctgtc    540

tagtgggtgt tttctttttc ttagccctgc ccctggattg tcagacggcg ggcgtctgcc    600

tctgaagtta gccgtgattt cctctagagc cgggtcttat ctctggctgc acgttgcctg    660

tgggtgacta atcacacaat aacattgttt agggctggaa taaagtcaga gctgtttacc    720

cccactctat aggggttcaa tataaaaagg cggcggagaa ctgtccgagt cagacgcgtt    780

cctgcaccgg cgctgagagc ctgacccggt ctgctccgct gtccttgcgc gctgcctccc    840

ggctgcccgc gacgctttcg ccccagtgga agggccactt gctgaggacc gcgctgagat    900

ctaaaaaaaa aacaaaaaac aaaaaacaaa aaaacccaga ggcgatcaga gcgaccagac    960

accgtcctct tcgttttgca ttgagttcca tttgcaaccg agttttcttt ttttcctttt   1020

tccccactct tctgacccct ttgcagaatg gattattttc ccgtgatctt ctctctgctg   1080

ttcgtgactt tccaaggagc tccagaaaca ggtaggcgcc acttgcgaat ctttctactt   1140

cagcgcagca gttatcgctt ctgttttcca cttttctttc tttcttttct ttcattcttt   1200

ccttttttatt tatttttttta attactgaag ctccagcagc aagtgcctta caattaatta   1260

acttctgtgt gaagcgaaag aaataaaacc cctgtttgaa tacagctgac tacaaccgag   1320

tatcgcatag cttc                                                     1334
```

COMPOSITIONS AND METHODS FOR TREATING GLIOBLASTOMA GBM

REFERENCE TO SEQUENCE LISTING SUBMITTED ELECTRONICALLY VIA EFS-WEB

This application includes a SequenceListing.ascii.txt, 190,795 bytes, created on Jun. 20, 2013, and submitted electronically via EFS-Web, which is hereby incorporated by reference in its entirety.

FIELD AND BACKGROUND OF THE INVENTION

The present invention, in some embodiments thereof, relates to compositions and methods for treating malignant gliomas and, more particularly, but not exclusively, for treating Glioblastoma multiforme (GBM).

Malignant gliomas, the most common adult-onset neurological neoplasms, encompass a family of primary central nervous system tumors including glioblastoma, astrocytoma, oligodendroglioma, and ependymoma, along with the juvenile onset neoplasms such as juvenile pilocystic astrocytoma.

Malignant gliomas are typically characterized by overexpression of growth factors/tumor associated antigens believed to significantly contribute to the unchecked growth of such tumors. Various malignant gliomas, such as glioblastomas, exhibit epidermal growth factor receptor (EGFR) overexpression leading to increased aggressiveness and poor prognosis. Malignant gliomas may also display over-expression of platelet-derived growth factor receptor, a phenomenon which has also been correlated with increased malignancy and poor prognosis.

Malignant gliomas, the most common type of primary brain tumors, are aggressive, highly invasive, and neurologically destructive tumors which are among the deadliest of all human cancers. Of the estimated 17,000 new brain tumors diagnosed each year in the United States, about half are malignant gliomas. Malignant glioma cells produce very invasive brain tumors with infiltration of both white and gray matter. At the time of diagnosis, microscopic extension through much of the neural axis by malignant glioma is the rule. Such extension by motile invading cells underlies the incurability by surgery of most gliomas, even when they appear small and restricted in nature.

Glioblastoma multiforme (GBM), the most serious form of malignant glioma, are extremely aggressive brain tumors which generally arise in the upper brain (cerebrum), but which may also occur elsewhere in the central nervous system, such as in the spinal cord, cerebellum, brain stem, or optic chiasm. Low-grade gliomas, which include astrocytomas, oligodendrogliomas, and pilocytic astrocytomas, account for 25% of all primary brain tumors, and over time most of these low-grade tumors dedifferentiate into more malignant gliomas. Diffuse astrocytomas are predominantly located in the cerebral hemispheres of adults and have an inherent tendency to progress to anaplastic astrocytoma and (secondary) glioblastoma. The majority of glioblastomas develop de novo (primary glioblastomas), without an identifiable less-malignant precursor lesion.

Despite optimal therapy with surgery, radiotherapy, and temozolomide chemotherapy, the median survival of patients with glioblastomas is only 12-15 months. When these tumors recur, conventional salvage therapies produce minimal benefit, with only 8-15% of patients alive and free from progression at 6 months (6M-PFS).

Neovascularization is a major feature of glioblastomas (Maher et al., 2001, Genes Dev. 15:1311-1333). Angiogenesis activators are extremely important in tumor growth, as reflected by the fact that neovascularization must occur for solid tumors to grow beyond a diameter of 2-3 mm (Goldbrunner et al., 2000, J. Neurooncol. 50:53-62). One of the molecules that regulates this process is the vascular endothelial growth factor (VEGF). VEGF mRNA is overexpressed in the highly vascularized glioblastoma multiform (Maher et al., 2001, Genes Dev. 15:1311-1333). It has been demonstrated that the transfection of antisense-VEGF-complementary-DNA as well VEGF antisense RNA encoding vectors result in down-regulation of the endogenous VEGF and inhibits growth of gliomas in mice (Sasaki et al., 1999, Int. J. Dev. Neurosci. 17:579-591; Zheng et al., 2000, Acta Pharmacol. Sin. 21:211-214). A similar effect was observed upon the local delivery of the angiogenesis inhibitor endostatin (Read et al., 2001, Nat. Biotechnol. 19:29-34). However, this strategy has a cytostatic effect. It is effective in inhibiting tumor growth but not in actually eliminating them.

Bevacizumab (Avastin®) is a humanized monoclonal antibody that binds VEGF, preventing it from activating its receptors, especially VEGFR2, abrogating subsequent biologic effects. This drug has shown benefit in colorectal, non-small cell lung, and breast cancers, and is approved by the Food and Drug Administration for these indications. Several studies have now evaluated the combination of bevacizumab and the chemotherapeutic agent irinotecan in recurrent malignant gliomas and the results have been more encouraging.

In one phase II study, the combination of bevacizumab and irinotecan produced a response rate of 67% and 6M-PFS of 56% in recurrent anaplastic gliomas, and a response rate of 57% and a 6M-PFS of 46% in recurrent glioblastomas.

These preliminary findings have been recently confirmed by a large multi-center randomized phase II study of 167 patients with recurrent GBM who were treated with bevacizumab alone or in combination with irinotecan [Cloughesy T, Prados M, Wen P, et al. Society for Neuro-Oncology 12th Annual Meeting, 2007].

Patients receiving bevacizumab alone had a response rate of 20% and a 6M-PFS of 35.1%, while patients receiving the combination of bevacizumab in combination with irinotecan had a response rate of 34% and 6M-PFS of 51%. The median survival was 9.7 months for bevacizumab (Avastin) alone, and 8.7 months for the combination. In addition, treatment with bevacizumab was also associated with a significant reduction in peritumoral edema and the need for corticosteroids. As a result of these studies, the combination of bevacizumab with irinotecan is increasingly used for the treatment of patients with recurrent malignant gliomas.

Another agent proposed for the treatment of malignant gliomas is Aflibercept (VEGF-Trap). This is a soluble hybrid receptor, composed of portions of VEGFR-1 and VEGFR-2 fused to an immunoglobulin G1 Fc domain. Like bevacizumab, it is designed to deplete circulating VEGF, but has significantly greater affinity for VEGF than bevacizumab itself.

In addition, inhibitors of VEGF receptors have been proposed for the treatment of malignant gliomas. In a phase II trial study of a potent pan-VEGFR inhibitor, cediranib (AZD2171; Recentin) in patients with recurrent glioblastomas, response rates in excess of 50% were observed and the 6M-PFS was increased to approximately 25%. Studies with other inhibitors of VEGFR such as sorafenib (Nexavar), sunitinib (Sutent), vandetanib (ZD6474; Zactima), pazopanib (GW786034), and vatalanib (PTK787) in glioblastomas are also in progress.

In comparison with drugs targeting VEGF or VEGFR, agents inhibiting other angiogenic pathways have produced less success. Drugs that inhibit PDGF receptors such as imatinib mesylate (Gleevec) were ineffective, due partly to its poor penetration across the blood-brain barrier. Cilengitide, a drug that inhibits αvβ3 and αvβ5 integrins has shown modest activity in glioblastomas and studies combining it with other agents are in progress.

The use of viral vectors as gene delivery agents has been proposed for the treatment of malignant gliomas. Such viruses may be engineered to produce anticancer activity by expressing transgenes whose products exert a tumoricidal effect.

Several of such approaches have shown anti-tumor efficiency in experimental studies, and the first clinical trials for the treatment of malignant glioma were conducted in the 1990s. HSV-tk gene therapy has been the pioneering and most commonly used approach, but oncolytic conditionally replicating adenoviruses and herpes simplex virus mutant vectors, p53, interleukins, interferons, and antisense oligonucleotides have also been used.

U.S. Pat. No. 5,747,340 teaches use of a murine endothelial cell-specific promoter which shows selectivity towards angiogenic cells.

International Application WO/2008/132729 teaches viral vectors comprising endothelial cell specific promoters which directs expression of a transgene in angiogenic cells for the treatment of cancer.

SUMMARY OF THE INVENTION

According to an aspect of some embodiments of the present invention there is provided a use of a viral vector for preparation of a medicament for the treatment of a malignant glioma, the nucleic acid construct comprising:

(i) a first polynucleotide sequence encoding a Fas-chimera (Fas-c), the first polynucleotide sequence comprising SEQ ID NOs: 2 and 3; and (ii) a second polynucleotide sequence encoding an endothelial cell-specific promoter or a periendothelial cell-specific promoter.

According to an aspect of some embodiments of the present invention there is provided a use of a viral vector for the treatment of a malignant glioma, the nucleic acid construct comprising:

(i) a first polynucleotide sequence encoding a Fas-chimera (Fas-c), the first polynucleotide sequence comprising SEQ ID NOs: 2 and 3; and (ii) a second polynucleotide sequence encoding an endothelial cell-specific promoter or a periendothelial cell-specific promoter.

According to an aspect of some embodiments of the present invention there is provided a method of treating a malignant glioma in a subject in need thereof, the method comprising administering to the subject a therapeutically effective amount of a viral vector comprising:

(i) a first polynucleotide sequence encoding a Fas-chimera (Fas-c), the first polynucleotide sequence comprising SEQ ID NOs: 2 and 3; and (ii) a second polynucleotide sequence encoding an endothelial cell-specific promoter or a periendothelial cell-specific promoter, thereby treating the malignant glioma.

According to some embodiments of the present invention the promoter is set forth in SEQ ID NO: 12.

According to some embodiments of the present invention the promoter is set forth in SEQ ID NO: 13.

According to some embodiments of the present invention the viral vector is an adenoviral vector.

According to some embodiments of the present invention the adenoviral vector is a non-replicating adenoviral vector.

According to some embodiments of the present invention the promoter comprises at least one copy of a sequence set forth in SEQ ID NO: 6.

According to some embodiments of the present invention the promoter comprises at least two copies of a sequence set forth in SEQ ID NO: 6.

According to some embodiments of the present invention the promoter comprises a sequence as set forth in SEQ ID NO: 7.

According to some embodiments of the present invention the promoter comprises a sequence as set forth in SEQ ID NO: 8.

According to some embodiments of the present invention the promoter comprises a hypoxia response element (HRE) as set forth in SEQ ID NO: 5.

According to some embodiments of the present invention the viral vector consists of a sequence as set forth in SEQ ID NO: 9 or SEQ ID NO: 10. According to some embodiments of the present invention the malignant glioma is selected from the group consisting of glioblastoma, astrocytoma, oligodendroglioma, and ependymoma, and juvenile pilocystic astrocytoma.

According to some embodiments of the present invention the therapeutically effective amount of the nucleic acid construct is about $10^3$ to about $10^{16}$ virus particles.

According to some embodiments of the present invention the therapeutically effective amount of the nucleic acid construct is about $10^5$ to about $10^{13}$ virus particles.

According to some embodiments of the present invention the therapeutically effective amount of the nucleic acid construct is about $10^7$ to about $10^{12}$ virus particles.

According to some embodiments of the present invention the therapeutically effective amount of the nucleic acid construct is about $1\times10^{12}$ to about $5\times10^{12}$ virus particles.

According to some embodiments of the present invention the therapeutically effective amount of the nucleic acid construct is about $1\times10^{13}$ to about $5\times10^{13}$ virus particles.

According to some embodiments of the present invention the administering comprises intravenous administration.

According to some embodiments of the present invention the administering comprises local administration.

According to some embodiments of the present invention the administering is in at least two, or at least three or more doses of said viral vector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to compositions and methods for treating malignant gliomas and, more particularly, but not exclusively, for treating Glioblastoma multiforme (GBM).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Malignant gliomas, the most common subtype of primary brain tumors, are aggressive, highly invasive, and neurologically destructive tumors. These tumors are considered to be among the deadliest of all human cancers. In its most aggressive form, glioblastoma (GBM), median survival ranges from 9 to 12 months. Despite several decades of technological advances in neurosurgery and radiation therapy there has been no significant change in the overall statistics.

Gene therapy approaches for the treatment of malignant gliomas have been attempted. However, while these approaches have proved successful in vitro and in animal models, these strategies have met with limited success in clinical trials. It is believed that the low in vivo infection efficiency of the vectors is connected to the histological structure of the glioblastomas. These are very solid tumors, which are almost completely impermeable to diffusion of big particles such as viruses.

The present inventors surprisingly found that treatment of glioblastomas in animals could be carried out effectively using viral vectors encoding a toxic molecule (Fas-chimera (Fas-c)) under the control of a promoter which directs transcription in endothelial cells.

Figure 2:
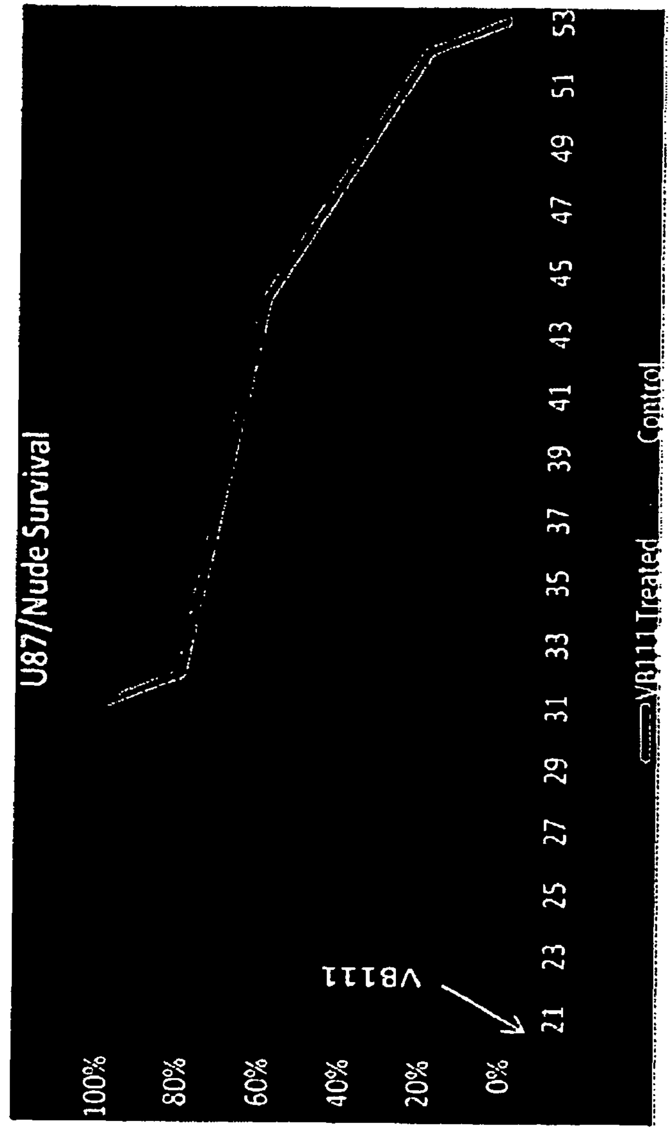
FIG. 2 is a graph illustrating the effect of VB-111 on survival of rats pre-inoculated with U87 tumor cells.
Figure 3:
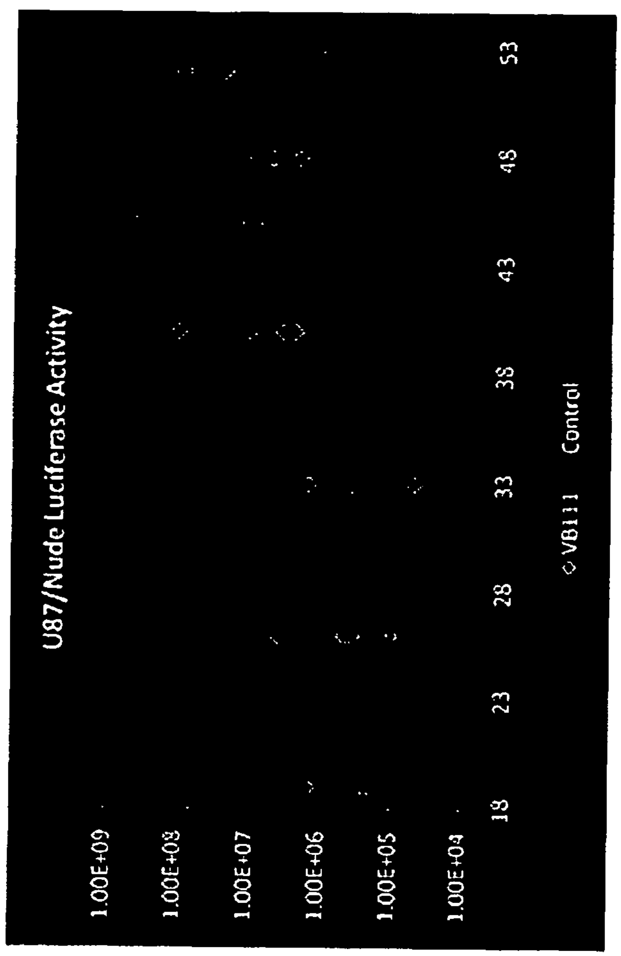
FIG. 3 is a graph illustrating the effect of VB-111 on tumor size (as measured by luciferase activity) of rats pre-inoculated with U87 tumor cells.
Figure 4:
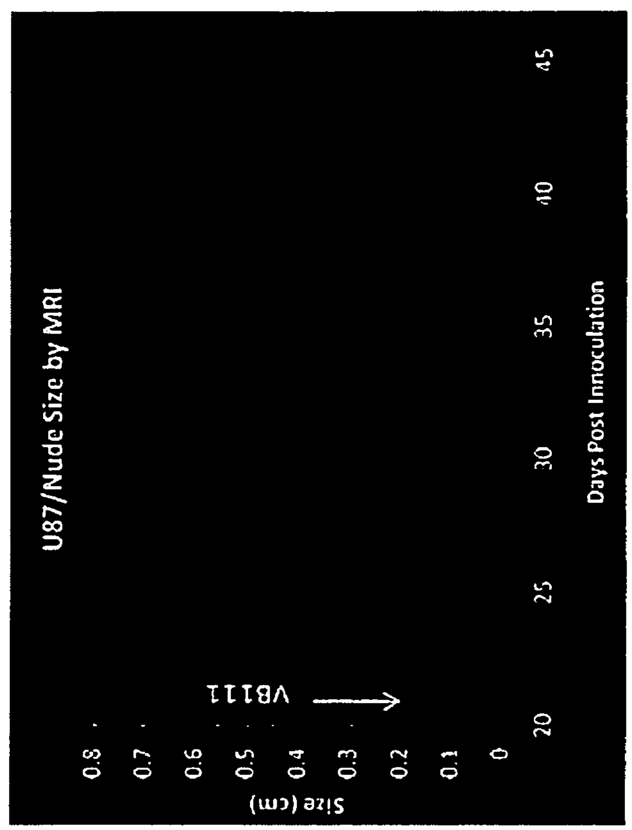
FIG. 4 is a graph illustrating the effect of VB-111 on tumor size (as measured by MRI) of rats pre-inoculated with U87 tumor cells.
Figures 5A, 5B, 5C:
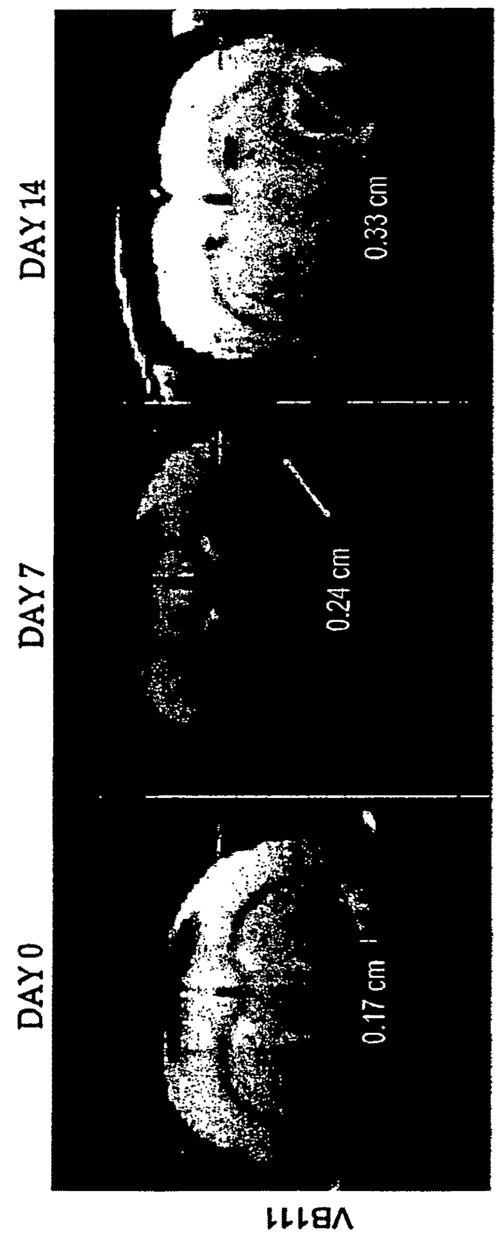
FIGS. 5A-F are photographs of brain slices illustrating the effect of VB-111 on tumor size (as measured by MRI) of rats pre-inoculated with U87 tumor cells.
Figures 5D, 5E, 5F:
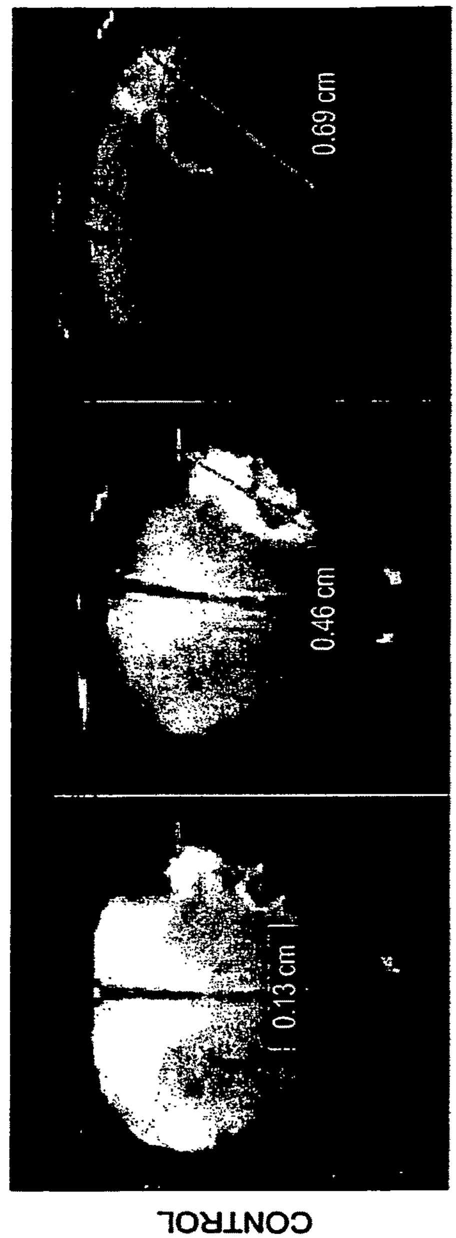

Using an animal model of glioblastoma whereby rats were pre-inoculated with U87 tumor cells, the present inventors showed that administration of such viral vectors decreased the size of the luciferase-tagged tumors as measured by luciferase activity (FIG. 3) and MRI (FIGS. 4 and 5). The present inventors further showed that administration of such viral vectors increased survival of the rats (FIG. 2).

Thus, according to one aspect of the present invention, there is provided a method of treating a malignant glioma in a subject in need thereof, the method comprising administering to the subject a therapeutically effective amount of a viral vector comprising:

(i) a first polynucleotide sequence encoding a Fas-chimera (Fas-c); and (ii) a second polynucleotide sequence encoding an endothelial cell-specific promoter or a periendothelial cell-specific promoter, thereby treating the malignant glioma.

As used herein, the phrase "malignant glioma" refers to a primary central nervous system tumor typically characterized by over-expression of growth factor receptors and/or tumor associated antigens. According to one embodiment the malignant glioma exhibits epidermal growth factor receptor (EGFR) overexpression. According to one embodiment the malignant glioma exhibits platelet-derived growth factor receptor (PDFR) overexpression. According to another embodiment the malignant glioma exhibits both platelet-derived growth factor receptor (PDFR) overexpression and epidermal growth factor receptor (EGFR) overexpression.

Examples of malignant gliomas include, but are not limited to glioblastoma, astrocytoma, oligodendroglioma, ependymoma, and juvenile onset neoplasms such as juvenile pilocystic astrocytoma.

Contemplated subjects to be treated include mammals—e.g. humans. According to one embodiment the subject has received a prior treatment for the malignant glioma (e.g. radiotherapy and/or chemotherapy) and the malignant glioma has relapsed. According to another embodiment, the subject has not received a prior treatment for the malignant glioma.

The phrase "viral vector" refers to a replication competent or replication-deficient viral particle which are capable of transferring nucleic acid molecules into a host.

The present inventors contemplate use of Replication Defective Vectors and Replication Defective Vector-Producing Packaging Cells. Examples of such vectors are adenoviral vectors, AAV vectors and retroviral vectors and others described in Shir et al, Cellular and Molecular Neurobiology, Vol. 21, No. 6, December 2001, the contents of which are incorporated herein by reference.

The term "virus" refers to any of the obligate intracellular parasites having no protein-synthesizing or energy-generating mechanism. The viral genome may be RNA or DNA contained with a coated structure of protein of a lipid membrane. Examples of viruses useful in the practice of the present invention include baculoviridiae, parvoviridiae, picornoviridiae, herepesviridiae, poxyiridiae, adenoviridiae, picotrnaviridiae. The term recombinant virus includes chimeric (or even multimeric) viruses, i.e. vectors constructed using complementary coding sequences from more than one viral subtype. (See, e.g. Feng, et al. Nature Biotechnology 15:866-870) The term "adenovirus" is synonymous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F subgenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1, 2, 3, 4, 7, and 10. The term canine adenoviruses includes but is not limited to canine types 1 (strains CLL, Glaxo, RI261, Utrect, Toronto 26-61) and 2. The term equine adenoviruses includes but is not limited to equine types 1 and 2. The term porcine adenoviruses includes but is not limited to porcine types 3 and 4. In one embodiment of the invention, the adenovirus is derived from the human adenovirus serotypes 2 or 5. For purposes of this invention, adenovirus vectors can be replication-competent or replication deficient in a target cell. In some embodiments, the adenovirus vectors are conditionally or selectively replicating adenoviruses, wherein a gene[s] required for viral replication is [are] operatively linked to a cell and/or context-specific promoter. Examples of selectively replicating or conditionally replicating viral vectors are known in the art (see, for example, U.S. Pat. No. 7,691,370). In one embodiment, the adenovirus vector is a conditionally replicating adenovirus wherein the E1 gene is under transcriptional control of the pre-proendothelin promoter PPE-1 (PPE-1, SEQ ID NO: 13). In another embodiment, the adenovirus vector is a conditionally replicating or selectively replicating adenovirus wherein the E1 gene is under transcriptional control of the modified pre-proendothelin promoter PPE-1-3X (PPE-1-3X, SEQ ID NO: 12). In some embodiments, adenovirus vectors suitable for use with the present invention include all adenovirus serotypes having hexon protein structure. Viral vectors suitable for therapeutic use include adenoviral vectors, retrovirusal vectors, AAV, herpesvirus vectors and the like. Engineering and production of viral vectors is well known in the art, as described in detail in, for example, U.S. Pat. No. 7,732,129 or 6,649,158, which are incorporated herein by reference, in their entirety. In specific embodiments, the adenovirus is a C-type adenovirus (Ad5, Ad2), a B-type adenovirus (Ad3, Ad16, Ad21, Ad35, Ad50), an E-type adenovirus (Ad4) or an F-type adenovirus (Ad41).

As used herein, the phrase adenoviral vector refers to a vector in which, among the nucleic acid molecules in the viral particle, sequences necessary to function as a viral vector are based on the adenoviral genome.

According to one embodiment the adenoviral vector is a non-replicating serotype 5 (Ad5) adenoviral vector.

According to another embodiment, the adenoviral vector comprises a sequence as set forth in SEQ ID NO: 1 or SEQ ID NO: 11.

It will be appreciated that the present invention also contemplates use of oncolytic viruses which reproduce themselves in cancer cells and subsequently kill the initially infected cells by lysis. Such viruses proceed to infect adjacent cells thus repeating the cycle. Contemplated example of oncolytic viruses include, but are not limited to Herpes Simplex Virus, conditionally replicative Ads (CRAds) and reoviruses.

Two major strategies for development of CRAd vectors have been developed, mainly focusing on the genetic engineering of the early 1 (E1) genes to restrict virus replication to target cells and to spare normal tissue. Genetic complementation-type (type 1) CRAds, such as Ad524, have a mutation in the immediately early (E1A) or early (E1B) adenoviral region, which is complemented in tumor cells but not in normal cells. In trans complementation-type (type 2) CRAds, virus replication is controlled via a tumor/tissue-specific promoter.

Reovirus is a naturally occurring oncolytic virus that requires activated Ras signaling pathways of tumor cells for its replication. Ras pathways are activated in most malignant gliomas via upstream signaling by receptor tyrosine kinases.

As mentioned the viral vectors of this aspect of the present invention comprise:

(i) a first polynucleotide sequence encoding a Fas-chimera (Fas-c); and (ii) a second polynucleotide sequence encoding an endothelial cell-specific promoter or a periendothelial cell-specific promoter, thereby treating the malignant glioma.

Typically, such viral vectors are constructed using genetic recombination technology—i.e. recombinant viral vectors.

The Fas-chimera (Fas-c), is a previously described fusion of two “death receptors”, constructed from the extracellular region of TNFR1 (SEQ ID NO: 2) and the trans-membrane and intracellular regions of Fas (SEQ ID NO: 3) [Boldin M P et al. J Biol Chem (1995) 270(14):7795-8].

According to one embodiment the Fas-c is encoded by a polynucleotide as set forth in SEQ ID NO: 4.

It will be appreciated that the present invention also contemplates use of a viral construct (e.g. an adenoviral construct) comprising an endothelial/periendothelial cell-specific promoter operatively linked to other cytotoxic polypeptides for the treatment of malignant glioma.

Such polypeptides, include but are not limited to suicide polypeptides such as p53 and egr-1-TNF-alpha, cytotoxic pro-drug/enzymes for drug susceptibility therapy such as ganciclovir/thymidine kinase and 5-fluorocytosine/cytosine deaminase, and antimetastatic polypeptides such as 5 E1A.

The term “promoter” as used herein refers to a DNA sequence which directs transcription of a polynucleotide sequence operatively linked thereto in the cell in a constitutive or inducible manner. The promoter may also comprise enhancer elements which stimulate transcription from the linked promoter.

As used herein, the phrase endothelial cell-specific promoter refers to a promoter which directs expression of a gene operatively linked thereto in endothelial cells, wherein the level of expression in endothelial cells is at least 2 times higher than in non-endothelial cells. According to a particular embodiment, the level of expression in endothelial cells is at least 5 times higher than in non-endothelial cells.

As used herein, the phrase periendothelial cell-specific promoter refers to a promoter which directs expression of a gene operatively linked thereto in periendothelial cells (i.e., pericytes in small vessels or smooth muscle cells in larger vessels), wherein the level of expression in endothelial cells is at least 2 times higher than in non-periendothelial cells. According to a particular embodiment, the level of expression in periendothelial cells is at least 5 times higher than in non-periendothelial cells.

Exemplary endothelial cell-specific promoters or periendothelial cell-specific promoters include, but are not limited to the preproendothelin-1 (PPE-1) promoter, and modifications thereof such as described herein below, the TIE-1 promoter, the TIE-2 promoter, the Endoglin promoter, the von Willerband promoter, the KDR/flk-1 promoter, The FLT-1 promoter, the Egr-1 promoter, the ICAM-1 promoter, the VCAM-1 promoter, the PECAM-1 promoter and the aortic carboxypeptidase-like protein (ACLP) promoter.

The preproendothelial promoter refers to the preproendothelin-1 promoter, of mammalian origin. In one embodiment, the preproendothelin 1 promoter is a murine preproendothelin 1 promoter as set forth in SEQ ID NO: 13.

According to one embodiment the promoter comprises at least one copy of an enhancer element that confers endothelial cell specific transcriptional activity.

According to one embodiment the enhancer element is naturally found positioned between the −364 bp and −320 bp of the murine PPE-1 promoter (as set forth in SEQ ID NO: 6). Preferably, the promoter comprises at least two and more preferably three of the above described enhancer elements. According to a specific embodiment, the promoter comprises two of the above described enhancer elements on one strand of the promoter DNA and one of the above described enhancer element on the complementary strand of the promoter DNA (as set forth in SEQ ID NO:7).

According to another embodiment, the promoter further comprises at least one hypoxia response element—e.g. comprising a sequence as set forth in SEQ ID NO: 5.

An exemplary promoter which can be used in the context of the present invention comprises a sequence as set forth in SEQ ID NO: 12. This promoter is also referred to herein as the PPE-1-3X promoter. This sequence comprises SEQ ID NO: 5 and SEQ ID NO: 7 (which itself comprises two copies of SEQ ID NO: 6 either side of one copy of SEQ ID NO: 8).

According to a particular embodiment of this aspect of the present invention, the viral vector consists of a sequence as set forth in SEQ ID NOs: 9 or 10. This viral vector is also referred to herein as VB111 and AD5PPE-1-3X-fas-chimera.

This sequence comprises SEQ ID NO: 12 in the antisense orientation at position 460-1437.

This sequence also comprises SEQ ID NO: 7 in the antisense orientation at position 894-1036; a single copy of SEQ ID NO: 8 in the antisense orientation at position 951-997; a first copy of SEQ ID NO: 6 in the antisense orientation at position 907-950; a second copy of SEQ ID NO: 6 in the antisense orientation at position 993-1036; and a third copy of SEQ ID NO: 6 at position 823-866 in the sense orientation.

In some embodiments of the invention, the viral vector comprises additional polynucleotide sequences capable of enhancing or inhibiting transcriptional activity of an endothelial specific promoter. According to an aspect of some embodiments of the invention, the additional polynucleotide sequence includes an isolated polynucleotide comprising at least 6 nucleotides of element X of a preproendothelin (PPE-1) promoter, the element X having a wild type sequence as set forth by SEQ ID NO:6, wherein the at least 6 nucleotides comprise at least 2 consecutive sequences derived from SEQ ID NO:6, each of the at least 2 consecutive sequences comprises at least 3 nucleotides, at least one of the at least 3 nucleotide being positioned next to at least one nucleotide position in SEQ ID NO:6, the at least one nucleotide position in SEQ ID NO:6 is selected from the group consisting of:

(i) at least one nucleotide of wild type M4 sequence set forth by SEQ ID NO: 15 (CATTC);

(ii) at least one nucleotide of wild type M5 sequence set forth by SEQ ID NO: 16 (CAATG);

(iii) at least one nucleotide of wild type M8 sequence set forth by SEQ ID NO: 19 (GCTTC);

(iv) at least one nucleotide of wild type M6 sequence set forth by SEQ ID NO: 17 (GGGTG);

(v) at least one nucleotide of wild type M7 sequence set forth by SEQ ID NO: 18 (ACTTT);

(vi) at least one nucleotide of wild type M1 sequence set forth by SEQ ID NO: 20 (GTACT); and (v) at least one nucleotide of wild type M3 sequence set forth by SEQ ID NO: 21 (CTTTT);

wherein the at least one nucleotide position is mutated as compared to SEQ ID NO:6 by at least one nucleotide substitution, at least one nucleotide deletion and/or at least one nucleotide insertion, with the proviso that a mutation of the at least one nucleotide position does not result in nucleotides GGTA at position 21-24 of SEQ ID NO:6 and/or in nucleotides CATG at position 29-32 of SEQ ID NO:6, such that when the isolated polynucleotide is integrated into the PPE-1 promoter and placed upstream of a reporter gene (e.g., luciferase coding sequence) the expression level of the reporter gene is upregulated or downregulated as compared to when SEQ ID NO:6 is similarly integrated into the PPE-1 promoter and placed upstream of the reporter gene coding sequence.

According to some embodiments of the invention, the isolated polynucleotide is not naturally occurring in a genome or a whole chromosome sequence of an organism.

As used herein the phrase “naturally occurring” refers to as found in nature, without any man-made modifications.

As described above, the at least 6 nucleotides of element X comprise at least 2 consecutive sequences derived from SEQ ID NO:6.

As used herein the phrase “consecutive sequence derived from SEQ ID NO:6” refers to a nucleic acid sequence (a polynucleotide) in which the nucleotides appear in the same order as in the nucleic acid sequence of SEQ ID NO:6 from which they are derived. It should be noted that the order of nucleotides is determined by the chemical bond (phosphodiester bond) formed between a 3'-OH of a preceding nucleotide and the 5'-phosphate of the following nucleotide.

According to some embodiments of the invention, each of the at least 2 consecutive sequences comprises at least 3 nucleotides, e.g., 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotide, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides of SEQ ID NO:6.

As described, the isolated polynucleotide comprises at least 2 consecutive sequences derived from SEQ ID NO:6. According to some embodiments of the invention, the isolated polynucleotide comprises 2, 3, 4, 5, 6, 7, 8, 9, 10, 11, 12, 13 or 14 consecutive sequences derived from SEQ ID NO:6.

As used herein the phrase “wild type” with respect to a nucleotide sequence refers to the nucleic acid sequence as appears in SEQ ID NO:6. Examples include, but are not limited to wild type M4 sequence (SEQ ID NO: 15), wild type M5 sequence (SEQ ID NO: 16), wild type M8 (SEQ ID NO:19), wild type M6 sequence (SEQ ID NO:17), wild type M7 sequence (SEQ ID NO:18), wild type M1 (SEQ ID NO:20) and wild type M3 sequence (SEQ ID NO:21).

According to some embodiments of the invention, the mutation is an insertion of at least one nucleotide in a nucleotide position with respect to SEQ ID NO:6. According to some embodiments of the invention, the insertion includes at least 1, 2, 3, 4, 5, 6, 7, 8, 9, 10 nucleotides, e.g., at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, or more nucleotides.

It should be noted that the sequence which is inserted by the mutation can be derived from any source (e.g., species, tissue or cell type), and is not limited to the source of the sequence of element X.

According to some embodiments of the invention, the mutation is a combination of any of the mutation types described above, i.e., substitution, insertion and deletion. For example, while one nucleotide position in SEQ ID NO:6 can be subject to a substitution mutation, another nucleotide position in SEQ ID NO:6 can be subject to a deletion or insertion. Additionally or alternatively, while one nucleotide position in SEQ ID NO:6 can be subject to a deletion mutation, another nucleotide position in SEQ ID NO:6 can be subject to a substitution or insertion. Additionally or alternatively, while one nucleotide position in SEQ ID NO:6 can be subject to an insertion mutation, another nucleotide position in SEQ ID NO:6 can be subject to a substitution or deletion. It should be noted that various other combinations are possible.

According to specific embodiments of the invention, the mutation in the isolated polynucleotide of the invention does not result in nucleotides GGTA at position 21-24 of SEQ ID NO:6 and/or in nucleotides CATG at position 29-32 of SEQ ID NO:6.

As used herein the phrase "integrated into the PPE-1 promoter" refers to a nucleotide sequence (the isolated polynucleotide) which is covalently conjugated within the PPE-1 promoter sequence.

According to some embodiments of the invention, the isolated polynucleotide further comprises at least one copy of a nucleic acid sequence selected from the group consisting of:

(i) wild type M4 sequence set forth by SEQ ID NO: 15 (CATTC), (ii) wild type M5 sequence set forth by SEQ ID NO: 16 (CAATG), (iii) wild type M8 sequence set forth by SEQ ID NO: 19 (GCTTC), (iv) wild type M6 sequence set forth by SEQ ID NO: 17 (GGGTG), (v) wild type M7 sequence set forth by SEQ ID NO: 18 (ACTTT);

(vi) wild type M1 sequence set forth by SEQ ID NO: 20 (GTACT), and (vii) wild type M3 sequence set forth by SEQ ID NO: 21 (CTTTT).

According to some embodiments of the invention, the isolated polynucleotide is integrated into (within), downstream of, or upstream of any known (or unknown) promoter sequence to thereby regulate (e.g., increase, decrease, modulate tissue-specificity, modulate inductive or constitutive expression) the transcriptional promoting activity of the promoter.

According to some embodiments of the invention, the isolated polynucleotide is for increasing expression of a heterologous polynucleotide operably linked thereto in endothelial cells. Such a polynucleotide can include wild type sequences of M4 and/or M5 in the presence or absence of additional sequences from element X, and/or in the presence of other mutated sequences from element X.

According to some embodiments of the invention, the isolated polynucleotide comprises at least one copy of the wild type M4 sequence set forth by SEQ ID NO: 15 (CATTC).

According to some embodiments of the invention, the isolated polynucleotide comprises at least one copy of the wild type M5 sequence set forth by SEQ ID NO: 16 (CAATG).

According to some embodiments of the invention, the isolated polynucleotide comprises at least one copy of the wild type M4 sequence set forth by SEQ ID NO: 15 (CATTC) and at least one copy of the wild type M5 sequence set forth by SEQ ID NO: 16 (CAATG).

According to some embodiments of the invention, the at least one nucleotide position which is mutated as compared to SEQ ID NO:6 is at least one nucleotide of the wild type M8 sequence set forth by SEQ ID NO: 19 (GCTTC). It should be noted that such an isolated polynucleotide may further include a wild type M6 sequence (SEQ ID NO:17) and/or a wild type M7 sequence (SEQ ID NO:18) Non-limiting examples of isolated polynucleotides which include at least one copy of the wild type M4 sequence set forth by SEQ ID NO: 15 (CATTC) and a mutation in at least one nucleotide of the wild type M8 sequence set forth by SEQ ID NO: 19 (GCTTC) are provided in SEQ ID NOs:55-62.

Non-limiting examples of isolated polynucleotides which include at least one copy of the wild type M5 sequence set forth by SEQ ID NO: 16 (CAATG) and a mutation in at least one nucleotide of the wild type M8 sequence set forth by SEQ ID NO: 19 (GCTTC) are provided in SEQ ID NOs: 63-66.

Non-limiting examples of isolated polynucleotides which include at least one copy of the wild type M4 sequence set forth by SEQ ID NO: 15 (CATTC), at least one copy of the wild type M5 sequence set forth by SEQ ID NO: 16 (CAATG) and a mutation in at least one nucleotide of the wild type M8 sequence set forth by SEQ ID NO: 19 (GCTTC) are provided in SEQ ID NOs: 67-70.

According to some embodiments of the invention, the isolated polynucleotide further comprising at least one copy of wild type M1 sequence set forth by SEQ ID NO: (GTACT).

Non-limiting examples of isolated polynucleotides which include at least one copy of the wild type M4 sequence set forth by SEQ ID NO: 15 (CATTC), at least one copy of the wild type M1 sequence set forth by SEQ ID NO: 20 (GTACT), and a mutation in at least one nucleotide of the wild type M8 sequence set forth by SEQ ID NO: 19 (GCTTC) are provided in SEQ ID NOs: 71-105.

Non-limiting examples of isolated polynucleotides which include at least one copy of the wild type M5 sequence set forth by SEQ ID NO: 16 (CAATG), at least one copy of the wild type M1 sequence set forth by SEQ ID NO: 20 (GTACT) and a mutation in at least one nucleotide of the wild type M8 sequence set forth by SEQ ID NO: 19 (GCTTC) are provided in SEQ ID NOs: 106-136.

Non-limiting examples of isolated polynucleotides which include at least one copy of the wild type M4 sequence set forth by SEQ ID NO: 15 (CATTC), at least one copy of the wild type M5 sequence set forth by SEQ ID NO: 16 (CAATG), at least one copy of the wild type M1 sequence set forth by SEQ ID NO: 20 (GTACT) and a mutation in at least one nucleotide of the wild type M8 sequence set forth by SEQ ID NO: 19 (GCTTC) are provided in SEQ ID NOs:137-152.

According to some embodiments of the invention, the isolated polynucleotide reduces expression of a heterologous polynucleotide operably linked thereto in endothelial cells. Such a polynucleotide can include mutations in M4 and/or M5 in the presence or absence of additional sequences from element X, and/or in the presence of other mutated sequences from element X.

According to some embodiments of the invention, the at least one nucleotide position which is mutated as compared to SEQ ID NO:6 is at least one nucleotide of the wild type M4 sequence set forth by SEQ ID NO: 15 (CATTC).

Non-limiting examples of isolated polynucleotides which includes a mutation in at least one nucleotide of the wild type M4 sequence set forth by SEQ ID NO:46 (CATTC) are provided in SEQ ID NOs:153-162.

According to some embodiments of the invention, the at least one nucleotide position which is mutated as compared to SEQ ID NO:6 is at least one nucleotide of the wild type M5 sequence set forth by SEQ ID NO: 16 (CAATG).

Non-limiting examples of isolated polynucleotides which include a mutation in at least one nucleotide of the wild type M5 sequence set forth by SEQ ID NO: 16 (CAATG) are provided in SEQ ID NOs:163-171.

According to some embodiments of the invention, the at least one nucleotide position which is mutated as compared to SEQ ID NO:6 is at least one nucleotide of the wild type M4 sequence set forth by SEQ ID NO: 15 (CATTC) and at least one nucleotide of the wild type M5 sequence set forth by SEQ ID NO: 16 (CAATG).

Non-limiting examples of isolated polynucleotides which include a mutation in at least one nucleotide of the wild type M4 sequence set forth by SEQ ID NO: 15 (CATTC) and a mutation in at least one nucleotide of the wild type M5 sequence set forth by SEQ ID NO: 16 (CAATG) are provided in SEQ ID NOs:172-180.

According to some embodiments of the invention, the isolated polynucleotide is for increasing expression of a heterologous polynucleotide operably linked thereto in cells other than endothelial cells. Such a polynucleotide can include mutations in M4 and/or M5 and wild type sequences of M6 and/or M7, in the presence or absence of additional sequences from element X, and/or in the presence of other mutated sequences from element X.

According to some embodiments of the invention, the isolated polynucleotide comprises a mutation in M4 (SEQ ID NO: 15) and/or in M5 (SEQ ID NO: 16) and at least one copy of the wild type M6 set forth by SEQ ID NO: 17 (GGGTG) and/or at least one copy of wild type M7 set forth by SEQ ID NO:18.

Non-limiting examples of isolated polynucleotides which include a mutation in at least one nucleotide of the wild type M4 sequence set forth by SEQ ID NO: 15 (CATTC) and at least one copy of the wild type M6 set forth by SEQ ID NO: 17 (GGGTG) are provided in SEQ ID NOs:181-182.

Non-limiting examples of isolated polynucleotides which include a mutation in at least one nucleotide of the wild type M5 sequence set forth by SEQ ID NO: 16 (CAATG) and at least one copy of the wild type M6 set forth by SEQ ID NO: 17 (GGGTG) are provided in SEQ ID NOs:183-189.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M6 set forth by SEQ ID NO: 17 (GGGTG) are provided in SEQ ID NOs:190-191.

According to some embodiments of the invention, the isolated polynucleotide further comprises at least one copy of the wild type M7 sequence set forth by SEQ ID NO: 18 (ACTTT).

Non-limiting examples of isolated polynucleotides which include a mutation in at least one nucleotide of the wild type M4 sequence set forth by SEQ ID NO: 15 (CATTC) and at least one copy of the wild type M7 sequence set forth by SEQ ID NO: 18 (ACTTT) are provided in SEQ ID NOs: 192-195.

Non-limiting examples of isolated polynucleotides which include a mutation in at least one nucleotide of the wild type M5 sequence set forth by SEQ ID NO: 16 (CAATG) and at least one copy of the wild type M7 sequence set forth by SEQ ID NO: 18 (ACTTT) are provided in SEQ ID NOs: 196-198.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M7 sequence set forth by SEQ ID NO: 18 (ACTTT) are provided in SEQ ID NOs:199-202.

According to some embodiments of the invention, the isolated polynucleotide further comprises at least one copy of the wild type M6 set forth by SEQ ID NO: 17 (GGGTG) and at least one copy of the wild type M7 sequence set forth by SEQ ID NO: 18 (ACTTT).

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M7 sequence set forth by SEQ ID NO: 18 (ACTTT) are provided in SEQ ID NOs:203-205.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M7 sequence set forth by SEQ ID NO: 18 (ACTTT) are provided in SEQ ID NOs:206-207.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M7 sequence set forth by SEQ ID NO: 18 (ACTTT) are provided in SEQ ID NOs:208-209.

According to some embodiments of the invention, the isolated polynucleotide reduces expression in cells of a heterologous polynucleotide operably linked thereto.

Such a polynucleotide can include mutations in M4, M5, M6 and/or M7, in the presence or absence of additional sequences from element X, and/or in the presence of other mutated sequences from element X.

According to some embodiments of the invention, the isolated polynucleotide comprises at least one mutation in wild type M4 (SEQ ID NO: 15) and/or in wild type M5 (SEQ ID NO:47) and in wild type M6 set forth by SEQ ID NO: 17 (GGGTG).

Non-limiting examples of isolated polynucleotides which include a mutation in at least one nucleotide of the wild type M4 sequence set forth by SEQ ID NO: 15 (CATTC) and a mutation in at least one nucleotide position of the wild type M6 set forth by SEQ ID NO: 17 (GGGTG) are provided in SEQ ID NOs:210-213.

Non-limiting examples of isolated polynucleotides which include a mutation in at least one nucleotide of the wild type M5 sequence set forth by SEQ ID NO: 16 (CAATG) and a mutation in at least one nucleotide position of the wild type M6 set forth by SEQ ID NO: 17 (GGGTG) are provided in SEQ ID NOs:214-222.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), and a mutation in at least one nucleotide position of the wild type M6 set forth by SEQ ID NO: 17 (GGGTG) are provided in SEQ ID NOs:223-231.

According to some embodiments of the invention, the isolated polynucleotide further comprises at least one mutation in wild type M7 set forth by SEQ ID NO: 18 (ACTTT).

Non-limiting examples of isolated polynucleotides which include a mutation in at least one nucleotide of the wild type M4 sequence set forth by SEQ ID NO: 15 (CATTC) and a mutation in at least one nucleotide position of the wild type M7 set forth by SEQ ID NO: 18 (ACTTT) are provided in SEQ ID NOs:232-236.

Non-limiting examples of isolated polynucleotides which include a mutation in at least one nucleotide of the wild type M5 sequence set forth by SEQ ID NO: 16 (CAATG) and a mutation in at least one nucleotide position of the wild type M7 set forth by SEQ ID NO: 18 (ACTTT) are provided in SEQ ID NOs:237-240.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), and a mutation in at least one nucleotide position of the wild type M7 set forth by SEQ ID NO: 18 (ACTTT) are provided in SEQ ID NOs:241-248.

According to some embodiments of the invention, the isolated polynucleotide further comprises at least one mutation in wild type M6 set forth by SEQ ID NO: 17 (GGGTG) and at least one mutation in wild type M7 set forth by SEQ ID NO: 18 (ACTTT).

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:249-258.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:259-264.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and a mutation in at least one nucleotide position of the wild type M7 set forth by SEQ ID NO: 18 (ACTTT) are provided in SEQ ID NOs:265-270.

According to some embodiments of the invention, the isolated polynucleotide comprises at least one copy of the wild type M8 sequence set forth by SEQ ID NO: 19 (GCTTC) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC) and at least one copy of the wild type M8 sequence set forth by SEQ ID NO: 19 (GCTTC) are provided in SEQ ID NOs: 271-279.

Non-limiting examples of isolated polynucleotides which include a mutation in at least one nucleotide of the wild type M5 sequence set forth by SEQ ID NO: 16 (CAATG) and at least one copy of the wild type M8 sequence set forth by SEQ ID NO: 19 (GCTTC) are provided in SEQ ID NOs: 280-287.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M8 sequence set forth by SEQ ID NO: 19 (GCTTC) are provided in SEQ ID NOs:288-291.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M8 sequence set forth by SEQ ID NO: 19 (GCTTC) are provided in SEQ ID NOs:294-298.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M8 sequence set forth by SEQ ID NO: 19 (GCTTC) are provided in SEQ ID NOs:299-301.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M8 sequence set forth by SEQ ID NO: 19 (GCTTC) are provided in SEQ ID NOs:302-303.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NOs:304-308.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NOs:309-311.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NOs:312-315.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NO:316.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NO:317.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M8 sequence set forth by SEQ ID NO: 19 (GCTTC) are provided in SEQ ID NO:318.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:319-327.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:328-333.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M8 sequence set forth by SEQ ID NO: 19 (GCTTC) are provided in SEQ ID NOs:334-337.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:338-344.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:345-348.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:349-354.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:355-361.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:362-365.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M8 sequence set forth by SEQ ID NO: 19 (GCTTC) are provided in SEQ ID NOs:366-369.

According to some embodiments of the invention, the isolated polynucleotide comprises at least one copy of the wild type M3 sequence set forth by SEQ ID NO: 21 (CTTTT) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC) and at least one copy of the wild type M3 sequence set forth by SEQ ID NO: 21 (CTTTT) are provided in SEQ ID NOs: 378-384.

Non-limiting examples of isolated polynucleotides which include a mutation in at least one nucleotide of the wild type M5 sequence set forth by SEQ ID NO: 16 (CAATG) and at least one copy of the wild type M3 sequence set forth by SEQ ID NO: 21 (CTTTT) are provided in SEQ ID NOs: 628-634.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG) and at least one copy of the wild type M3 sequence set forth by SEQ ID NO: 21 (CTTTT) are provided in SEQ ID NOs:370-377.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:385-390.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:391-396.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG) and at least one copy of the wild type M3 sequence set forth by SEQ ID NO: 21 (CTTTT) are provided in SEQ ID NOs:397-401.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:402-409.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:410-417.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:418-423.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:424-425.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NOs:538-540.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) and at least one copy of the wild type M3 sequence set forth by SEQ ID NO: 21 (CTTTT) are provided in SEQ ID NO:426.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG) and at least one copy of the wild type M3 sequence set forth by SEQ ID NO: 21 (CTTTT) are provided in SEQ ID NOs:427-435.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M3 sequence set forth by SEQ ID NO: 21 (CTTTT) are provided in SEQ ID NOs:436-444.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG) and at least one copy of the wild type M3 sequence set forth by SEQ ID NO: 21 (CTTTT) are provided in SEQ ID NOs:445-451.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:452-458.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:459-465.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NO:466.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:467-471.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:472-477.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT) and at least one copy of the wild type M3 sequence set forth by SEQ ID NO: 21 (CTTTT) are provided in SEQ ID NOs:478-483.

According to some embodiments of the invention, the isolated polynucleotide further comprises at least one copy of the wild type M8 sequence set forth by SEQ ID NO: 19 (GCTTC) and at least one copy of the wild type M3 sequence set forth by SEQ ID NO: 21 (CT-ITT) with additional wild type or mutated sequences derived from element X (SEQ ID NO:6).

Non-limiting examples of isolated polynucleotides which includes a mutation in at least one nucleotide of the wild type M4 sequence set forth by SEQ ID NO: 15 (CATTC), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:484-495.

Non-limiting examples of isolated polynucleotides which include a mutation in at least one nucleotide of the wild type M5 sequence set forth by SEQ ID NO: 16 (CAATG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:496-507.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:508-515.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:516-519.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:520-523.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:524-525.

Non-limiting examples of isolated polynucleotides which include a mutation in at least one nucleotide of the wild type M4 sequence set forth by SEQ ID NO: 15 (CATTC), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:526-529.

Non-limiting examples of isolated polynucleotides which include a mutation in at least one nucleotide of the wild type M5 sequence set forth by SEQ ID NO: 16 (CAATG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT)) are provided in SEQ ID NOs:530-533.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:534-535.

Non-limiting examples of isolated polynucleotides which include a mutation in at least one nucleotide of the wild type M4 sequence set forth by SEQ ID NO: 15 (CATTC), at least one copy of the wild type M6 set forth by SEQ ID NO: 17 (GGGTG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:536-537.

Non-limiting examples of isolated polynucleotides which include a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT) at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:538-539.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), at least one copy of the wild type M6 set forth by SEQ ID NO: 17 (GGGTG), at least one copy of the wild type M7 sequence set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NO:540.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:541-547.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), at least one copy of the wild type M8 sequence set forth by SEQ ID NO: 19

(GCTTC) and at least one copy of the wild type M3 sequence set forth by SEQ ID NO: 21 (CTTTT) are provided in SEQ ID NOs:548-554.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:555-559.

Non-limiting examples of isolated polynucleotides which include a mutation in at least one nucleotide of the wild type M4 sequence set forth by SEQ ID NO: 15 (CATTC), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:560-566.

Non-limiting examples of isolated polynucleotides which include a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:567-573.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:574-578.

Non-limiting examples of isolated polynucleotides which include a mutation in at least one nucleotide of the wild type M4 sequence set forth by SEQ ID NO: 15 (CATTC), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs: 579-583.

Non-limiting examples of isolated polynucleotides which include a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs: 584-588.

Non-limiting examples of isolated polynucleotides which include a mutation in at least one nucleotide of the wild type M4 sequence set forth by SEQ ID NO: 15 (CATTC), a mutation in at least one nucleotide of the wild type M5 sequence set forth by SEQ ID NO: 16 (CAATG), a mutation in at least one nucleotide position of the wild type M6 set forth by SEQ ID NO: 17 (GGGTG), a mutation in at least one nucleotide position of the wild type M7 set forth by SEQ ID NO: 18 (ACTTT), at least one copy of the wild type M8 sequence set forth by SEQ ID NO: 19 (GCTTC) and at least one copy of the wild type M3 sequence set forth by SEQ ID NO: 21 (CTTTT) are provided in SEQ ID NOs:589-592.

According to some embodiments of the invention, the isolated polynucleotide comprises at least one copy of wild type M3 sequence (SEQ ID NO: 21) and at least one copy of wild type M8 sequence (SEQ ID NO: 19), with at least one mutation in wild type M6 (SEQ ID NO: 17) and/or in wild type M7 (SEQ ID NO:50).

Non-limiting examples of isolated polynucleotides which include at least one copy of the wild type M8 sequence set forth by SEQ ID NO: 19 (GCTTC) and at least one copy of the wild type M3 sequence set forth by SEQ ID NO: 21 (CTTTT), with a mutation in at least one nucleotide of the wild type M6 sequence (SEQ ID NO: 17), and/or a mutation in at least one nucleotide of the wild type M7 (SEQ ID NO: 18) are provided in SEQ ID NOs:593-600.

The present inventors have envisaged that an isolated polynucleotide which includes the wild type M8 sequence (SEQ ID NO: 19) and/or the wild type M3 (SEQ ID NO: 21) sequence in addition to tissue specific enhancers (e.g., wild type M4 and/or wild type M5), and/or induced enhancers (e.g., developmentally related- or stress related-enhancers) is expected to exert a more specific regulatory effect by suppressing expression in non-target cells or under non-induced conditions.

According to some embodiments of the invention, the isolated polynucleotide comprises at least one copy of the wild type M8 sequence set forth by SEQ ID NO: 19 (GCTTC) and an endothelial specific enhancer sequence.

According to some embodiments of the invention, the isolated polynucleotide comprises at least one copy of the wild type M8 sequence set forth by SEQ ID NO: 19 (GCTTC) and at least one copy of wild type M4 sequence set forth by SEQ ID NO: 15.

According to some embodiments of the invention, the isolated polynucleotide comprises at least one copy of the wild type M8 sequence set forth by SEQ ID NO: 19 (GCTTC) and at least one copy of wild type M5 sequence set forth by SEQ ID NO:16.

According to some embodiments of the invention, the isolated polynucleotide comprises at least one copy of the wild type M8 sequence set forth by SEQ ID NO: 19 (GCTTC), at least one copy of wild type M4 sequence set forth by SEQ ID NO: 15 and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT) and an endothelial specific enhancer sequence.

According to some embodiments of the invention, the isolated polynucleotide comprises at least one copy of the wild type M3 sequence set forth by SEQ ID NO: 21 (CTTTT) and at least one copy of wild type M4 sequence set forth by SEQ ID NO: 15.

According to some embodiments of the invention, the isolated polynucleotide comprises at least one copy of the wild type M3 sequence set forth by SEQ ID NO: 21 (CTTTT) and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT), at least one copy of wild type M4 sequence set forth by SEQ ID NO: 15 and at least one copy of wild type M5 sequence set forth by SEQ ID NO:16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and an endothelial specific enhancer sequence.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one copy of wild type M4 sequence set forth by SEQ ID NO: 15.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one copy of wild type M5 sequence set forth by SEQ ID NO: 16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC), at least one copy of wild type M4 sequence set forth by SEQ ID NO: 15 and at least one copy of wild type M5 sequence set forth by SEQ ID NO: 16.

According to some embodiments of the invention, the isolated polynucleotide comprises at least one copy of the wild type M3 sequence set forth by SEQ ID NO: 21 (CTTTT), at least one copy of wild type M8 sequence set forth by SEQ ID NO: 19 (GCTTC) and at least one enhancer element such as wild type M6 (SEQ ID NO: 17) and/or wild type M7 sequence (SEQ ID NO:18).

According to some embodiments of the invention, the isolated polynucleotide includes at least one copy of wild type M8 with additional flanking sequences such as at least one copy of a wild type M8 sequence (SEQ ID NO: 19), at least one copy of wild type M7 (SEQ ID NO: 18) and/or wild type M9 sequence (SEQ ID NO: 14, CTGGA); and/or the isolated polynucleotide includes at least one copy of wild type M8 and at least one mutation in M7, with or without M9 (SEQ ID NO: 22). Such polynucleotides can be used as a non-specific repressor.

According to some embodiments of the invention, the isolated polynucleotide is for increasing expression of a heterologous polynucleotide operably linked thereto in cells/tissues.

According to some embodiments of the invention, the isolated polynucleotide comprises at least one copy of wild type M6 sequence set forth by SEQ ID NO: 17 (GGGTG) and/or at least one copy of wild type M7 sequence set forth by SEQ ID NO: 18 (ACTTT).

According to some embodiments of the invention, the isolated polynucleotide includes at least one copy of wild type M6 (SEQ ID NO: 17) and a mutation in at least one nucleotide of wild type M8 (SEQ ID NO: 19).

Non-limiting examples of isolated polynucleotide which include at least one copy of wild type M6 (SEQ ID NO: 17) and a mutation in at least one nucleotide of the wild type M8 (SEQ ID NO: 19) are provided in SEQ ID NOs:23-26.

According to some embodiments of the invention, the isolated polynucleotide includes at least one copy of wild type M7 (SEQ ID NO: 18) and a mutation in at least one nucleotide of wild type M8 (SEQ ID NO: 19).

Non-limiting examples of isolated polynucleotide which include at least one copy of wild type M7 (SEQ ID NO: 18) and a mutation in at least one nucleotide of the wild type M8 (SEQ ID NO: 19) are provided in SEQ ID NOs:27-28.

According to some embodiments of the invention, the isolated polynucleotide includes at least one copy of wild type M6 (SEQ ID NO: 17), at least one copy of wild type M7 (SEQ ID NO: 18) and a mutation in at least one nucleotide of wild type M8 (SEQ ID NO: 19).

According to some embodiments of the invention, the isolated polynucleotide includes at least one copy of wild type M1 (SEQ ID NO: 20) and a mutation in at least one nucleotide of wild type M8 (SEQ ID NO: 19).

Non-limiting examples of isolated polynucleotide which include at least one copy of wild type M1 (SEQ ID NO: 20) and a mutation in at least one nucleotide of the wild type M8 (SEQ ID NO: 19) are provided in SEQ ID NOs:43-54 and 601-632.

According to some embodiments of the invention, the isolated polynucleotide includes at least one copy of wild type M1 (SEQ ID NO: 20), at least one copy of wild type M6 (SEQ ID NO: 17) and/or at least one copy of wild type M7 (SEQ ID NO: 18) and a mutation in at least one nucleotide of wild type M8 (SEQ ID NO: 19).

Non-limiting examples of isolated polynucleotides which include a mutation in at least one nucleotide of wild type M8 (SEQ ID NO: 19) and at least one copy of wild type M1 (SEQ ID NO: 20), wild type M6 (SEQ ID NO: 17) and/or wild type M7 (SEQ ID NO: 18) are provided in SEQ ID NOs:29-42.

Additional examples of regulatory isolated polynucleotides which can be used according to some embodiments of the invention are provided (SEQ ID NOs: 633-644) in the Examples section which follows.

According to an aspect of some embodiments of the invention, there is provided an isolated polynucleotide comprising a nucleic acid sequence which comprises a first polynucleotide comprising the pre-proendothelin (PPE-1) promoter set forth by SEQ ID NO:13 and a second polynucleotide comprising at least one copy of a nucleic acid sequence selected from the group consisting of:

(i) wild type M4 sequence set forth by SEQ ID NO: 15 (CATTC), (ii) wild type M5 sequence set forth by SEQ ID NO: 16 (CAATG), (iii) wild type M8 sequence set forth by SEQ ID NO: 19 (GCTTC), (iv) wild type M6 sequence set forth by SEQ ID NO: 17 (GGGTG), (v) wild type M7 sequence set forth by SEQ ID NO: 18 (ACTTT);

(vi) wild type M1 sequence set forth by SEQ ID NO: 20 (GTACT), and (vii) wild type M3 sequence set forth by SEQ ID NO: 21 (CTTTT);

with the proviso that the second polynucleotide is not SEQ ID NO:6 (element X), and wherein the isolated polynucleotide is not SEQ ID NO:12 (PPE-1-3X).

According to some embodiments of the invention, each of the wild type M4, M5, M8, M6, M7 and/or M1 sequences is placed in a head to tail (5'→3) orientation with respect to the PPE-1 promoter set forth by SEQ ID NO:13.

According to some embodiments of the invention, each of the wild type M4, M5, M8, M6, M7 and/or M1 sequences is placed in a tail to head (3'→5) orientation with respect to the PPE-1 promoter set forth by SEQ ID NO:13.

According to some embodiments of the invention, the wild type M4, M5, M8, M6, M7 and/or M1 sequences are placed in various orientations (head to tail or tail to head) and/or sequential order with respect the other wild type M4, M5, M8, M6, M7 and/or M1 sequences, and/or with respect to the orientation of SEQ ID NO:13.

Construction of such viral vectors may be effected using known molecular biology techniques such as those described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986].

Construction of the viral vector of SEQ ID NO: 9 is described in International Application WO/2008/132729, the contents of which are incorporated herein by reference.

The viral vector of this aspect of the present invention may be administered per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the viral vector of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections. Injection of the viral vectors into a spinal fluid can also be used as a mode of administration.

In order to enhance delivery of the virus to the central nervous system (CNS) various approaches may be taken. These include: neurosurgical strategies (e.g., intracerebral injection or intracerebroventricular infusion) and molecular manipulation of the virus. Thus for example, Tang et al., Gene Therapy (2007) 14, 523-532 teaches re-directing Ad5 vectors to the MTf transcytosis pathway in order to cross the BBB by manipulating the virus to express a full-length melanotransferrin (sCAR-MTf) polypeptide.

Other approaches for enhancing the delivery of the virus to the CNS include pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

The present invention also contemplates engineering of the viral vectors in order to avoid, suppress or manipulate the immune response, ideally resulting in sustained expression and immune tolerance to the transgene product—such methods are described for example in Nayak et al., *Gene Therapy* (12 Nov. 2009), incoporated herein by reference.

Alternately, one may administer the pharmaceutical composition in a local rather than systemic manner, for example, via injection of the pharmaceutical composition directly into the brain of a patient and even more directly into the tumor cells themselves.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (i.e. viral particles) effective to prevent, alleviate or ameliorate symptoms of a disorder (e.g., glioblastoma) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The therapeutically effective amount of the active ingredient can be formulated in a unit dose. As used herein "unit dose" refers to a physically discrete unit containing a predetermined quantity of an active material calculated to individually or collectively produce a desired effect such as an anti-cancer effect. A single unit dose or a plurality of unit doses can be used to provide the desired effect, such as an anti-cancer therapeutic effect.

According to one embodiment, about $10^3$ to about $10^{16}$ virus particles are administered to the subject.

According to another embodiment, about $10^5$ to about $10^{13}$ virus particles are administered to the subject.

According to one embodiment, about $10^7$ to about $10^{12}$ virus particles are administered to the subject.

According to one embodiment, about $1\times10^{12}$ to about $5\times10^{12}$ virus particles are administered to the subject.

According to one embodiment, about $1\times10^{13}$ to about $5\times10^{13}$ virus particles are administered to the subject.

According to yet another embodiment the subject is administered intravenously with $1\times10^{12}$-$1\times10^{13}$ viral particles of SEQ ID NO: 9. or SEQ ID NO: 10.

According to yet another embodiment the subject is administered intravenously with at least two doses of $1\times10^{12}$-$1\times10^{13}$ viral particles of SEQ ID NO: 9. or SEQ ID NO: 10. According to yet another embodiment the subject is administered intravenously with at least three or more doses of $1\times10^{12}$-$1\times10^{13}$ viral particles of SEQ ID NO: 9. or SEQ ID NO: 10. In a particular embodiment, the at least two doses are administered at least about 1 day, at least about 3 days, at least about 5 days, at least about 7 days, at least about 2 weeks, at least about 3 weeks, at least about 4 weeks, at least about 2 months, at least about 6 months, at least about 9 months, at least about 1 year, at least about 1.25 years, at least about 1.5 years, at least about 1.75 years, at least about 2 years, at least about 2.5 years, at least about 3 years or more apart.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The vectors of the present invention may be administered with additional ingredients which may improve the uptake of the nucleic acid construct by the cells, expression of the chimeric polypeptide by the nucleic acid construct in the cells, or the activity of the expressed chimeric polypeptide.

For example, the uptake of adenoviral vectors into EC cells can be enhanced by treating the vectors with engineered antibodies or small peptides. Such "adenobody" treatment, was shown effective in directing adenovirus constructs to EGF receptors on cells (Watkins et al 1997, Gene Therapy 4:1004-1012). In addition, Nicklin et al have shown that a small peptide, isolated via phage display, increased specificity and efficiency of vectors in endothelial cells and decreased the expression in liver cells in culture (Nicklin et al 2000, Circulation 102:231-237). In a recent study, an FGF retargeted adenoviral vector reduced the toxicity of tk in mice (Printz et al 2000, Human Gene Therapy 11:191-204).

Low dose radiation has been shown to cause breaks in DNA strands primarily in the G2/M phase, cell membrane damage enhancing the bystander effect, and thus may potentiate other cytotoxic and anti-neoplastic therapies, when administered in combination. Vascular endothelial cells may be particularly suitable to such combination, or adjunct, therapies, since it has been demonstrated that low dose radiation specifically targets the apoptotic system of the microvascular endothelial cells (Kolesnick et al., Oncogene 2003; 22:5897-906). Angiostatin has been shown to potentiate the therapeutic effects of low dose radiation (Gorski et al. Can Res 1998; 58:5686-89). However, the effects of radiation are still poorly understood, since irradiation has also been shown to increase pro-angiogenic "tissue repair factors" (Itasaka et al., Am Assoc Canc Res, 2003; abstract 115). Similarly, certain chemotherapeutic agents have been shown to activate specific cytotoxic and apoptotic pathways [doxorubicin, cisplatin and mitomycin C induce accumulation of Fas receptor, FADD, and other proapoptotic signals in the FADD/MORT-1 pathway (Micheau et al., BBRC 1999 256:603-07)].

For example International Application WO/2008/132729 teaches combined doxorubicin and AdPPE-1 (3x)-Fas-c chimera construct administration in endothelial cells (BAEC). Thus, the viral vectors and the pharmaceutical compositions comprising same of the present invention can be used to treat malignant gliomas alone or in combination with one or more other established or experimental therapeutic regimen for such disorders. Therapeutic regimen for treatment of malignant gliomas suitable for combination with the viral vectors of the present invention include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole;

Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Temozolomide (Temodar™); Bevacizumab, Dorafinib, Sorafenib (Nexavar™), Sunitinib (Sutent™), Vandetanib (ZD6474; Zactimam), Pazopanib (GW786034), and Vatalanib (PTK787), Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

The viral vectors of the present invention may also be administered with an agent that enhances expression of transgenes in adenoviral-mediated transient expression. For example International Application WO/2008/132729 teaches administration of a corticosteroid (e.g. dexamethasone and/or N-Acetyl Cysteine (NAC) prior to AdPPE-1 (3x)-Fas-c chimera construct administration.

In addition, the viral vectors of the present invention may also be administered with an agent that brings about transient immunosuppression, such as for example deoxyspergualin (DSG) or cyclophosphamide (see for example Smith et al., Gene Ther. 1996 June; 3(6):496-502) in order to allow for repetitive dosing.

It is expected that during the life of a patent maturing from this application many relevant chemotherapeutic agents will be developed and the scope of the term chemotherapeutic agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Effect of VB-111 in an Animal Model of Glioblastoma

Materials and Methods

Construction and Cloning of the Viral Vector:

The vector was constructed using a backbone containing most of the genome of adenovirus type 5, as well as partial homology to an adaptor plasmid, which enables recombination.

The E1 early transcriptional unit was deleted from the backbone plasmid, and further modified by deleting the pWE25 and the Amp resistance selection marker site.

The adaptor plasmid, containing sequences of the Ad5, CMV promoter, MCS, and SV40 polyA was modified to delete deleting the CMV promoter, and the PPE-1 promoter and Fas-c fragment were inserted by restriction digestion.

The modified PPE-1 promoter (PPE-1-3X, SEQ ID NO: 12) and the Fas-chimera transgene (Fas-c, SEQ ID NO: 4) were utilized for construction of the adenoviral vector. The PPE-1-(3X)-Fas-c element (2115 bp) was constructed from the PPE-1-(3X)-luc element. This element contains the 1.4 kb of the murine preproendothelin PPE-1-(3X) promoter, the Luciferase gene, the SV40 polyA site and the first intron of the murine ET-1 gene, originated from the pEL8 plasmid (8848 bp) used by Harats et al (Harats D. et al., JCI, 1995). The PPE-3-Luc cassette was extracted from the pEL8 plasmid using the BamHI restriction enzyme. The Luciferase gene was substituted by the Fas-c gene [composed of the extra cellular and intra membranal domains of the human TNF-R1 (Tumor Necrosis Factor Receptor 1, SEQ ID NO: 2) and of the Fas (p55) intracellular domain (SEQ ID NO: 3) (Boldin et al, JBC, 1995)] to obtain the PPE-1-3X-Fas-c cassette.

PPE-1(3X)-Fas-c Plasmid—The cassette was further introduced into the backbone plasmid by restriction digestion, resulting with the PPE-1(3X)-Fas-c plasmid.

Adaptor-PPE-1(3X)-Fas-c Plasmid—The PPE-1-3X-Fas-c element was extracted from the first generation construct PPE-1-3X-Fas-c plasmid, and was amplified with designated PCR primers introducing SnaB1 and EcoR1 restriction sites at the 5'-and-3'-end respectively. These sites were used to clone the PPE-Fas-c fragment into the adaptor plasmid digested with SnaB1 and EcoR1, resulting in the adaptor-PPE-1-3X-Fas-c used for transfection of the host cells (for example, PER.C6 cells).

Figure 1:
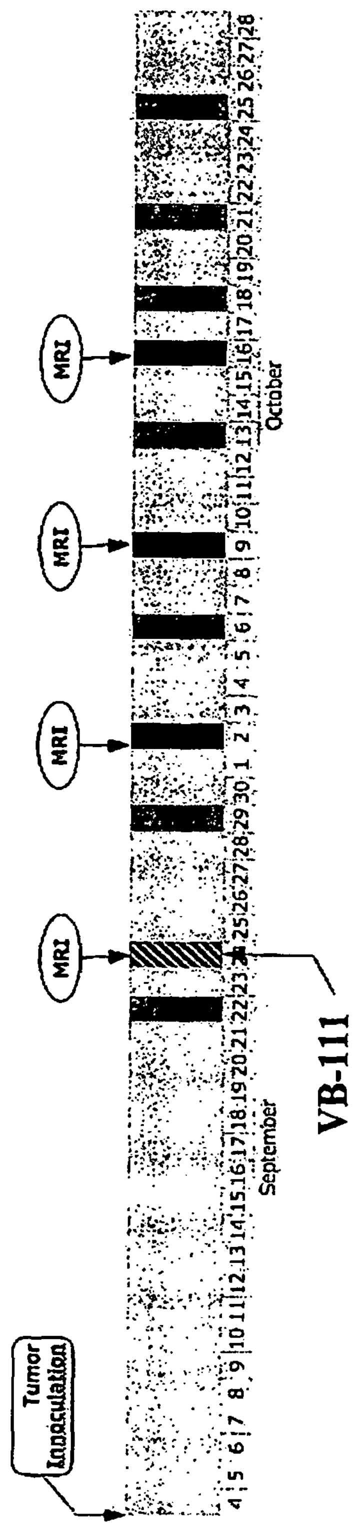
FIG. 1 is a time chart illustrating an exemplary treatment schedule to measure the in-vivo effects of VB-111 in nude rats pre-inoculated with U87 tumor cells.

Xenografts:

$10^6$ U87 human glioma tumor cells expressing a biofluorescent/bioluminescent protein (luciferase) were implanted intracranially in the striatum of athymic nude rats (NxGen BioSciences). Animals were anesthesized with isoflurane prior to implantation. Briefly, glioma tumor cells expressing luciferase were implanted intracranially in the striatum of athymic nude rats (NxGen BioSciences). Animals were anesthesized with isoflurane prior to implantation and placed secured on a Just for Mice Stereotaxic (Stoelting) apparatus. A 1 cm incision was made in the scalp and the bregma identified. A small burr hole was made in the cranium using a mounted Micromotor drill (Stoelting) at the identified position (1 mm forward and 4 mm lateral of the bregma). $1\times10^6$ cells in a volume of 5 ul were injected into the caudate over 5 minutes using a Quintessential Stereotaxic Injector (Stoelting) containing a 10 ul Hamilton syringe mounted to the stereotaxic device to assure appropriate placement. Animals were imaged following isofluorane sedation using an IVIS chemiluminescence system. The fluorescence/bioluminescence of these tumors are typically detectable within 7-10 days due to rapid growth and high expression of the marker. An alternative imaging modality, i.e. MRI, was also utilized to assist with tumor visualization. Animals received chemical anesthesia for MRI imaging. Once tumor establishment and growth was detected (variable depending on the rate of growth for the respective line), rats were treated with VB-111. The total dose was $10^{11}$ vp in a volume of 100 ul. Control groups received vehicle only. Animals were monitored for tumor growth or response through non-invasive imaging of fluorescence/luminescence—see FIG. 1 for a typical treatment and monitoring regimen.

Experimental Protocol:

Two types of tumor growth experiments were performed, tumor growth inhibition (TGI) and tumor growth delay (TGD). The TGI experiment was terminated when the animals showed clinical signs of tumor development i.e. become dull, listless, or moribund, usually prior to 4 weeks post-implantation, as median survival of 28-29 days has been typically observed in prior studies. Upon termination, all rats were weighed, sacrificed, and their tumors excised. For a TGD experiment, animals were sacrificed on an individual basis and tumor-related parameters (e.g. size) were measured. The average day of sacrifice was determined for all groups, and the tumor growth delay (TGD) for each treatment group compared to the control group was calculated.

MRI:

Magnetic resonance imaging has shown to be capable of demonstrating early changes within the tumor vasculature without any invasive measures. It is possible to generate maps of blood volume and blood flow, vascular permeability, white matter tracks, and apparent diffusion coefficient. These parameters offer clinically relevant physiological information that could help to characterize, stage tumor growth, and evaluate treatment efficacy. MRI was performed on a Bruker 7 Tesla scanner. Blood flow and blood volume was measured using dynamic contrast enhanced imaging technique following a bolus of gadopentetate-dimeglumine (GdDTPA). White matter tracks and apparent diffusion coefficient was measured using diffusion tensor imaging. Vascular permeability was measured using T1-weighted MRI obtained prior to and following contrast (Gd-DTPA) injection. For dynamic contrast enhanced MRI, single-shot gradient echo planar imaging (EPI) was used, resolution at 0.27×0.27×0.5 mm, 5 slices (no gap), matrix=96×96, field of view=25.6×25.6 mm, repetition time TR=0.5 s, echo time TE=20 ms. For diffusion tensor imaging, single-shot spin-echo echo-planar imaging K was used, resolution be 0.27×0.27×0.5 mm, 15 slices (no gap), matrix=96×96, field of view=25.6×25.6 mm, repetition time TR=2 s, echo time TE=40 ms, b value=0 s/mm$^2$, and 6 diffusion direction of b=1100 s/mm$^2$. For T1-weighted MRI, conventional acquisition was used, resolution 0.27×0.27×0.5 mm, 15 slices (no gap), matrix=96×96, field of view=25.6×25.6 mm, repetition time TR=0.5 s, echo time TE=ms. The number of slices analyzed adequately covered the entire tumor region and roughly cover the entire cerebrum.

The maps described above were calculated using standard software. For permeability maps, the maps were processed using codes in Matlab to obtain maps of Ktrans (corresponding roughly to wash-in rates of the contrastagent. Ktrans can be influenced by flow, or by permeability, or both. In high-flow organs such as the brain, flow limitations are not usually a concern, but the blood-brain barrier severely limits permeability unless it is disrupted by disease. Even in such a state, Ktrans does not fully correspond to permeability, but it is related rather to the permeability*surface area product of the capillary bed (in nonflow-limited situations).

Histopathology:

To further characterize changes at the microscopic level, animals were sacrificed by cardiac puncture, followed by intracardiac saline and formalin irrigation. Necropsy was performed, and brains underwent standard H&E processing. The number of vessels per medium power field were counted.

Results

As illustrated in FIG. 2, animal death began at approximately day 32. The median survival for the control group was 39.25 (+/−3.8) days and for the treatment group was 45.8 days.

Luciferase Activity:

Luciferase activity was followed by ip injection of luciferin and optical imaging on a Xenogen system. The region of interest was generated automatically without manipulation and total photons recorded. As illustrated in FIG. 3, a clear separation in activity was observed at day 33 with a mean (SD) in the control group of 9.7 (2.9)$\times 10^6$ versus 5.3 (6.2)$\times 10^5$ in the treated group.

MRI:

As illustrated in FIG. 4, mean of the maximum diameters of tumors in the VB111 treated group was smaller than those for controls.

Example 2

Effect of VB-111 in Glioblastoma Patients

Treatment Plan:

VB-111 will be administered as a single intravenous infusion of $1\times 10^{12}$ or $3\times 10^{12}$ Dose.

Study consists of 2 cohorts.

Cohort 1a: 3-6 subjects, safety ($1\times 10^{12}$ VPs);

Cohort 1b: 3-6 subjects, safety ($3\times 10^{12}$ VPs);

Cohort 2: 23-26 subjects, efficacy & safety ($3\times 10^{12}$ VPs)

Cohort 1a & Cohort 1b: Study subjects will be enrolled sequentially. The first subject of each cohort will be treated and observed for 14 days; if no dose-limiting toxicities (DLT) are observed, then another two subjects will be recruited to that cohort. All six subjects of cohort 1 need to be observed for a minimum of 14 days and show no DLT for the start of the next cohort. If a DLT is observed in one patient in a specific dosing cohort, three additional subjects will be accrued for the same dosing cohort, and safety will be reassessed. If DLT is confirmed, i.e. two out of six subjects experience a DLT, then the study will be discontinued. All subjects in cohorts 1a and 1b must be observed for a minimum of 28 days prior to commencing cohort 2.

The study will be conducted according to the Simon's 2 step method. A total of 29 subjects are anticipated to enroll at the $3\times 10^{12}$ VP dose level (3-6 from cohort 2 and 23-26 in cohort 3). Step one will include the first 10 patients at this dose level. A subject will be considered to have a response if s/he has either 6 months progression free survival or at least a partial tumor response according to Rano criteria. An interim analysis will be performed after 10 patients from cohorts 2 and 3 have completed the study. If 2 or more responses occur in the step 1 subjects, step 2 will commence, enrolling an additional 19 subjects.

The following study stopping rule for halting the study will be applied:

A) If 3 out of 6 (or 5 out of 9 or 6 out of 12) subjects in the cohort 1a & 1b experience drug related DLT.

B) If 2 out of the subjects in cohort 1a experience a DLT.

C) If ANY death occurs within two weeks after the product is given, except death due to disease progression or clearly unrelated to study drug. Enrollment will be temporarily suspended for an ad hoc, emergency IDMC meeting to review the case and make a recomnmendation if enrolment can be reinstated.

When safety end point is achieved for cohorts 1a and 1b (day 28), eligible subjects will be enrolled into the study and commence cohort 2. It is expected that 26 GBM subjects will be enrolled into cohort 2 for additional safety and efficacy endpoints (or 23 patients if 6 were enrolled in cohort 2).

One dote of VB 111 ($1\times 10^{12}$, $3\times 10^{12}$ or $1\times 10^{13}$ VPs) administered within 3 weeks after the screening visit. Subjects will return to the clinic for follow up visits at days 4, 7, 14 and 28 and on monthly schedule on days 56, 84, 112, 140 and 168 if no disease progression has occurred prior to the visit.

On days 7, 14, 28, 56, 112 and 168, subjects will be assessed for response using contrast and non-contrast brain magnetic resonance imaging (MRI) with assessment based on the RANO criteria.

The post study follow up period will include telephone contacts every two months after day 168, early termination, or disease progression (whichever occurs earlier) to follow up on survival. Follow up will continue until patient expires. The study duration is 7 months (6 months post dose), thereafter the subjects will be followed by telephone for survival data every two months. Surveillance MRIs will be performed every 2 months until 1 year, and then every 3 months until 2 years post dosing (or until progression).

Population:

Up to 35 eligible subjects (cohort 1 & cohort 2) with relapsed GBM.

Main Inclusion Criteria:

1. Ability to understand and the willingness to sign a written informed consent document.

2. Subjects≥18 years of age

3. Subjects must have histologically confirmed diagnosis of primary malignant glioma (glioblastoma multiforme, gliosarcoma or anaplastic astrocytoma, or anaplastic oligodendroglioma). Subjects with recurrent disease whose diagnostic pathology confirmed malignant glioma (glioblastoma multiforme, gliosarcoma or anaplastic astrocytoma, or anaplastic oligodendroglioma) will not need re-biopsy.

4. Evidence of measurable recurrent or residual primary CNS neoplasm on contrast-enhanced MRI, unless medically contraindicated (CT scan will then be used).

5. Measurable disease by RANO criteria.

6. Avastin and anti-angiogenic (TKIs such as sunitinib or sorafenib) naive subjects.

7. Disease progression or recurrence following standard of care treatment with radiotherapy and temozolomide.

8. An interval of at least 4 weeks between prior surgical resection and study enrolment.

9. Completed radiotherapy ≥90 days before study starts.

10. An interval of at least 12 weeks between prior radiotherapy or at least 4 weeks from prior chemotherapy, and enrolment on this protocol.

11. Recovered to Grade 1 or less from the toxic effects of any earlier intervention.

12. Karnofsky performance status a 60%.

13. Adequate renal, liver, and bone marrow function according to the following criteria:

Absolute neutrophil count≥1500/mcL

Platelets≥125 000/mcL

Total bilirubin within upper limit of normal (ULN)

Aspartate aminotransferase (AST)≤2.5X institutional ULN

Creatinine within normal limits or creatinine clearance≥50 mL/min for patients with creatinine levels above normal limits.

PT, PTT greater than 80% of the lower normal limits.

13. Subjects must be treated with corticosteroids on day O, Subjects will be on a stable dose for 1 week prior to entry, and is not anticipated to require increase in steroid dose throughout the study.

14. No evidence of haemorrhage on the baseline MRI or CT scan.

15. Males and Females of childbearing potential must utilize, throughout the course of the trial a standard contraception method.

Cohort 1a and 1b Additional Eligibility Criteria:

Subjects without major mass effect of Tumor.

Main Exclusion Criteria:

1. Pregnant or breastfeeding subjects

2. Co-medication that may interfere with study results; e.g. immuno-suppressive agents other than corticosteroids 3. Active Infection.

4. Greater than 3 prior recurrences.

5. Evidence of CNS haemorrhage CTCAE on baseline MRI or CT scan.

6. Requires therapeutic anti-coagulation.

7. Prior anti-angiogenic therapy including VEGF-sequestering agents (e.g. bevicizumab, aflibercept) or VEGF inhibitors (e.g. cedirinib, pazopanib, sunitinib, sorafenib).

8. Prior stereotactic radiotherapy.

9. Known active secondary malignancy.

10. Expected to have surgery during study period.

11. Subjects, who suffered from an acute cardiac event within the last 12 months.

12. Subjects with active vascular disease, either myocardial or peripheral

13. Subjects with proliferative and/or vascular retinopathy

14. Subjects with known liver disease (alcoholic, drug/toxin induced, genetic, or autoimmune).

15. Subjects with known CNS metastatic disease (other than GBM).

16. Subjects with known active second malignancy.

17. Subjects testing positive to one of the following viruses: HIV, HBV and HCV

18. Subjects that have undergone major surgery within the last 4 weeks before enrolment.

19. Subjects may not have received any other investigational agent within 4 weeks before enrolment.

20. Uncontrolled intercurrent illness including, but not limited to ongoing or active infection, symptomatic congestive heart failure, unstable angina pectoris, cardiac arrhythmia, or psychiatric illness/social situations that would limit compliance with study requirements Test Drug and Formulation:

VB-111 (SEQ ID NO: 9 or 10) is formulated as a sterile vector solution. The solution is supplied frozen (below −65° C.), in single use, plastic screw cap vials. Each vial contains 1.1 mL of vector solution at a viral titer of $1\times10^{12}$ VP/ml. The vector solution should be thawed and maintained on ice during dilution and handling for a maximum of 3 hours.

Dosage and Administration:

Prior to infusion, the solution for injection should be brought to room temperature Maximum time for drug in saline is 1 hour at room temperature. The vials should be opened in a biological safety cabinet and injected into 4 mL of normal saline for infusion for each 1 ml of drug. ie; for the $1\times10^{12}$ viral particle (VP) dose 1 ml of drug+4 ml of saline, for the $3\times10^{12}$ VP dose 3 ml of drug+12 ml of saline. A single infusion of approximately 5 mL/15 ml of diluted VB-111 should be administered 1 mL/minute.

Safety Evaluations:

Adverse events will be recorded on an ongoing basis and up to 2 months following the administration of the test drug. Adverse events will be assessed for seriousness, relatedness to study drug, and severity (according to CTCAE 4.0). Vital signs will be recorded at screening, prior to dosing, 30, 60 minutes, 4 and 6 hours after dosing and at all patient visits. A physical examination will be conducted at screening, days 14, 28, 56, 84, 112, 140, 168 and at the end of the study. A 12 lead ECG will be obtained at screening, prior to dosing and on days 28 and 168 (or ET). Safety laboratory assessment (blood haematology and chemistry, urine analysis) will be conducted at screening, prior to dosing, and at all patient visits, starting from day 4±1 to 168±7.

Distribution:

Blood and urine samples will be collected prior to dosing, at the end of the infusion, days 4, 7, 14, 28 and 56, for evaluation of levels of virus DNA (in whole blood and urine) and its transgene (in whole blood).

Tumor Response:

Tumor response will be assessed at screening, prior to dosing, days 14, 28, 56, 112, 140 and 168, and then every 2 months for 1 year and every 3 months for 2 years post dosing, using contrast and non-contrast brain magnetic resonance imaging (MRI) with assessment based on the RANO criteria, until progression of disease (local and central independent radiology review). For patients who do not progress or die, PFS will be censored at the time of initiation of alternative anticancer therapy, date of last radiologic assessment, or time of last contact.

Although the invention has been described in conjunction with specific to embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a malignant glioma in a subject in need thereof, the method comprising administering directly into the malignant glioma or intravenously to the subject a therapeutically effective amount of a non-replicating adenovirus serotype 5 vector (Ad5), wherein said adenoviral vector comprises:

(i) a first nucleotide sequence comprising the nucleotide sequence of the extracellular region of TNFR1 as set forth in SEQ ID NO:2 fused to the trans-membrane and intracellular regions of Fas as set forth in SEQ ID NO:3 encoding a Fas-chimera (Fas-c); and (ii) a second nucleotide sequence of an endothelial cell-specific promoter comprising the nucleotide sequence as set forth in SEQ ID NO:6, or the complementary sequence thereof, wherein said second nucleotide sequence is operably linked to and is upstream of said first nucleotide sequence for expression of said Fas-chimera in endothelial cells, and wherein growth of the malignant glioma is inhibited.

2. The method of claim 1, wherein said promoter comprises at least two copies of the nucleotide sequence as set forth in SEQ ID NO: 6, or the complementary sequence thereof.

3. The method of claim 1, wherein said promoter further comprises the nucleotide sequence as set forth in SEQ ID NO: 8, or the complementary sequence thereof.

4. The method of claim 1, wherein said promoter comprises the nucleotide sequence as set forth in SEQ ID NO: 7, or a complementary sequence thereof.

5. The method of claim 1, wherein said promoter further comprises the hypoxia response element (HRE) as set forth in SEQ ID NO: 5.

6. The method of claim 1, wherein the malignant glioma is selected from the group consisting of glioblastoma, astrocytoma, oligodendroglioma, ependymoma, and juvenile pilocystic astrocytoma.

7. The method of claim 1, wherein the therapeutically effective amount of said adenoviral vector is $10^{13}$ virus particles.

8. The method of claim 1, wherein said administering comprises intravenous administration.

9. The method of claim 1, wherein said administering is in at least two doses of said adenoviral vector.

10. The method of claim 1, wherein said administering is at least three doses of said adenoviral vector.

11. The method of claim 1, wherein the adenoviral vector is administered as a single unit dose.

12. The method of claim 1, further comprising administering to the subject an anti-cancer drug.

13. The method of claim 12, wherein said anti-cancer drug is bevacizumab.

14. The method of claim 1, further comprising administering a therapy selected from the group consisting of chemotherapy, radiotherapy, phototherapy, photodynamic therapy, surgery, nutritional therapy, ablative therapy, brachiotherapy, proton beam therapy, immunotherapy, cellular therapy and photon beam radiosurgical therapy.

15. The method of claim 14, wherein said therapy is immunotherapy.

16. The method of claim 1, wherein said administering comprises intravenous administration, and wherein the malignant glioma is a glioblastoma.

17. The method of claim 16, wherein the therapeutically effective amount of said adenoviral vector is $10^{13}$ virus particles.

* * * * *